(12) United States Patent
Hammock et al.

(10) Patent No.: US 12,251,379 B2
(45) Date of Patent: Mar. 18, 2025

(54) METHODS OF INHIBITING FORMATION OF ALPHA SYNUCLEIN AGGREGATES

(71) Applicants: THE REGENTS OF THE UNIVERSITY OF CALIFORNIA, Oakland, CA (US); CHIBA UNIVERSITY, Chiba (JP)

(72) Inventors: Bruce D. Hammock, Davis, CA (US); Sung Hee Hwang, Woodland, CA (US); Kenji Hashimoto, Chiba (JP); Qian Ren, Chiba (JP)

(73) Assignees: THE REGENTS OF THE UNIVERSITY OF CALIFORNIA, Oakland, CA (US); CHIBA UNIVERSITY, Chiba (JP)

( * ) Notice: Subject to any disclaimer, the term of this patent is extended or adjusted under 35 U.S.C. 154(b) by 1064 days.

(21) Appl. No.: 16/967,115

(22) PCT Filed: Feb. 5, 2019

(86) PCT No.: PCT/US2019/016717
§ 371 (c)(1),
(2) Date: Aug. 3, 2020

(87) PCT Pub. No.: WO2019/156991
PCT Pub. Date: Aug. 15, 2019

(65) Prior Publication Data
US 2021/0161881 A1  Jun. 3, 2021

Related U.S. Application Data

(60) Provisional application No. 62/626,685, filed on Feb. 6, 2018.

(51) Int. Cl.
*A61K 31/453* (2006.01)
*A61K 31/198* (2006.01)
(Continued)

(52) U.S. Cl.
CPC .......... *A61K 31/453* (2013.01); *A61K 31/198* (2013.01); *A61K 31/415* (2013.01);
(Continued)

(58) Field of Classification Search
CPC .............. A61K 2300/00; A61K 31/198; A61K 31/202; A61K 31/375; A61K 31/415;
(Continued)

(56) References Cited

U.S. PATENT DOCUMENTS 8,339,425 B2   12/2012  Shin et al.
2014/0323462 A1 * 10/2014 Ceccarelli ............... A61P 37/00
                                              514/210.01

FOREIGN PATENT DOCUMENTS

WO   WO-2013116713 A1 *  8/2013   ......... A61K 31/4468

OTHER PUBLICATIONS

Horti et al ( F-FNDP PET of soluble epoxide hydrolase, J Nucl Med. 2016;57: 1817-1822 (Year: 2016).*
(Continued)

*Primary Examiner* — Savitha M Rao
(74) *Attorney, Agent, or Firm* — Mintz, Levin, Cohn, Ferris, Glovsky and Popeo, P.C.

(57) ABSTRACT

Provided are methods of preventing, delaying, mitigating, reducing and/or inhibiting alpha-synuclein aggregates in the brains of a subject at risk of developing or suffering a cognitive disease associated with, caused and/or mediated at least in part by alpha-synuclein aggregates, for example, Parkinson's Disease or Dementia with Lewy Bodies (DLB).

9 Claims, 22 Drawing Sheets

Specification includes a Sequence Listing.

(51) Int. Cl.
| | |
|---|---|
| A61K 31/415 | (2006.01) |
| A61K 31/4525 | (2006.01) |
| A61K 31/454 | (2006.01) |
| A61K 31/4545 | (2006.01) |
| A61K 31/5377 | (2006.01) |
| A61K 45/06 | (2006.01) |
| A61P 25/28 | (2006.01) |
| C12N 15/113 | (2010.01) |

(52) U.S. Cl.
CPC ........ *A61K 31/4525* (2013.01); *A61K 31/454* (2013.01); *A61K 31/4545* (2013.01); *A61K 31/5377* (2013.01); *A61K 45/06* (2013.01); *A61P 25/28* (2018.01); *C12N 15/1137* (2013.01); *C12N 2310/14* (2013.01)

(58) Field of Classification Search
CPC .............. A61K 31/4525; A61K 31/453; A61K 31/454; A61K 31/4545; A61K 31/5377; A61K 31/7016; A61K 31/7088; A61K 45/06; A61P 25/28; C12N 15/1137; C12N 2310/14; C12Q 1/6883; C12Q 2600/158; G01N 2333/914; G01N 2800/2835; G01N 2800/50
See application file for complete search history.

(56) References Cited

OTHER PUBLICATIONS

Abou-Sleiman et al., Expanding insights of mitochondrial dysfunction in Parkinson's disease, Nature Review Neuroscience, Mar. 2006, vol. 7, pp. 207-219.
Ascherioet al, The epidemiology of Parkinson's disease: risk factors and prevention, The Lancet, Nov. 2016, vol. 15, pp. 1257-1272.
Beal, Mitochondria, Oxidative Damage, and Inflammation in Parkinson's Disease, Annals New York Academy of Sciences, 2003, vol. 991, pp. 120-131.
Bettaieb et al., Soluble Epoxide Hydrolase Deficiency or Inhibition Attenuates Diet-Induced Endoplasmic Reticulum Stress in Liver and Adipose Tissue, The Journal of Biological Chemistry, May 17, 2013, vol. 288, No. 20, pp. 14189-14199.
Bousquet et al., Impact of omega-3 fatty acids in Parkinson's disease, Ageing Research Review, 2011, vol. 10, pp. 453-463.
Campbell, New role for epoxyeicosatrienoic acids as anti-inflammatory mediators, TiPS, Apr. 2000, vol. 21, pp. 125-127.
Collino et al., Metabolic Signatures of Extreme Longevity in Northern Italian Centenarians Reveal a Complex Remodeling of Lipids, Amino Acids, and Gut Microbiota Metabolism, Plos One, Mar. 2013, vol. 8, Issue 3, pp. 1-12.
Cummings, Depression and Parkinson's Disease: A Review, The American Journal of Psychiatry, Apr. 1992, 149:4, pp. 443-454.
Dehay et al., Targeting α-synuclein for treating Parkinson's disease: mechanistic and therapeutic considerations, Lancet Neurol., Aug. 2015, 14:(8), pp. 855-866.
Dias et al., The role of oxidative stress in Parkinson's disease, J Parkinsons Dis. 2013, 3 (4):461-469.
Dickson, Neuropathology of Parkinson Disease, Parkinsonism Relat Disord, 2018, 46 (Suppl. 1):S30-S33.
Fujimori et al., Escape from pluripotency via inhibition of TGF-β/BMP and activation of Wnt Signaling Accelerates Differentiation and Aging in hPSC progeny cells, Stem Cell Reports, Nov. 4, 2017, vol. 9, pp. 1675-1691.
Goodarzi et al., Detecting depression in Parkinson disease: A systematic review and meta-analysis, Neurology, Jul. 26, 2016, 87:426-437.
Harris et al., Inhibition of soluble epoxide hydrolase attenuates hepatic fibrosis and endoplasmic reticulum stress induced by carbon tetrachloride in mice, Toxicol Appl Pharmacol, Jul. 15, 2015 286(2):102-111.
Harris et al., Soluble epoxides hydrolase: Gene structure, expression and deletion, Gene 2013, 526:61-74.
Hashimoto, Soluble epoxide hydrolase: a new therapeutic target for depression. Expert Opinion on Therapeutic Targets, 2016, vol. 20, No. 10, pp. 1149-1151.
Hirsch et al., Neuroinflammation in Parkinson's disease, Parkinsonism and Related Disorders, 2012, 1851 S210-S212.
Hirsch et al., Neuroinflammation in Parkinson's disease: a target for neuroprotection? Lancet Neurol 2009, 8:382-397.
Huang et al., Soluble Epoxide Hydrolase Inhibition Attenuates MPTP-induced in the Neurotoxicity in the Nigrostriatal Dopaminergic System: Involvement of a-synuclein aggregation and ER stress, Mol Neurobiol 2018,55:138-144, doi: 10.1007/s12035-017-0726-9.
Imaizumi et al., Mitochondrial dysfunction associated with increased oxidative stress and α-synuclein accumulation in PARK2 iPSC-derived neurons and postmortem brain tissue. Molecular Brain, 2012, 5:35.
Imaizumi et al., (2015) Controlling the Regional Identity of hPSC-derived Neurons to Uncover Neuronal Subtype Specificity of Neurological Disease Phenotypes, Stem Cell Reports, Dec. 8, 2015, vol. 5, pp. 1010-1022.
Imig et al., Soluble Epoxide Hydrolase as a Therapeutic Target for Cardiovascular Diseases, Nat Rev Drug Discov, 2009, 8:794-805.
Inceoglu et al., Endoplasmic reticulum stress in the peripheral nervous system is a significant driver of neuropathic pain, Proc Natl Acad Sci USA, Jul. 21, 2015, vol. 112, pp. 9082-9087.
Inceoglu et al., Modulation of mitochondrial dysfunction and endoplasmic reticulum stress are key mechanisms for the wide-ranging actions of epoxy fatty acids and soluble epoxide hydrolase inhibitors, Prostaglandins Other Lipid Mediat, Nov. 2017, 133:68-78.
Jenner, Oxidative stress in Parkinson's disease, Ann Neurol, 2003, 53: (Suppl. S3):S26-S38.
Joshi et al., Updates on immunity and inflammation in Parkinson disease pathology, J Neurosci Res., 2018, vol. 96, pp. 379-390.
Kalia et al., Parkinson's disease, The Lancet, Aug. 29, 2015, 386:896-912.
Kieburtz et al., New drugs for Parkinson's Disease: The Regulatory and Clinical Development Pathways in the United States, Movement Disorders, 2018, vol. 33, No. 6, pp. 920-927.
Kitada et al., Mutations in the parkin gene cause autosomal recessive juvenile parkinsonism, Nature, Apr. 1998, 392:605-608.
Kobayashi et al., Survival of corticostriatal neurons by Rho/Rho-kinase signaling pathway, Neuroscience Letters, 2016, 630:45-52.
Koike et al., The immunophilin ligand FK506 protects against methamphetamine-induced dopaminergic neurotoxicity in mouse striatum, Neuropharmacology, 2005, 48:391-397.
Lakkappa et al., Possible role of Epoxyeicosatrienoic acid in prevention of oxidative stress mediated neuroinflammation in Parkinson disorders, Med Hypotheses, Aug. 2016, 93:161-165.
Lei et al., Fatty acids and their therapeutic potential in neurological disorders, Neurochemistry International, 2016, 95:75-84.
López-Vicario et al., Inhibition of soluble epoxide hydrolase modulates inflammation and autophagy in obese adipose tissue and liver: role for omega-3 epoxides, Proc Natl Acad Sci USA, Jan. 13, 2015, vol. 112, No. 2, pp. 536-541.
Matsumoto et al., Functional Neurons Generated from T Cell-Derived Induced Pluripotent Stem Cells for Neurological Disease Modeling, Stem Cell Reports, Mar. 8, 2016, 6:422-435.
McGeer et al., Inflammation and neurodegeneration in Parkinson's disease, Parkinsonism and Related disorders, 2004, 10 (Suppl. 1):S3-S7.
Mercado et al., ER stress and Parkinson's disease: Pathological inputs that converge into the secretory pathway, Brain Research, 2016, 1648:626-632.
Morimoto et al., Homovanillic acid and 5-hydroxyindole acetic acid as biomarkers for dementia with Lewy bodies and coincident Alzheimer's disease: An autopsy-confirmed study, PLOS One, Feb. 6, 2017, 11 pages.
Morisseau et al., (2005) Epoxide Hydrolases:Mechanisms, Inhibitor Designs, and Biological Roles, Annu. Rev. Pharmacol. Toxicol., 2005, 45:311-333.

(56) References Cited

OTHER PUBLICATIONS

Morisseau et al., Impact of Soluble Epoxide Hydrolase and Epoxyeicosanoids on Human Health,. Annu. Rev. Pharmacol. Toxicol., 2013, 53:37-58.
Olanow et al., Targeting α-Synuclein as a Therapy for Parkinson's Disease: The Battle Begins, Movement disorders, 2017, 32:203-207.
Ostermann et al., Oral treatment of rodents with soluble epoxide hydrolase inhibitor 1-trifluoromethoxyphenyl-3-(1-propionylpiperidin-4-yl)urea (TPPU): bioavailability, resulting drug levels and modulation of oxylipin pattern, Prostaglandins Other Lipid Mediat, Sep. 2015, 121(0 0):131-137.
Paul et al., Cholesterol contributes to dopamine-neuronal loss in MPTP mouse model of Parkinson's disease: Involvement of mitochondrial dysfunctions and oxidative stress. PLoS One, Feb. 7, 2017, 12:e0171285.
Paxinos et al., The mouse brain in stereotaxic coordinates, 2001, $2^{nd}$ Edition, Academic Press.
Qin et al., Soluble Epoxide Hydrolase Deficiency or linhibition Attenuates MPTP-Induced Parkinsonism, Mol Neurobiol, 2015, 52:187-195.
Ren et al., 7,8-Dihydroxyflavone, a TrkB agonist, attenuates behavioral abnormalities and neurotoxicity in mice after administration of methamphetamine, Psychopharmacology, 2014, 231:159-166.
Ren et al., BDNF-TrkB signaling in the nucleus accumbens shell of mice has key role in methamphetamine withdrawal symptoms, Transl Psychiatry, 2015, 5:e666.
Ren et al., Gene deficiency and pharmacological inhibition of soluble epoxide hydrolase confers resilience to repeated social defeat stress, Proc Natl Acad Sci USA, Mar. 14, 2016, 113:E1944-E1952.
Rose et al., 1-Aryl-3-(1-acylpiperidin-4-yl)urea Inhibitors of Human and Murine Soluble Epoxide Hydrolase: Structure-Activity Relationships, Pharmacokinetics, and Reduction of Inflammatory Pain, J Med Chem, 2010, 53(19):7067-7075.
Saito et al., Accumulation of Phosphorylated α-Synuclein in Aging Human Brain, Journal of Neuropathology and Experimental Neurology, Jun. 2003, 62:644-654.
Schapira, (2008) Mitochondrial in the aetiology and pathogenesis of Parkinson's disease, Lancet Neurol, 2008, 7:97-109.
Schapira et al., Non-motor features of Parkinson disease, Nat Rev Neurosci, 2017, 18:435-450.
Seubert et al., Role of epoxyeicosatrienoic acids in protecting the myocardium following ischemia/reperfusion injury, Prostaglandins Other Lipid Mediat., 2007, 82(1-4):50-59.
Shimura et al., Familial Parkinson disease gene product, parkin, is a ubiquitin-protein ligase, Nature Genetics, Jul. 2000, 25:302-305.
Sinai et al., Targeted Disruption of Soluble Epoxide Hydrolase Reveals a Role in Blood Pressure Regulation, The Journal of Biological Chemistry, Dec. 22, 2000, vol. 275, No. 51,:40504-40510.
Spillantini et al., α-Synuclein in Lewy bodies, Nature, Aug. 28, 1997, 388:839-840.
Spillantini et al., α-Synuclein in filamentous inclusions of Lewy bodies from Parkinson's disease and dementia with Lewy bodies, Proc Natl Acad Sci USA, May 1998, 95:6469-6473.
Takahashi et al., Induction of Pluripotent Stem Cells from Adult Human Fibroblasts by Defined Factors, Cell, Nov. 30, 2007, 131:861-872.
Toulorge et al., Molecular changes in the postmortem parkinsonian brain, Journal of Neurochemistry, 2016, 139 (Suppl. 1):27-58.
Wagner et al., The role of long chain fatty acids and their epoxide metabolites in nociceptive signaling, Prostaglandins & Other Lipid Mediators, 2014, 113-115:2-12.
Wagner et al., Soluble Epoxide Hydrolase as a Therapeutic Target for Pain, Inflammatory and Neurodegenerative Diseases, Pharmacol Ther., Dec. 2017, 180:62-76.
Yang et al., Quantitative Profiling Method for Oxylipin Metabolome by Lliquid Chromatography Electrospray Ionization Tandem Mass Spectrometry, Anal Chem, Oct. 1, 2009, 81:8085-8093.
Horti et al., "F-FNDP for PET Imaging of Soluble Epoxide Hydrolase", J Nucl Med, 2016, vol. 57, pp. 1817-1822.
International Search Report for PCT/US2019/016717, mailed Jun. 20, 2019, 4 pages.
Wikipedia, "Parkinsonism" Nov. 16, 2017, 4 pages.
Written Opinion of the International Searching Authority for PCT/US2019/016717, mailed Jun. 20, 2019, 5 pages.

* cited by examiner

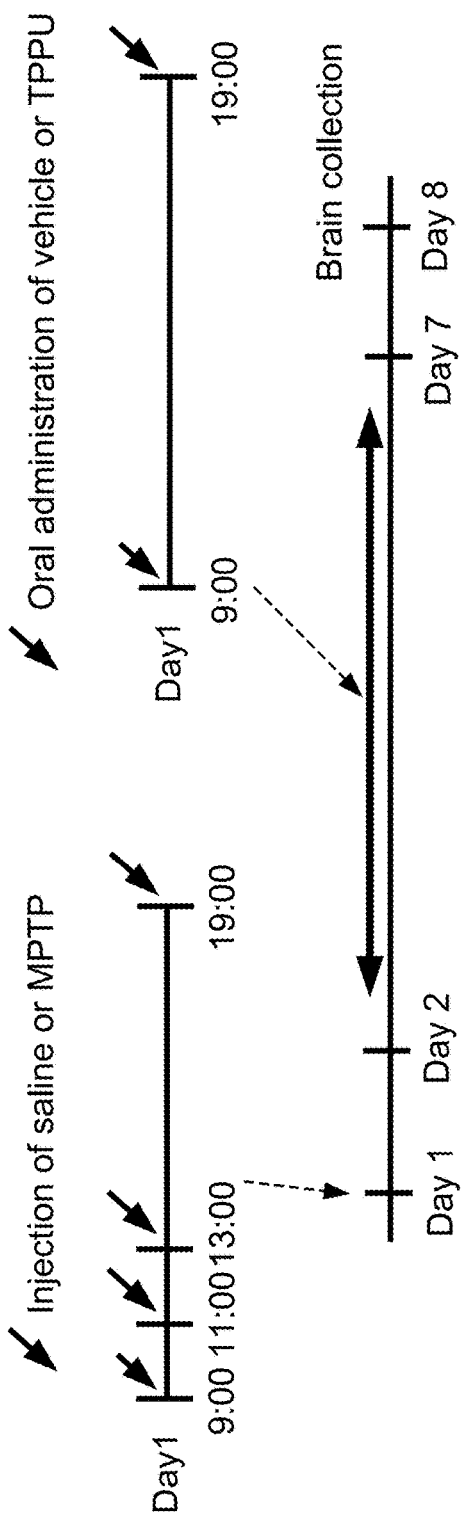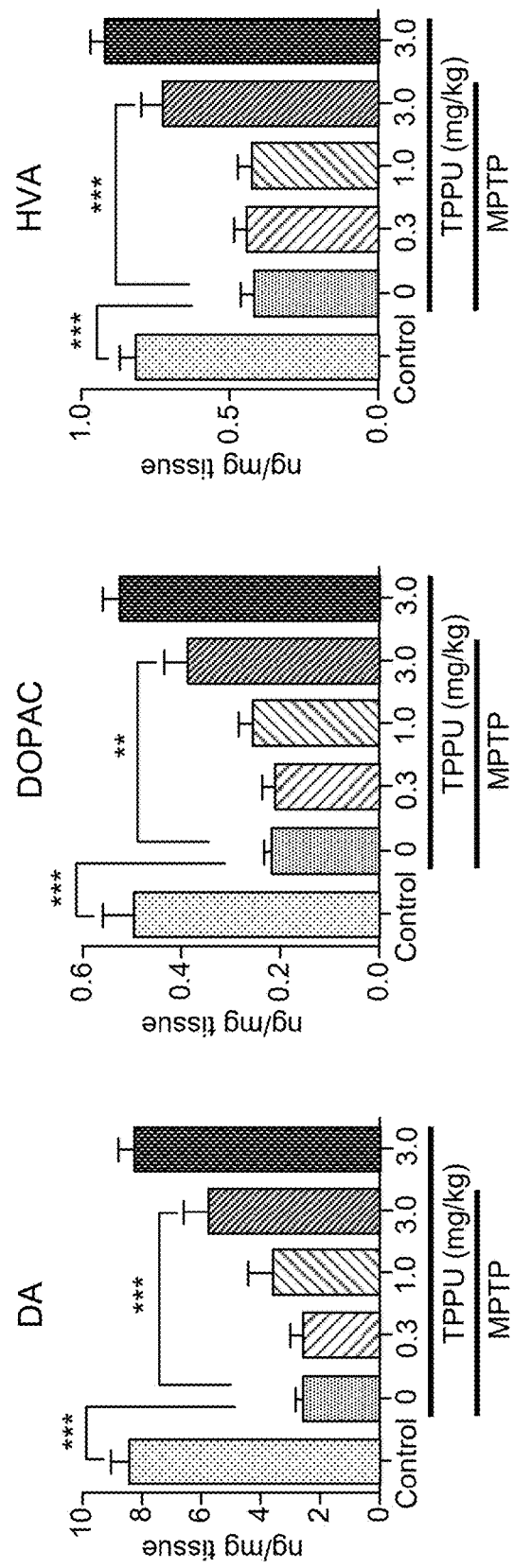
FIG. 2A
FIG. 2B
FIG. 2C
FIG. 2D

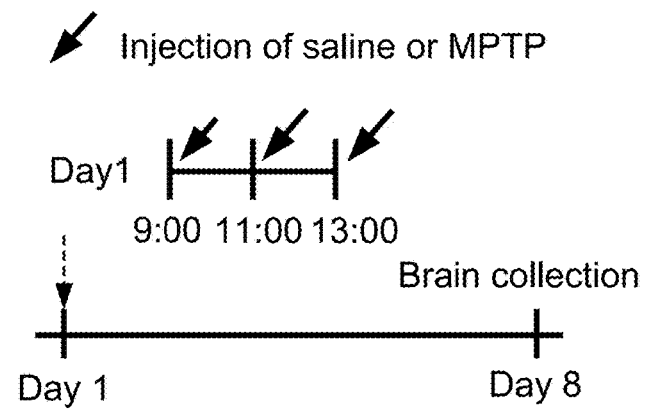
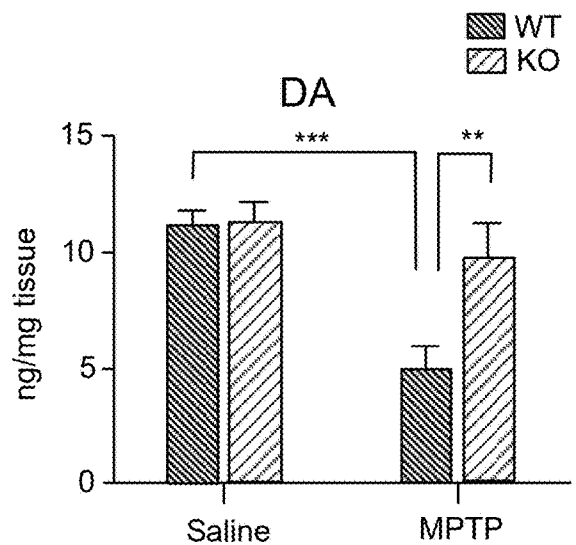
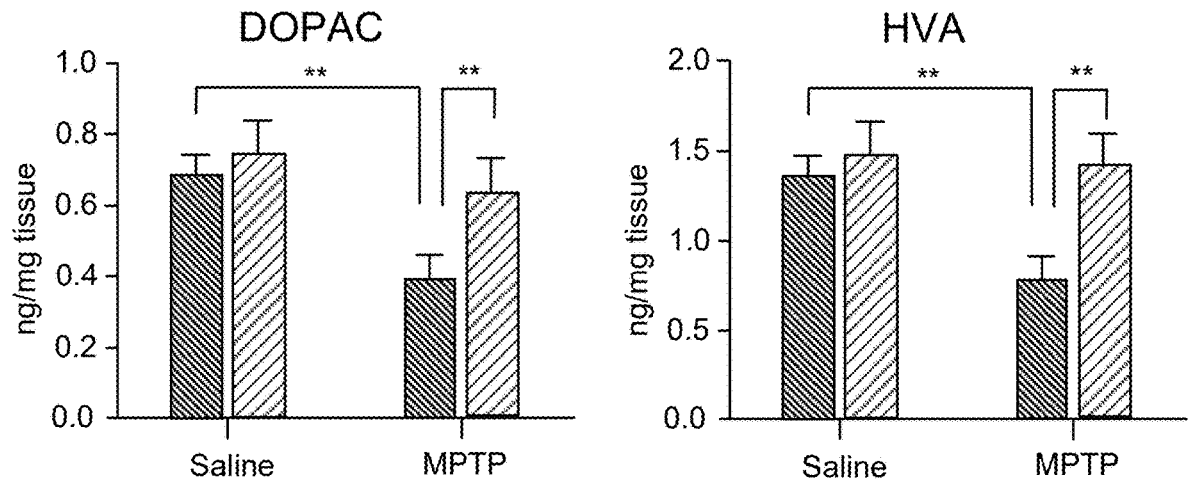
FIG. 3A
FIG. 3B
FIG. 3C
FIG. 3D

SEQUENCE LISTING

```
<160> NUMBER OF SEQ ID NOS: 37

<210> SEQ ID NO 1
<211> LENGTH: 554
<212> TYPE: PRT
<213> ORGANISM: Homo sapiens

<400> SEQUENCE: 1

Met Thr Leu Arg Gly Ala Val Phe Asp Leu Asp Gly Val Leu Ala Leu
1               5                   10                  15

Pro Ala Val Phe Gly Val Leu Gly Arg Thr Glu Glu Ala Leu Ala Leu
            20                  25                  30

Pro Arg Gly Leu Leu Asn Asp Ala Phe Gln Lys Gly Gly Pro Glu Gly
        35                  40                  45

Ala Thr Thr Arg Leu Met Lys Gly Glu Ile Thr Leu Ser Gln Trp Ile
    50                  55                  60

Pro Leu Met Glu Glu Asn Cys Arg Lys Cys Ser Glu Thr Ala Lys Val
65                  70                  75                  80

Cys Leu Pro Lys Asn Phe Ser Ile Lys Glu Ile Phe Asp Lys Ala Ile
                85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
    130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205
```

Ala Leu Lys Glu Leu Glu Lys Val Thr Gly Ile Gln Leu Leu Asn Thr
210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Trp Pro Ala Val Cys Leu Cys His Gly Phe Pro Glu Ser Trp Tyr Ser
                260                 265                 270

Trp Arg Tyr Gln Ile Pro Ala Leu Ala Gln Ala Gly Tyr Arg Val Leu
            275                 280                 285

Ala Met Asp Met Lys Gly Tyr Gly Glu Ser Ser Ala Pro Pro Glu Ile
290                 295                 300

Glu Glu Tyr Cys Met Glu Val Leu Cys Lys Glu Met Val Thr Phe Leu
305                 310                 315                 320

Asp Lys Leu Gly Leu Ser Gln Ala Val Phe Ile Gly His Asp Trp Gly
                325                 330                 335

Gly Met Leu Val Trp Tyr Met Ala Leu Phe Tyr Pro Glu Arg Val Arg
                340                 345                 350

Ala Val Ala Ser Leu Asn Thr Pro Phe Ile Pro Ala Asn Pro Asn Met
            355                 360                 365

Ser Pro Leu Glu Ser Ile Lys Ala Asn Pro Val Phe Asp Tyr Gln Leu
370                 375                 380

Tyr Phe Gln Glu Pro Gly Val Ala Glu Ala Glu Leu Glu Gln Asn Leu
385                 390                 395                 400

Ser Arg Thr Phe Lys Ser Leu Phe Arg Ala Ser Asp Glu Ser Val Leu
                405                 410                 415

Ser Met His Lys Val Cys Glu Ala Gly Gly Leu Phe Val Asn Ser Pro
            420                 425                 430

Glu Glu Pro Ser Leu Ser Arg Met Val Thr Glu Glu Ile Gln Phe
435                 440                 445

Tyr Val Gln Gln Phe Lys Lys Ser Gly Phe Arg Gly Pro Leu Asn Trp
450                 455                 460

Tyr Arg Asn Met Glu Arg Asn Trp Lys Trp Ala Cys Lys Ser Leu Gly
465                 470                 475                 480

Arg Lys Ile Leu Ile Pro Ala Leu Met Val Thr Ala Glu Lys Asp Phe
                485                 490                 495

Val Leu Val Pro Gln Met Ser Gln His Met Glu Asp Trp Ile Pro His
                500                 505                 510

Leu Lys Arg Gly His Ile Glu Asp Cys Gly His Trp Thr Gln Met Asp
            515                 520                 525

Lys Pro Thr Glu Val Asn Gln Ile Leu Ile Lys Trp Leu Asp Ser Asp
530                 535                 540

Ala Arg Asn Pro Pro Val Val Ser Lys Met
545                 550

<210> SEQ ID NO 2
<211> LENGTH: 2100
<212> TYPE: DNA
<213> ORGANISM: Homo sapiens

<400> SEQUENCE: 2
ggcacgagct ctctctctct ctctctctct ctctcgccgc catgacgctg cgcggcgccg    60
tcttcgacct tgacggggtg ctggcgctgc cagcggtgtt cggcgtcctc ggccgcacgg   120

```
aggaggccct ggcgctgccc agaggacttc tgaatgatgc tttccagaaa gggggaccag    180
agggtgccac tacccggctt atgaaaggag agatcacact ttcccagtgg ataccactca    240
tggaagaaaa ctgcaggaag tgctccgaga ccgctaaagt ctgcctcccc aagaatttct    300
ccataaaaga aatctttgac aaggcgattt cagccagaaa gatcaaccgc ccatgctcc     360 aggcagctct catgctcagg aagaaaggat tcactactgc catcctcacc aacacctggc    420
tggacgaccg tgctgagaga gatggcctgg cccagctgat gtgtgagctg aagatgcact    480
ttgacttcct gatagagtcg tgtcaggtgg gaatggtcaa acctgaacct cagatctaca    540
agtttctgct ggacaccctg aaggccagcc cagtgaggt cgttttttg gatgacatcg      600 gggctaatct gaagccagcc cgtgacttgg aatggtcac catcctggtc caggacactg     660
acacggccct gaaagaactg agaaagtga ccggaatcca gcttctcaat accccggccc     720
ctctgccgac ctcttgcaat ccaagtgaca tgagccatgg gtacgtgaca gtaaagccca    780
gggtccgtct gcattttgtg gagctgggct ggcctgctgt gtgcctctgc catggatttc    840
ccgagagttg gtattcttgg aggtaccaga tccctgctct ggcccaggca ggttaccggg    900
tcctagctat ggacatgaaa ggctatggag agtcatctgc cctcccgaa atagaagaat     960 attgcatgga agtgttatgt aaggagatgg taaccttcct ggataaactg gcctctctc    1020 aagcagtgtt cattggccat gactggggtg gcatgctggt gtggtacatg gctctcttct   1080
accccgagag agtgagggcg gtggccagtt tgaatactcc cttcatacca gcaaatccca   1140
acatgtcccc tttggagagt atcaaagcca acccagtatt tgattaccag ctctacttcc   1200
aagaaccagg agtggctgag gctgaactgg aacagaacct gagtcggact ttcaaaagcc   1260
tcttcagagc aagcgatgag agtgttttat ccatgcataa agtctgtgaa gcgggaggac   1320
tttttgtaaa tagcccagaa gagcccagcc tcagcaggat ggtcactgag gaggaaatcc   1380
agttctatgt gcagcagttc aagaagtctg gtttcagagg tcctctaaac tggtaccgaa   1440
acatggaaag gaactggaag tgggcttgca aaagcttggg acggaagatc ctgattccgg   1500
ccctgatggt cacggcggag aaggacttcg tgctcgttcc tcagatgtcc cagcacatgg   1560
aggactggat tccccacctg aaaaggggac acattgagga ctgtgggcac tggacacaga   1620
tggacaagcc aaccgaggtg aatcagatcc tcattaagtg gctggattct gatgcccgga   1680
acccaccggt ggtctcaaag atgtagaacg cagcgtagtg cccacgctca gcaggtgtgc   1740
catccttcca cctgctgggg caccattctt agtatacaga ggtggcctta cacacatctt   1800
gcatggatgg cagcattgtt ctgaaggggt ttgcagaaaa aaagattttt ctttacataa   1860
agtgaatcaa atttgacatt attttagatc ccagagaaat caggtgtgat tagttctcca   1920
ggcatgaatg catcgtccct ttatctgtaa gaacccttag tgtcctgtag ggggacagaa   1980
tggggtggcc aggtggtgat ttctctttga ccaatgcata gtttggcaga aaaatcagcc   2040
gttcatttag aagaatctta gcagagattg ggatgcctta ctcaataaag ctaagatgac   2100
```

<210> SEQ ID NO 3
<211> LENGTH: 23
<212> TYPE: DNA
<213> ORGANISM: Homo sapiens

<400> SEQUENCE: 3
cagtgttcat tggccatgac tgg                                             23

<210> SEQ ID NO 4
<211> LENGTH: 21

```
<212> TYPE: DNA
<213> ORGANISM: Homo sapiens

<400> SEQUENCE: 4
guguucauug gccaugacut t                                              21

<210> SEQ ID NO 5
<211> LENGTH: 21
<212> TYPE: DNA
<213> ORGANISM: Homo sapiens

<400> SEQUENCE: 5
agucauggcc aaugaacact t                                              21

<210> SEQ ID NO 6
<211> LENGTH: 23
<212> TYPE: DNA
<213> ORGANISM: Homo sapiens

<400> SEQUENCE: 6
gaaaggctat ggagagtcat ctg                                            23

<210> SEQ ID NO 7
<211> LENGTH: 21
<212> TYPE: DNA
<213> ORGANISM: Homo sapiens

<400> SEQUENCE: 7
aaggcuaugg agagucauct t                                              21

<210> SEQ ID NO 8
<211> LENGTH: 21
<212> TYPE: DNA
<213> ORGANISM: Homo sapiens

<400> SEQUENCE: 8
gaugacucuc cauagccuut t                                              21

<210> SEQ ID NO 9
<211> LENGTH: 23
<212> TYPE: DNA
<213> ORGANISM: Homo sapiens

<400> SEQUENCE: 9
aaaggctatg gagagtcatc tgc                                            23

<210> SEQ ID NO 10
<211> LENGTH: 21
<212> TYPE: DNA
<213> ORGANISM: Homo sapiens

<400> SEQUENCE: 10
aggcuaugga gagucaucut t                                              21

<210> SEQ ID NO 11
<211> LENGTH: 21
<212> TYPE: DNA
<213> ORGANISM: Homo sapiens

<400> SEQUENCE: 11
agaugacucu ccauagccut t                                              21

<210> SEQ ID NO 12
```

```
<211> LENGTH: 23
<212> TYPE: DNA
<213> ORGANISM: Homo sapiens

<400> SEQUENCE: 12
caagcagtgt tcattggcca tga                                          23

<210> SEQ ID NO 13
<211> LENGTH: 21
<212> TYPE: DNA
<213> ORGANISM: Homo sapiens

<400> SEQUENCE: 13
agcaguguuc auuggccaut t                                            21

<210> SEQ ID NO 14
<211> LENGTH: 21
<212> TYPE: DNA
<213> ORGANISM: Homo sapiens

<400> SEQUENCE: 14
auggccaaug aacacugcut t                                            21

<210> SEQ ID NO 15
<211> LENGTH: 23
<212> TYPE: DNA
<213> ORGANISM: Homo sapiens

<400> SEQUENCE: 15
cagcacatgg aggactggat tcc                                          23

<210> SEQ ID NO 16
<211> LENGTH: 21
<212> TYPE: DNA
<213> ORGANISM: Homo sapiens

<400> SEQUENCE: 16
gcacauggag gacuggauut t                                            21

<210> SEQ ID NO 17
<211> LENGTH: 21
<212> TYPE: DNA
<213> ORGANISM: Homo sapiens

<400> SEQUENCE: 17
aauccagucc uccaugugct t                                            21

<210> SEQ ID NO 18

<400> SEQUENCE: 18

000

<210> SEQ ID NO 19
<211> LENGTH: 23
<212> TYPE: DNA
<213> ORGANISM: Homo sapiens

<400> SEQUENCE: 19
cagtgttcat tggccatgac tgg                                          23

<210> SEQ ID NO 20
<211> LENGTH: 59
<212> TYPE: DNA
```

<213> ORGANISM: Homo sapiens

<400> SEQUENCE: 20
gatccccgtg ttcattggcc atgactttca agagaagtca tggccaatga acactttt       59

<210> SEQ ID NO 21
<211> LENGTH: 59
<212> TYPE: DNA
<213> ORGANISM: Homo sapiens

<400> SEQUENCE: 21
agctaaaaag tgttcattgg ccatgacttc tcttgaaagt catggccaat gaacacggg       59

<210> SEQ ID NO 22
<211> LENGTH: 23
<212> TYPE: DNA
<213> ORGANISM: Homo sapiens

<400> SEQUENCE: 22
gaaaggctat ggagagtcat ctg                                              23

<210> SEQ ID NO 23
<211> LENGTH: 59
<212> TYPE: DNA
<213> ORGANISM: Homo sapiens

<400> SEQUENCE: 23
gatccccaag gctatggaga gtcatcttca agagagatga ctctccatag cctttttt       59

<210> SEQ ID NO 24
<211> LENGTH: 59
<212> TYPE: DNA
<213> ORGANISM: Homo sapiens

<400> SEQUENCE: 24
agctaaaaaa aggctatgga gagtcatctc tcttgaagat gactctccat agccttggg      59

<210> SEQ ID NO 25
<211> LENGTH: 23
<212> TYPE: DNA
<213> ORGANISM: Homo sapiens

<400> SEQUENCE: 25
aaaggctatg gagagtcatc tgc                                              23

<210> SEQ ID NO 26
<211> LENGTH: 59
<212> TYPE: DNA
<213> ORGANISM: Homo sapiens

<400> SEQUENCE: 26
gatccccagg ctatggagag tcatctttca agagaagatg actctccata gccttttt       59

<210> SEQ ID NO 27
<211> LENGTH: 59
<212> TYPE: DNA
<213> ORGANISM: Homo sapiens

<400> SEQUENCE: 27
agctaaaaaa ggctatggag agtcatcatc tcttgaaaga tgactctcca tagcctggg      59

<210> SEQ ID NO 28
<211> LENGTH: 23

```
<212> TYPE: DNA
<213> ORGANISM: Homo sapiens

<400> SEQUENCE: 28
caagcagtgt tcattggcca tga                                          23

<210> SEQ ID NO 29
<211> LENGTH: 59
<212> TYPE: DNA
<213> ORGANISM: Homo sapiens

<400> SEQUENCE: 29
gatccccagc agtgttcatt ggccatttca agagaatggc caatgaacac tgcttttt    59

<210> SEQ ID NO 30
<211> LENGTH: 59
<212> TYPE: DNA
<213> ORGANISM: Homo sapiens

<400> SEQUENCE: 30
agctaaaaaa gcagtgttca ttggccattc tcttgaaatg gccaatgaac actgctggg   59

<210> SEQ ID NO 31
<211> LENGTH: 23
<212> TYPE: DNA
<213> ORGANISM: Homo sapiens

<400> SEQUENCE: 31
cagcacatgg aggactggat tcc                                          23

<210> SEQ ID NO 32
<211> LENGTH: 59
<212> TYPE: DNA
<213> ORGANISM: Homo sapiens

<400> SEQUENCE: 32
gatccccgca catggaggac tggattttca agagaaatcc agtcctccat gtgctttt    59

<210> SEQ ID NO 33
<211> LENGTH: 59
<212> TYPE: DNA
<213> ORGANISM: Homo sapiens

<400> SEQUENCE: 33
agctaaaaag cacatggagg actggatttc tcttgaaaat ccagtcctcc atgtgcggg   59

<210> SEQ ID NO 34
<211> LENGTH: 20
<212> TYPE: DNA
<213> ORGANISM: homo sapiens

<400> SEQUENCE: 34
acttcgtgct cgttcctcag                                              20

<210> SEQ ID NO 35
<211> LENGTH: 20
<212> TYPE: DNA
<213> ORGANISM: homo sapiens

<400> SEQUENCE: 35
agtgcccaca gtcctcaatg                                              20

<210> SEQ ID NO 36
```

```
<211> LENGTH: 20
<212> TYPE: DNA
<213> ORGANISM: homo sapiens

<400> SEQUENCE: 36
tgaagtgtga cgtggacatc                                              20

<210> SEQ ID NO 37
<211> LENGTH: 20
<212> TYPE: DNA
<213> ORGANISM: Homo sapiens

<400> SEQUENCE: 37
ggaggagcaa tgatcttgat                                              20
```

METHODS OF INHIBITING FORMATION OF ALPHA SYNUCLEIN AGGREGATES

CROSS-REFERENCES TO RELATED APPLICATIONS

This application is the U.S. National Stage Entry under § 371 of International Application No. PCT/US2019/016717, filed Feb. 5, 2019, which claims the benefit of priority to U.S. Provisional Application Ser. No. 62/626,685, filed Feb. 6, 2018, each of which is incorporated herein in its entirety by reference.

STATEMENT OF GOVERNMENTAL SUPPORT

This invention was made with government support under Grant No. R01 ES002710 awarded by the National Institutes of Health. The government has certain rights in the invention.

STATEMENT OF JOINT RESEARCH AGREEMENT

The subject matter and the claimed invention were made by or on behalf of The Regents of the University of California of Oakland, CA and Chiba University of Chiba, Japan, under a joint research agreement titled "JOINT RESEARCH AGREEMENT" The subject matter disclosed was developed and the claimed invention was made by, or on behalf of, one or more parties to the joint research agreement that was in effect on or before the effective filing date of the claimed invention, and the claimed invention was made as a result of activities undertaken within the scope of the joint research agreement.

REFERENCE TO A "SEQUENCE LISTING"

The present application contains a Sequence Listing, which is hereby incorporated by reference. The accompanying Sequence Listing is submitted in a file entitled "050759-518N01US_ST25," which was created on Jan. 2, 2025, and is approximately 16,384 bytes in size.

BACKGROUND

Parkinson's disease (PD) is the second most common neurodegenerative disease after Alzheimer's disease. Although the precise pathogenesis of PD is unknown, the pathological hallmark of PD involves the progressive loss of dopaminergic (DA) neurons in the substantia nigra (SN) pars compacta (SNpc) (1,2). In addition, the deposition of protein aggregates of α-synuclein, termed Lewy bodies, is evident in multiple brain regions of PD patients (3-6). Although there are many medications available to treat symptoms in PD patients, these do not block the progression of the disease, and, to date, no agent with a disease-modifying or neuroprotective indication for PD has been approved (7,8).

SUMMARY

In one aspect, provided are methods of mitigating in a subject one or more symptoms associated with a disease characterized by (e.g., associated with, caused and/or mediated at least in part by) alpha-synuclein (SNCA) aggregates or deposits in the brain, or delaying or preventing the onset of said symptoms. In some embodiments, the methods comprise: administering, or causing to be administered, to the subject an inhibitor of soluble epoxide hydrolase (sEHI) in an amount sufficient to mitigate said one or more symptoms. In some embodiments, the one or more symptoms are selected from the group consisting of bradykinesia, tremor, rigidity, postural instability and cognitive impairment.

In another aspect, provided are methods of reducing the risk, lessening the severity, or delaying the progression or onset of a disease characterized by alpha-synuclein (SNCA) aggregates or deposits in the brain of a subject. In some embodiments, the methods comprise: administering, or causing to be administered, to the subject an inhibitor of soluble epoxide hydrolase in an amount sufficient to reducing the risk, lessening the severity, or delaying the progression or onset of said disease.

With respect to embodiments of the methods of treatment, in some embodiments, the disease characterized by alpha synuclein aggregates or deposits is a neurodegenerative disease, e.g., selected from the group consisting of prodromal Parkinson's Disease, Parkinson's Disease, prodromal Dementia with Lewy Bodies (DLB), Dementia with Lewy Bodies (DLB), palsy, Pick's disease (frontal lobe dementia), and Alzheimer's Disease. In some embodiments, the mitigation comprises a reduction in the rate of alpha-synuclein aggregate or deposit formation in the brain of the subject. In some embodiments, the mitigation comprises a reduction in alpha-synuclein aggregate or deposit load in the brain of the subject. In some embodiments, the mitigation comprises an improvement in the cognitive and/or motor abilities of the subject. In some embodiments, the subject is a human. In some embodiments, the mitigation comprises a perceived improvement in quality of life by the human. In some embodiments, the subject is heterozygous or homozygous for a Parkinson's Disease associated mutation in one or more genes selected from the group consisting of alpha-synuclein (SNCA), leucine rich repeat kinase 2 (LRRK2), vacuolar protein sorting (VPS) retromer complex component (VPS35), parkin RBR E3 ubiquitin protein ligase (PRKN or PARK2), PTEN induced putative kinase 1 (PINK1) and glucocerebrosidase (GBA). In some embodiments, the subject has decreased expression of alpha-synuclein (SNCA) mRNA transcripts in circulating blood cells in comparison to a normal subject control. In some embodiments, the subject has decreased serum levels of heat shock protein family A (Hsp70) member 9 (HSPA9 or mortalin) in comparison to a normal subject control. In some embodiments, the subject has increased levels of monoamine oxidase B (MAOB), alpha-synuclein (SNCA) and/or soluble epoxide hydrolase (EPHX2) in lymphocytes, blood, serum or cerebrospinal fluid (CSF) in comparison to a normal subject control. In some embodiments, the blood alpha-synuclein (SNCA) of the subject has altered post-translational modifications, e.g., one or more of increased Y125 phosphorylation, increased Y39 nitration, and decreased SUMOylation, in comparison to a normal control subject. In some embodiments, the subject has decreased cerebrospinal fluid (CSF) levels of one or more biomarkers selected from the group consisting of Aβ1-42, T-tau, P-tau181, α-synuclein, and T-tau/AP1-42 in comparison to a normal control. In some embodiments, the subject has detectable nigrostriatal dopaminergic denervation, e.g., as detectable by single photon emission computed tomography (SPECT) or decarboxylase activity with 18F-Dopa positron emission tomography (PET). In some embodiments, the subject has decreased radiotracer binding using striatal dopamine transporters (DAT)/single photon emission computed tomography (SPECT) imaging. In some embodiments, the subject demonstrates subtle motor impairment. In some embodiments, the subject demonstrates mild cognitive impairment (MCI). In some embodiments, the subject demonstrates hyposmia, e.g., has failed an olfactory challenge test. In some embodiments, the subject suffers depression and/or anxiety. In some embodiments, the sEHI is administered via a route selected from the group consisting of orally, intrathecally, intraspinally, intravenously, subcutaneously, transdermally, intrapulmonary, inhalationally, intramuscularly and rectally. In some embodiments, the sEHI is formulated for administration via a route selected from the group consisting of oral administration, intrathecal delivery, intraspinal delivery, isophoretic delivery, transdermal delivery, aerosol administration, administration via inhalation, intravenous administration, intramuscular administration and rectal administration. In some embodiments, the administering is over a period of at least three weeks, e.g., over a period of at least 1, 2, 3, 4, 5, 6 months, or 1, 2, 3, 4, 5 years, or until the end of the subject's lifetime. In some embodiments, the sEHI is administered in conjunction with or concurrently with one or more agents selected from the group consisting of an inhibitor of cyclooxygenase-2 (COX-2), and inhibitor of phosphodiesterase, and mixtures thereof. In some embodiments, the sEHI is administered in conjunction with an agent selected from the group consisting of inhibitor of endoplasmic reticulum (ER) stress, carbidopa/levodopa, dopamine agonists, and monoamine oxidase type B (MAO-B) inhibitors, and mixtures thereof. In some embodiments, the inhibitor of ER stress is selected from the group consisting of group consisting of 4-phenyl butyric acid (4-PBA), 3-phenylpropionic acid (3-PPA), 5-phenylvaleric acid (5-PVA), 6 phenylhexanoic acid (6-PHA), butyrate, tauroursodeoxycholic acid, trehalose, deuterated water, docosahexaenoic acid ("DHA"), eicosapentaenoic acid ("EPA"), vitamin C, arabitol, mannose, glycerol, betaine, sarcosine, trimethylamine-N oxide, DMSO and mixtures thereof. In some embodiments, an efficacious amount of the sEHI crosses the blood-brain barrier. In some embodiments, the sEHI comprises a primary or central pharmacophore selected from the group consisting of a urea, a carbamate, and an amide, or these functionalities in a nitrogen heterocycle. In some embodiments, the sEHI comprises a primary or central pharmacophore that comprises a piperidin-4-yl urea. In some embodiments, the sEHI does not comprise 1-trifluoromethoxyphenyl-3-(1-propionylpiperidin-4-yl) urea (TPPU). In some embodiments, the sEHI is selected from the group consisting of 1-(3-fluoro-4-(trifluoromethoxy)phenyl)-3-(1-(tetrahydro-2H-pyran-4-carbo-nyl) piperidin-4-yl)urea (Compound 29 of Table 3) and 1-trifluoromethoxyphenyl-3-(1-propionylpiperidin-4-yl) urea (TPPU). In some embodiments, the sEHI does not comprise one or both of an adamantyl moiety or an azetidine moiety. In some embodiments, the sEHI comprises a dual inhibitor of sEH and COX-2. In some embodiments, a dual inhibitor of sEH and COX-2 is administered as the sole active agent. In some embodiments, the dual inhibitor of sEH and COX-2 is 4-(5-phenyl-3-{3-[3-(4-trifluoromethyl-phenyl)-ureido]-propyl}-pyrazol-1-yl)-benzenesulfonamide (PTUPB). In some embodiments, the dual inhibitor of sEH and COX 2 is a compound in Table 4 selected from the group consisting of:

compound 1860 (1-Adamantan-1-yl-3-[1-(4-methanesulfonyl-phenyl)-5-phenyl-1H-pyrazol-3-ylmethyl]-urea), compound 2321 (1-Cycloheptyl-3-[1-(4-methanesulfonyl-phenyl)-5-phenyl-1H-pyrazol-3-ylmethyl]-urea), compound 2322 (1-[1-(4-Methanesulfonyl-phenyl)-5-phenyl-1H-pyrazol-3-ylmethyl]-3-phenyl-urea), compound 2323 (1-[1-(4-Methanesulfonyl-phenyl)-5-phenyl-1H-pyrazol-3-ylmethyl]-3-(4-trifluoromethoxy-phenyl)-urea), compound 2324 (1-[1-(4-Methanesulfonyl-phenyl)-5-phenyl-1H-pyrazol-3-ylmethyl]-3-(4-trifluoromethyl-phenyl)-urea), compound 1861 (1-[1-(4-Methanesulfonyl-phenyl)-5-phenyl-1H-pyrazol-3-ylmethyl]-3-(3-trifluoromethyl-phenyl)-urea), compound 2107 (4-{5-Phenyl-3-[3-(3-trifluoromethyl-phenyl)-ureidomethyl]-pyrazol-1-yl}-benzenesulfonamide), compound 2106 (1-[5-tert-Butyl-1-(4-methanesulfonyl-phenyl)-1H-pyrazol-3-ylmethyl]-3-(4-trifluoromethyl-phenyl)-urea), compound 2121 (4-{5-Phenyl-3-[3-(3-trifluoromethyl-phenyl)-ureido]-pyrazol-1-yl}-benzenesulfonamide), compound 2313 (4-(5-Phenyl-3-{2-[3-(3-trifluoromethyl-phenyl)-ureido]-ethyl}-pyrazol-1-yl)-benzenesulfonamide), compound 1862 (1-{3-[1-(4-Methanesulfonyl-phenyl)-5-phenyl-1H-pyrazol-3-yl]-propyl}-3-(3-trifluoromethyl-phenyl)-urea), compound 2246 (4-(5-Phenyl-3-{3-[3-(3-trifluoromethyl-phenyl)-ureido]-propyl}-pyrazol-1-yl)-benzenesulfonamide), compound 2152 (4-(5-p-Tolyl-3-{3-[3-(3-trifluoromethyl-phenyl)-ureido]-propyl}-pyrazol-1-yl)-benzenesulfonamide), compound 2325 (4-(3-{3-[3-(2,6-Diisopropyl-phenyl)-ureido]-propyl}-5-phenyl-pyrazol-1-yl)-benzenesulfonamide), compound 2245 (4-{5-Phenyl-3-[3-(3-phenyl-ureido)-propyl]-pyrazol-1-yl}-benzenesulfonamide), compound 2326 (4-{3-[3-(3-Adamantan-1-yl-ureido)-propyl]-5-phenyl-pyrazol-1-yl}-benzenesulfonamide), compound 2247 (4-{3-[3-(3-Cycloheptyl-ureido)-propyl]-5-phenyl-pyrazol-1-yl}-benzenesulfonamide), compound 2327 (4-(3-{3-[3-(4-Chloro-phenyl)-ureido]-propyl}-5-phenyl-pyrazol-1-yl)-benzenesulfonamide), compound 2328 (4-(5-Phenyl-3-{3-[3-(4-trifluoromethyl-phenyl)-ureido]-propyl}-pyrazol-1-yl)-benzenesulfonamide); and compound 2329 (4-(5-Phenyl-3-{3-[3-(4-trifluoromethoxy-phenyl)-ureido]-propyl}-pyrazol-1-yl)-benzenesulfonamide). In some embodiments, the sEHI comprises a dual inhibitor of phosphodiesterase 4 (PDE4) and sEH. In some embodiments, a dual inhibitor of sEH and PDE4 is administered as the sole active agent. In some embodiments, the dual inhibitor of PDE4 and sEH is a compound in Table 5 selected from the group consisting of:

compound 1; 3-(Cyclopentyloxy)-4-methoxy-N-(4-methoxy-2-(trifluoromethyl)benzyl)benzamide;

compound 2; 3-(Cyclopentyloxy)-4-methoxy-N-(2-(trifluoromethyl)benzyl)benzamide;

compound 3; 3-(Cyclopentyloxy)-4-methoxy-N-(2-methyl-benzyl)benzamide;

compound 4; N-(4-Methoxy-2-(trifluoromethyl)benzyl)benzamide;

compound 5; 4-Fluoro-N-(4-methoxy-2-(trifluoromethyl) benzyl)benzamide;

compound 6; 3-Acetamido-N-(4-methoxy-2-(trifluoromethyl)benzyl)benzamide;

compound 7; N-(4-Methoxy-2-(trifluoromethyl)benzyl)-3-propionamidobenzamide;

compound 8; 3-Acetamido-N-(4-methoxy-2-(trifluoromethyl)benzyl)-4-methylbenzamide;

compound 9; N-(4-Methoxy-2-(trifluoromethyl)benzyl)-2-oxoindoline-6-carboxamide;
compound 10; 4-Acetamido-N-(4-methoxy-2-(trifluoromethyl)benzyl)benzamide;
compound 11; 4-Methoxy-N-(4-methoxy-2-(trifluoromethyl)benzyl)benzamide;
compound 14; 4-(Difluoromethoxy)-N-(4-methoxy-2-(trifluoromethyl)benzyl)benzamide;
compound 19; 3-(Cyclopentyloxy)-N-(4-methoxy-2-(trifluoromethyl)benzyl)benzamide;
compound 20; 3-(Cyclopentyloxy)-4-fluoro-N-(4-methoxy-2-(trifluoromethyl)benzyl)benzamide;
compound 21; tert-Butyl 4-((4-methoxy-2-(trifluoromethyl)benzyl)carbamoyl)piperidine-1-carboxylate;
compound 22; N-(4-Methoxy-2-(trifluoromethyl)benzyl)piperidine-4-carboxamide;
compound 23; N-(4-methoxy-2-(trifluoromethyl)benzyl)-1-propionylpiperidine-4-carboxamide (MPPA);
compound 24; 1-Butyryl-N-(4-methoxy-2-(trifluoromethyl)benzyl)piperidine-4-carboxamide;
compound 25; N-(4-Methoxy-2-(trifluoromethyl)benzyl)-1-(2-methylbutanoyl)piperidine-4-carboxamide;
compound 26; 1-Ethyl-N-(4-methoxy-2-(trifluoromethyl)benzyl)piperidine-4-carboxamide; and
compound 27; N-(4-Methoxy-2-(trifluoromethyl)benzyl)-1-propylpiperidine-4-carboxamide.

In a further aspect, provided are methods of identifying a subject at risk for Parkinson's disease, the method comprising: determining a level of expression and/or activity of soluble epoxide hydrolase (EPHX2) in the subject or in a sample from the subject wherein an elevated level of EPHX2 expression and/or activity as compared to a control is an indicator that the subject has an increased likelihood of developing Parkinson's disease. In some embodiments, the subject is asymptomatic for Parkinson's disease. In some embodiments, the subject presents with no significant neuronal cell loss. In some embodiments, the subject is a human. In some embodiments, the human presents without symptoms of Parkinson's disease, but is believed to be at risk for the disease. In some embodiments, the subject is heterozygous or homozygous for a Parkinson's Disease associated mutation in one or more genes selected from the group consisting of alpha-synuclein (SNCA), leucine rich repeat kinase 2 (LRRK2), vacuolar protein sorting (VPS) retromer complex component (VPS35), parkin RBR E3 ubiquitin protein ligase (PRKN or PARK2), PTEN induced putative kinase 1 (PINK1) and glucocerebrosidase (GBA). In some embodiments, the subject has decreased expression of alpha-synuclein (SNCA) mRNA transcripts in circulating blood cells in comparison to a normal subject control. In some embodiments, the subject has decreased serum levels of heat shock protein family A (Hsp70) member 9 (HSPA9 or mortalin) in comparison to a normal subject control. In some embodiments, the subject has increased levels of monoamine oxidase B (MAOB), alpha-synuclein (SNCA) and/or soluble epoxide hydrolase (EPHX2) in blood, serum or cerebrospinal fluid (CSF) in comparison to a normal subject control. In some embodiments, the blood alpha-synuclein (SNCA) of the subject has altered post-translational modifications, e.g., one or more of increased Y125 phosphorylation, increased Y39 nitration, and decreased SUMOylation, in comparison to a normal control subject. In some embodiments, the subject has decreased cerebrospinal fluid (CSF) levels of one or more biomarkers selected from the group consisting of Aβ1-42, T-tau, P-tau181, α-synuclein, and T-tau/Aβ1-42 in comparison to a normal control.

In some embodiments, the subject has detectable nigrostriatal dopaminergic denervation, e.g., as detectable by single photon emission computed tomography (SPECT) or decarboxylase activity with 18F-Dopa positron emission tomography (PET). In some embodiments, the subject has decreased radiotracer binding using striatal dopamine transporters (DAT)/single photon emission computed tomography (SPECT) imaging. IN some embodiments, the subject demonstrates subtle motor and/or mild cognitive impairment. In some embodiments, the subject demonstrates hyposmia, e.g., has failed an olfactory challenge test. In some embodiments, the subject suffers depression and/or anxiety. In some embodiments, the sample comprises one or more biological materials selected from the group consisting of blood or a blood fraction, platelets, saliva, cerebrospinal fluid, and a tissue sample. In some embodiments, the control comprises an expression and/or activity level determined for a population of the subject that does not develop Parkinson's disease. In some embodiments, the control comprises a threshold value designated as indicative of increased risk for Parkinson's disease. In some embodiments, the control is the level of EPHX2 expression and/or activity in the same subject at an earlier time in the subject's life.

Definitions

Units, prefixes, and symbols are denoted in their Systéme International d'Unités (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 epoxygenases. As discussed further in a separate section below, while the use of unmodified EETs can be used, derivatives of EETs, such as amides and esters (both natural and synthetic), EETs analogs, and EETs optical isomers and corresponding EPA and DHA derivatives, including omega-3-derived epoxides epoxyeicosatetraenoic acids (EEQs) and epoxydocosapentaenoic acids (EDPs), can all be used in the methods, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH"; EC 3.3.2.10) is an epoxide hydrolase which in cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. In some embodiments, the inhibitor does not also inhibit the activity of microsomal epoxide hydrolase by more than 25% at concentrations at which the inhibitor inhibits sEH by at least 50%, e.g., does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS— (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the 0-3 homolog of 14(15)-EpETrE ("14(15)EET") derived via epoxidation of the 14,15-double bond of arachidonic acid.

"$IC_{50}$" refers to the concentration of an agent required to inhibit enzyme activity by 50%.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm *C. elegans* in the early 1990s and are now known in many species, including humans. As used herein, it refers to exogenously administered miRNA unless specifically noted or otherwise required by context.

The term "therapeutically effective amount" refers to that amount of the compound being administered sufficient to prevent or decrease the development of one or more of the symptoms of the disease, condition or disorder being treated (e.g., fibrosis and/or inflammation).

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-inflammatory, and/or anti-fibrotic effects), or that quantitatively is less than the established therapeutic dose for that particular pharmacological agent (e.g., as published in a reference consulted by a person of skill, for example, doses for a pharmacological agent published in the Physicians' Desk Reference, 71st Ed., 2017, PDR Network or Brunton, et al., Goodman & Gilman's The Pharmacological Basis of Therapeutics, 13th edition, 2017, McGraw-Hill). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, 22nd Ed., Pharmaceutical Press (2012).

The terms "sustained release" and "extended release" are used in their conventional sense to refer to a drug formulation that provides for gradual release of a drug over an extended period of time, for example, 12 hours or more, and that e.g., results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

The terms "systemic administration" and "systemically administered" refer to a method of administering sEHI; optionally co-administered with a second agent (e.g., inhibitor of ER stress, carbidopa/levodopa, dopamine agonists, and monoamine oxidase type B (MAO-B) inhibitors) to a subject so that the agent/cells is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administration" refers to the presence of both active agents/cells in the blood or body at the same time. Active agents that are co-administered can be delivered concurrently (i.e., at the same time) or sequentially.

The phrase "in conjunction with" when used in reference to the use of the active agent(s) described herein (e.g., an inhibitor of sEH) in conjunction with one or more other drugs described herein (e.g., an inhibitor of cyclooxygenase-2, an inhibitor of phosphodiesterase, inhibitor of ER stress, carbidopa/levodopa, dopamine agonists, monoamine oxidase type B (MAO-B) inhibitors) the active agent(s) and the other drug(s) are administered so that there is at least some chronological overlap in their physiological activity on the organism. When they are not administered in conjunction with each other, there is no chronological overlap in physiological activity on the subject. In certain embodiments, the "other drug(s)" are not administered at all (e.g., not co-administered) to the subject.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The terms "patient," "subject" or "individual" interchangeably refers to a human or non-human mammal, including primates (e.g., macaque, pan troglodyte, pongo, bonobo, gorilla), a domesticated mammal (e.g., felines, canines), an agricultural mammal (e.g., bovine, ovine, porcine, equine) and a laboratory mammal or rodent (e.g., rattus, murine, lagomorpha, hamster).

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "inhibiting," "reducing," "decreasing" refers to inhibiting the disease condition of interest (e.g., disease associated with, caused and/or mediated at least in part by alpha-synuclein aggregrates, e.g. Lewy Body dementias, e.g., Parkinson's disease, dementia with Lewy Bodies, palsy) in a mammalian subject by a measurable amount using any method known in the art. For example, one or more symptoms of a disease associated with, caused and/or mediated at least in part by alpha-synuclein aggregrates is inhibited, reduced or decreased if an indicator of the disease is reduced by a measureable amount, either quantitatively or qualitatively, e.g., in comparison to the same disease indicator prior to administration of an sEHI. Qualitative and quantitative measures of disease associated with, caused and/or mediated at least in part by alpha-synuclein aggregrates are known in the art, including various nonmotor features that predate the motor manifestations of Parkinson's disease, e.g., sleep abnormalities, neurobehavioral symptoms, and olfactory dysfunction; cerebrospinal fluid and serum tests, including α-synuclein and Parkinsonism associated deglycase (DJ-1, PARK7); and various imaging modalities e.g., transcranial Doppler ultrasonography, radiolabeled tracer imaging, and magnetic resonance imaging. See, e.g., Chahine, et al., *Curr Opin Neurol.* (2011) 24(4): 309-17. Symptoms for patients with a neurodegenerative disorder associated with, caused and/or mediated at least in part by alpha-synuclein aggregates or deposits, e.g., bradykinesia, tremor, rigidity, postural instability and cognitive impairment, can be measured and quantified using appropriate tests and scales established in the art.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than the listed active agents, e.g., the sEHI and/or an a secondary agent (e.g., COX-1 inhibitor, PDE4 inhibitor, inhibitor of ER stress, carbidopa/levodopa, dopamine agonists, and monoamine oxidase type B (MAO-B) inhibitors).

BRIEF DESCRIPTION OF THE DRAWINGS

FIGS. 1A-E illustrate the effects of MPTP-induced neurotoxicity in the mouse brain. (A): Schedule of treatment and brain collection. (B-D): MPTP (10 mg/kg×3, 2-hr interval, IP, 9:00, 11:00, and 13:00) or saline was administered into mice. On day 8, mice were perfused for immunohistochemistry of DAT and TH. (B): Typical immunohistochemistry of DAT in the striatum. One-way ANOVA revealed the results ($F_{3,17}$=30.29, P<0.001). (C): Typical immunohistochemistry of TH in the striatum. One-way ANOVA revealed the results ($F_{3,17}$=31.63, P<0.001). (D): Typical immunohistochemistry of TH in the SN. One-way ANOVA revealed the results ($F_{3,17}$=21.07, P<0.001). Data are shown as mean S.E.M. (n=5 or 6). ***P<0.001 compared to control group.

FIGS. 2A-J illustrate the effects of TPPU on MPTP-induced neurotoxicity in the mouse brain. (A): Schedule of treatment and brain collection. (B-D): Pretreatment with TPPU (0.3, 1.0, or 3.0 mg/kg, PO) attenuated reductions of DA and its metabolites (DOPAC and HVA) in the striatum after repeated administration of MPTP (10 mg/kg×3, 2-hr interval, IP), in a dose dependent manner. Data are shown as mean f S.E.M. (n=7 or 8). P<0.01, *P<0.001 compared to vehicle+MPTP group (one-way ANOVA, DA: F5,41=19.01, P<0.001; DOPAC: F5,41=13.94, P<0.001; HVA: F5,41=18.74, P<0.001). (E, F): Typical immunohistochemistry of DAT and TH in the striatum. (G, H): Two-way ANOVA revealed the results; in the bar graphs displayed, each pair of columns (for specific conditions tested, e.g., saline, MPTP) reports vehicle on the left and TPPU on the right (DAT, MPTP: $F_{1,20}$=12.65, P=0.002, TPPU: $F_{1,20}$=2.846, P=0.107; interaction: $F_{1,20}$=11.18, P=0.003), and (TH, MPTP: $F_{1,20}$=26.57, P<0.001, TPPU: $F_{1,20}$=29.76, P<0.001, interaction: $F_{1,20}$=13.12, P=0.0017). Data are shown as mean±S.E.M. (n=6). P<0.01, *P<0.001 compared to control group. (1): Typical immunofluorescence of TH-positive cells in the SN. (J): Two-way ANOVA revealed the results; in the bar graphs diplayed, each pair of columns (for specific conditions tested, e.g., saline, MPTP) reports vehicle on the left and TPPU on the right (TH, MPTP: $F_{1,20}$=17.46, P=0.0005, TPPU: $F_{1,20}$=4.274, P=0.052; interaction: $F_{1,20}$=14.92, P=0.001). Data are shown as mean±S.E.M. (n=6). ***P<0.001 compared to control group.

FIGS. 3A-L illustrate lack of MPTP-induced neurotoxicity in the sEH KO mice. (A): Schedule of treatment, and brain collection. (B-D): Repeated administration of MPTP (10 mg/kg×3, 2-hr interval, IP) did not decrease tissue levels of DA, DOPAC, and HVA in the striatum. Two-way ANOVA revealed the results; in the bar graphs diplayed, each pair of columns (for specific conditions tested, e.g., saline, MPTP) reports WT on the left and KO on the right (DA, MPTP: $F_{1,28}$=14.52, P=0.0007, KO: $F_{1,28}$=6.096, P=0.0199; interaction: $F_{1,28}$=4.837, P=0.0363), (DOPAC, MPTP: $F_{1,28}$=7.822, P=0.0092, KO: $F_{1,28}$=4.189, P=0.0502; interaction: $F_{1,28}$=4.980, P=0.0338), (HVA, MPTP: $F_{1,28}$=3.753, P=0.0637, KO: $F_{1,28}$=7.985, P=0.0089; interaction: $F_{1,28}$=5.174, P=0.0314). Data are shown as mean±S.E.M. (n=8). P<0.01, *P<0.001 compared to vehicle+MPTP group. (E, F): Typical immunohistochemistry of DAT and TH in the striatum. (G, H): Two-way ANOVA revealed the results; in the bar graphs diplayed, each pair of columns (for specific conditions tested, e.g., saline, MPTP) reports WT on the left and KO on the right (DAT, MPTP: $F_{1,28}$=6.692, P=0.0154, KO: $F_{1,28}$=19.47, P=0.0001; interaction: $F_{1,28}$=4.788, P=0.0375), and (TH, MPTP: $F_{1,28}$=37.38, P<0.0001, KO: $F_{1,28}$=2.322, P=0.1387; interaction: $F_{1,28}$=15.57, P=0.0005). Data are shown as mean f S.E.M. (n=8). P<0.01, *P<0.001 compared to control group. (I): Typical immunofluorescence of TH-positive cells in the SN. (J): Two-way ANOVA revealed the results; in the bar graph diplayed, each pair of columns (for specific conditions tested, e.g., saline, MPTP) reports WT on the left and KO on the right (TH, MPTP: $F_{1,28}$=22.69, P<0.0001, KO: $F_{1,28}$=18.23, P=0.0002; interaction: $F_{1,28}$=13.41, P=0.0010). Data are shown as mean±S.E.M. (n=8). *P<0.001 compared to control group (post-hoc Tukey test). (K): Schematic of AAV-mediated Ephx2 expression in the striatum. The diagram shows the AAV constructs and stereotaxic injection of AAV into the striatum. (L): Typical immunohistochemistry of DAT in the mouse striatum. Two-way ANOVA revealed the results (MPTP: $F_{1,20}$=17.80, P=0.0004, KO: $F_{1,20}$=4.890, P=0.0388; interaction: $F_{1,20}$=9.378, P=0.0061). Data are shown as mean f S.E.M. (n=6). P<0.001 compared to control group.

DETAILED DESCRIPTION

1. Introduction

Figure 1A:
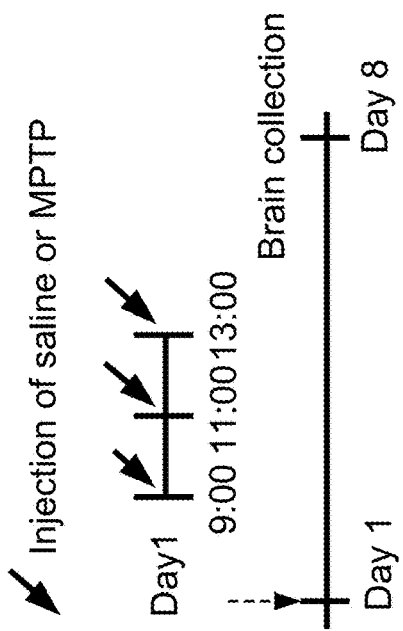

Lewy body dementias, including Parkinson's disease (PD) and dementia with Lewy bodies (DLB), are characterized as a chronic and progressive neurodegenerative disorder, and the deposition of specific protein aggregates of α-synuclein, termed Lewy bodies. Lewy bodies are evident in multiple brain regions of PD patients. Although there are several available medications to treat PD symptoms, these medications do not stop the progression of the disease. Soluble epoxide hydrolase (sEH) plays a role in inflammation associated with the pathogenesis of PD. Here we found that MPTP (1-methyl-4-phenyl-1,2,3,6-tetrahydropyridine)-induced neurotoxicity in the mouse striatum was attenuated by subsequent repeated administration of TPPU, a potent sEH inhibitor. Furthermore, deletion of the sEH gene protected against MPTP-induced neurotoxicity, while the overexpression of sEH in the striatum significantly enhanced MPTP-induced neurotoxicity. Moreover, the expression of the sEH protein in the striatum from MPTP-treated mice or postmortem brain samples from patients with dementia of Lewy bodies was significantly higher compared with control groups. Interestingly, there was a positive correlation between sEH expression and phosphorylation of α-synuclein in the striatum. Oxylipin analysis showed decreased levels of 8,9-epoxy-5Z, llZ,14Z-eicosatrienoic acid in the striatum of MPTP-treated mice, suggesting increased activity of sEH in this region. Interestingly, the expression of sEH mRNA in human PARK2 iPSC-derived neurons was higher than that of healthy controls. Treatment with TPPU protected against apoptosis in human PARK2 iPSC-derived neurons. These findings suggest that increased activity of sEH in the striatum plays a key role in the pathogenesis of neurodegenerative disorders such as PD and DLB. Therefore, sEH represents a useful therapeutic target for α-synuclein-related neurodegenerative disorders.

Herein, we examined the role of sEH in the pathogenesis of PD. First, we examined the effects of TPPU (1-trifluoromethoxyphenyl-3-(1-propionylpiperidin-4-yl)urea), a potent sEH inhibitor (26,32,33), on dopaminergic neurotoxicity, endoplasmic reticulum (ER) stress, and oxidative stress in the mouse striatum after repeated administration of MPTP (1-methyl-4-phenyl-1,2,3,6-tetrahydropyridine). Second, using sEH knock-out (KO) mice, we examined the role of sEH in dopaminergic neurotoxicity, ER stress, and oxidative stress in the striatum from MPTP-treated mice. Third, we measured the protein expression of sEH in the striatum of MPTP-treated mice. We also performed oxylipin analysis of the striatum from MPTP-treated mice. Fourth, we measured the protein expressions of sEH, the dopamine transporter (DAT), tyrosine hydrogenase (TH), and other PD-related proteins (α-synuclein and phosphorylated α-synuclein) in postmortem brain samples from patients with dementia of Lewy bodies (DLB), as well as age-matched control subjects. Finally, using induced pluripotent stem cells (iPSCs), we examined whether sEH appeared to play a role in the pathogenesis of one case of familial PARK2 PD with mutations in the PARKIN gene (34).

2. Conditions Subject to Intervention or Treatment

Conditions subject to intervention or treatment are synucleinopathic diseases or disorders, e.g., neurodegenerative disorders, that are associated with, caused and/or mediated at least in part by alpha-synuclein aggregates or deposits, e.g., that accumulate in the brain. Synucleinopathies are a class of neurologic disorders, characterized by an abnormal accumulation of alpha-synuclein (aSYN or SNCA) protein into toxic oligomers and aggregates. The aggregates are downstream products of earlier pathological events, such as aberrant gene function, exposure to chemical toxins, and head trauma. Excessive aSYN oligomers are thought to overwhelm normal mechanisms for protein clearance, they impair mitochondrial function, and disrupt cellular architecture, leading to cell injury and death in vulnerable neuronal and glial populations. Illustrative diseases or disorders subject to intervention or treatment include without limitation Lewy Body dementias, e.g., Parkinson's Disease (PD) and Dementia with Lewy Bodies (DLB). Other disease conditions subject to intervention or treatment include without limitation Pick's Disease, Alzheimer's Disease and palsy. The methods further are useful for treating the different identified subtypes of Parkinson's Disease, including earlier disease onset, tremor dominant, non-tremor dominant, and rapid disease progression without dementia. See, e.g., Selikhova, et al., Brain. 2009 November;132(Pt 11):2947-57.

In some embodiments, the synucleinopathy disease or disorder is Parkinson's disease (PD), Parkinson's disease with dementia (PDD), dementia with Lewy bodies (DLB), Lewy body variant of Alzheimer's disease, Alzheimer's disease (AD), Multiple System Atrophy (MSA), Down syndrome, Progressive Supranuclear palsy (PSP), Corticobasal degeneration (CBD), Shy-Drager syndrome, Striatonigral degeneration, Olivopontocerebellar atrophy, Pure autonomic failure, Prion disease, Neurodegeneration with brain iron accumulation type 1 (NBIAI), Frontotemporal dementia (FTD)/Pick's disease, Parkinsonism dementia complex/Amyotrophic lateral sclerosis (PDC/ALS) of Guam, amyotrophic lateral sclerosis (ALS), or traumatic brain injury. In some embodiments, the synucleinopathy disease or disorder is a mutation or copy number variation in the human SNCA, LRRK2, PARK2, PARK7, PINK1, Parkin, DJ1, ATP13A2, PLA2G6, FBX07, UCHL1, GIGYF2, HTRA2, EIF4G1, GBA, MAPT, BST1, GAK, APP, PS1, PS2, SOD1, P102L, 6-OPRI, E200K, PLA2G6, PANK2, or FTL gene. In some embodiments, the synucleinopathy disease or disorder is an aneuploidy of human chromosome 21. In some embodiments, the subject expresses a mutant protein encoded by the SNCA, LRRK2, PARK2, PARK7, PINK1, Parkin, DJ1, ATP13A2, PLA2G6, FBX07, UCHL1, GIGYF2, HTRA2, EIF4G1, GBA, MAPT, BST1, GAK, APP, PS1, PS2, SOD1, P102L, 6-OPRI, E200K, PLA2G6, PANK2, or FTL gene. In some embodiments, the subject has been exposed to neurotoxic compounds or elements including paraquat, rotenone, maneb, manganese, 1-methyl 4-phenyl 1,2,3,6-tetrahydropyridine (MPTP), reserpine, thorazine, toluene, n-hexane, carbon disulfide, carbon monoxide, mercury, cyanide, copper, lead, trichloroethylene, perchloroethylene, or 2,4-dichlorophenoxyacetic acid. In some embodiments, the synucleinopathy disease or disorder is PD or DLB, or prodromal forms thereof. In some embodiments, the subject has been exposed to neurotoxic compounds. In some embodiments, the subject has experienced head trauma. In some embodiments, the synucleinopathy disease or disorder is a brain degeneration syndrome that may be caused by a head trauma history. For example, the synucleinopathy disease or disorder may be chronic traumatic encephalopathy. In some embodiments, the subjects having a synucleinopathy disease or disorder are carriers of a SNCA Repl polymorphism. This population is more susceptible to dementia associated with head trauma.

3. Subjects Amenable to Treatment

Subjects/patients amenable to treatment using the methods described herein include individuals at risk of disease (e.g., due to a known genetic association or applicable diagnostic test) but not showing symptoms, as well as subjects presently showing symptoms. It is known that the risk of diseases or disorders, e.g., neurodegenerative disorders, that are associated with, caused and/or mediated at least in part by alpha-synuclein aggregates or deposits, generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI) or subtle motor impairment, and/or to slow or prevent the progression to a neurodegenerative disorder associated with, caused and/or mediated at least in part by alpha-synuclein aggregates or deposits in the brain, e.g., Parkinson's Disease (PD) and Dementia with Lewy Bodies (DLB).

In certain embodiments, the methods described herein present methods are especially useful for individuals who do have a known genetic risk of developing a neurodegenerative disorder associated with, caused and/or mediated at least in part by alpha-synuclein aggregates or deposits, whether they are asymptomatic or showing symptoms of disease. Such individuals include those having relatives who have suffered from a neurodegenerative disorder associated with, caused and/or mediated at least in part by alpha-synuclein aggregates or deposits (e.g., a parent, a grandparent, a sibling), and those whose risk is determined by analysis of genetic or biochemical markers. Genetic markers of risk toward Parkinson's disease include, for example, a mutation in one or more genes selected from the group consisting of alpha-synuclein (SNCA), leucine rich repeat kinase 2 (LRRK2), vacuolar protein sorting (VPS) retromer complex component (VPS35), parkin RBR E3 ubiquitin protein ligase (PRKN or PARK2), PTEN induced putative kinase 1 (PINK1) and glucocerebrosidase (GBA). See, e.g., Mahlknecht, et al., *Journal of Parkinson's Disease* 5 (2015) 681-697 and references therein. Genetic markers of risk toward Alzheimer's disease include, for example, mutations in the APP gene, particularly mutations at position 717 and positions 670 and 671 referred to as the Hardy and Swedish mutations respectively (see Hardy (1997) *Trends. Neurosci.*, 20: 154-159). Other markers of risk include mutations in the presenilin genes (PS1 and PS2), family history of AD, having the familial Alzheimer's disease (FAD) mutation, the APOE ε4 allele, hypercholesterolemia or atherosclerosis. Further susceptibility genes for the development of Alzheimer's disease are reviewed, e.g., in Sleegers, et al. (2010) *Trends Genet.* 26(2): 84-93. Accordingly, in some embodiments, the subject is asymptomatic but has familial and/or genetic risk factors for developing MCI, Parkinson's Disease or Alzheimer's disease. In asymptomatic patients, treatment can begin at any age (e.g., 20, 30, 40, 50 years of age). Usually, however, it is not necessary to begin treatment until a patient reaches at least about 40, 50, 60 or 70 years of age.

In some embodiments, the subject has tested positive for prodromal Parkinson's Disease. Prodromal disease refers to the stage wherein early symptoms or signs of PD neurodegeneration are present, but classic clinical diagnosis based on fully evolved motor parkinsonism is not yet possible. Diagnostic markers for diagnosing that a subject has prodromal Parkinson's Disease include motor and nonmotor clinical symptoms, clinical signs, and ancillary diagnostic tests, and are described in e.g., Berg, et al., Mov Disord. 2015 Oct.;30(12):1600-11 and Mahlknecht, et al, *Journal of Parkinson's Disease* 5 (2015) 681-697. In some embodiments, the subject has tested positive for prodromal Dementia with Lewy Bodies (DLB). Dysautonomia (dysregulation of the autonomic nervous system), olfactory dysfunction, rapid eye movement sleep behavior disorder (RBD), motor symptoms, hallucinations and psychiatric symptoms antedate the onset of dementia by years or even decades in patients with DLB. See, e.g., Fujishiro, *Geriatr Gerontol Int.* 2015 Jul.;15(7):817-26; and Donaghy, et al., *Psychol Med.* 2015 January;45(2):259-68.

Many tissue-based and imaging based diagnostic tests are known in the art, and can be used to identify a subject who can benefit from the present treatment methods. Accordingly, in some embodiments, the methods entail determining whether the subject has an increased likelihood of developing, or is in the early stages of experiencing a neurodegenerative disorder associated with, caused and/or mediated at least in part by alpha-synuclein aggregates or deposits. In some embodiments, the subject has decreased expression of alpha-synuclein (SNCA) mRNA transcripts in circulating blood cells in comparison to a normal subject control (Locascio, et al., *Brain*. 2015 September;138(Pt 9):2659-71). In some embodiments, the subject has decreased serum levels of heat shock protein family A (Hsp70) member 9 (HSPA9 or mortalin) in comparison to a normal subject control (Singh, et al., Neuromolecular Med. 2018 Jan. 6, PMID 29307058). In some embodiments, the subject has increased levels of monoamine oxidase B (MAOB), alpha-synuclein (SNCA) and/or soluble epoxide hydrolase (EPHX2) in lymphocytes, blood, serum or cerebrospinal fluid (CSF) in comparison to a normal subject control (WO 2009/105481, Locascio, et al, supra; Kasuga, et al., *Int J Alzheimers Dis*. 2012; 2012:437025; and data provided herein). In some embodiments, the blood alpha-synuclein (SNCA) of the subject has altered post-translational modifications, e.g., one or more of increased Y125 phosphorylation, increased Y39 nitration, and decreased SUMOylation, in comparison to a normal control subject (Miranda, et al., Sci Rep. 2017 Oct. 20; 7(1):13713). In some embodiments, the subject has decreased cerebrospinal fluid (CSF) levels of one or more biomarkers selected from the group consisting of Aβ1-42, T tau, P-tau181, α-synuclein, and T-tau/Aβ1-42 in comparison to a normal control (Mahlknecht, et al., *Journal of Parkinson's Disease* 5 (2015) 681-697). In some embodiments, the subject has detectable nigrostriatal dopaminergic denervation, e.g., as detectable by single photon emission computed tomography (SPECT) or decarboxylase activity with 18F-Dopa positron emission tomography (PET) (Mahlknecht, et al., supra). In some embodiments, the subject has decreased radiotracer binding using striatal dopamine transporters (DAT)/single photon emission computed tomography (SPECT) imaging (Mahlknecht, et al., supra). In some embodiments, the subject demonstrates subtle motor impairment and/or mild cognitive impairment (MCI).

In some embodiments, the subject is asymptomatic for cognitive impairment but is exhibiting olfactory dysfunction. For example, the subject would fail or may have failed an olfactory challenge test. Numerous olfactory challenge tests are known in the art, and can be used to detect if an asymptomatic individual or an individual exhibiting symptoms of subtle motor impairment or mild cognitive impairment (MCI) is at risk of developing a neurodegenerative disorder associated with, caused and/or mediated at least in part by alpha-synuclein aggregates or deposits, e.g., Parkinson's Disease (including prodromal Parkinson's Disease), Dementia with Lewy Bodies (including prodromal Dementia with Lewy Bodies (DLB)), or Alzheimer's disease. Such olfactory challenge tests include without limitation the Alberta Smell Test (AST) (Heyanka, et al., *Appl Neuropsychol Adult*. (2014) 21(3):176-82); so-called "Sniffin' Sticks" (Neumann, et al., Clin Otolaryngol. 2012 February;37(1):23-7; available for purchase from USneurologicals.com); Short Smell Test (SST) (Streit et al. *BMC Geriatrics* (2015) 15:90); Cross-Cultural Smell Identification Test (CC-SIT) (Scalco, et al., *Int J Geriatr Psychiatry*. (2009) 24(4):376-81); University of Pennsylvania Smell Identification Test (UPSIT) (Schofield et al. BMC *Neurology* (2012) 12:24 and Velayudhan, et al., *Int Psychogeriatr*. (2013) 25(7):1157-66). In some embodiments, the subject demonstrates hyposmia, e.g., has failed an olfactory challenge test. In some embodiments, the subject suffers depression and/or anxiety.

In some embodiments, the subject is exhibiting symptoms, for example, of mild or moderate cognitive impairment (MCI), motor impairment or dementia, Parkinson's disease (PD) or Alzheimer's disease (AD). Individuals presently suffering from Parkinson's disease can be recognized from characteristic symptoms, including bradykinesia, tremor, rigidity, postural instability and cognitive impairment. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), Aβp42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/AP40 ratio, Aβ42/A338 ratio, sAPPα levels, sAPPα/sAPPβs ratio, sAPPα/Aβ40 ratio, and sAPPα/Aβ42 ratio signify the presence of AD. In some embodiments, the subject or patient is diagnosed as having MCI. Increased levels of neural thread protein (NTP) in urine and/or increased levels of a2-macroglobulin (a2M) and/or complement factor H (CFH) in plasma are also biomarkers of MCI and/or AD. See, Anoop, et al., *Int JAlzheimers Dis*. (2010) Jun. 23;2010. pii: 606802 (PMID 20721349). In some embodiments, the subject or patient is diagnosed as having Parkinson's disease, Dementia with Lewy Bodies (DLB) or Alzheimer's disease (e.g., early-stage, mid-stage or late-stage).

In certain embodiments, subjects amenable to treatment may have age-associated memory impairment (AAMI), or mild cognitive impairment (MCI). The methods described herein are particularly well-suited to the treatment of MCI. In such instances, the methods can reduce one or more symptoms characteristic of MCI and/or delay or prevent the progression from MCI to early-, mid- or late-stage Parkinson's disease, Dementia with Lewy Bodies, or Alzheimer's disease, or reduce the ultimate severity of the disease.

In various embodiments, the subject is a child, a juvenile or an adult. In various embodiments, the subject is a mammal, for example, a human or a domesticated mammal (e.g., a canine, a feline, an equine).

In some embodiments, the subject does not currently suffer from, is not being treated for, or has not been diagnosed with one or more, any or all of the following conditions: depression, major depression, schizophrenia, bipolar disorder, post-traumatic disorder (PTSD), eating disorder, substance abuse, drug addiction, drug dependency, social anxiety, Alzheimer's disease, cognitive decline, mild cognitive impairment, dementia, and attention-deficit hyperactivity disorder (ADHD), hypertension, cardiomyopathy, diabetes, metabolic syndrome, nephropathy, renal insufficiency, renal failure, neuropathic pain, inflammatory pain, obstructive pulmonary disease (e.g., COPD, bronchial asthma and small airway disease), pulmonary fibrosis, and cancer.

4. Inhibitors of Soluble Epoxide Hydrolase

Inhibitors of soluble epoxide hydrolase (sEH) include small organic compounds that inhibit the activity of the enzyme, inhibitory nucleic acids that inhibit expression of the enzyme, and phosphodiesterase 4 (PDE4 inhibitors).

a. Inhibitors of Soluble Epoxide Hydrolase (sEH)

Scores of sEH inhibitors are known, of a variety of chemical structures. Derivatives in which the urea, carbamate or amide pharmacophore are particularly useful as sEH inhibitors. As used herein, "pharmacophore" refers to the section of the structure of a ligand that binds to the sEH. Derivatives that are metabolically stable are of use, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999).

Derivatives of urea are transition state mimetics that form a group of sEH inhibitors. Within this group, N, N'-dodecyl-cyclohexyl urea (DCU), is an inhibitor, while N-cyclohexyl-N'-dodecylurea (CDU) is a particular embodiment. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. Both the 1- and the 2-adamantyl ureas have been tested and have about the same high activity as an inhibitor of sEH. Adamantyl ureas of use include, e.g., 12-(3-Adamantan-1-yl-ureido)dodecanoic acid (AUDA), 12-(3-Adamantan-1-yl-ureido)dodecanoic acid butyl ester (AUDA-BE), and Adamantan-1-yl-3-{5-[2-(2-ethoxyethoxy)ethoxy]pentyl}urea (AEPU).

Another group of inhibitors are piperidines. The following Tables sets forth some exemplar inhibitors of sEH and their ability to inhibit sEH activity of the human enzyme and sEH from equine, ovine, porcine, feline and canine, expressed as the amount needed to reduce the activity of the enzyme by 50% (expressed as "$IC_{50}$").

TABLE 1

$IC_{50}$ values for selected alkylpiperidine-based sEH inhibitors against human sEH

| R: | n = 0 Compound | n = 0 IC50 (μM)[a] | n = 1 Compound | n = 1 IC50 (μM)[a] |
|---|---|---|---|---|
| H | I | 0.30 | II | 4.2 |
| (ethyl) | 3a | 3.8 | 4.a | 3.9 |
| (propyl) | 3b | 0.81 | 4b | 2.6 |
| (butyl) | 3c | 1.2 | 4c | 0.61 |
| (benzyl) | 3d | 0.01 | 4d | 0.11 |

[a] As determined via a kinetic fluorescent assay.

TABLE 2 sEH inhibitors

| Structure | Name | sEHI # |
|---|---|---|
| (Cl-phenyl-NH-CO-NH-phenyl-Cl,Cl) | 3-(4-chlorophenyl)-1-(3,4-dichlorphenyl)urea or 3,4,4'-trichlorocarbanilide | 295 (TCC) |

TABLE 2-continued sEH inhibitors

| Structure | Name | sEHI # |
|---|---|---|
| | 1-trifluoromethoxyphenyl-3-(1-acetylpiperidin-4-yl) urea | 1555 (TPAU) |
| 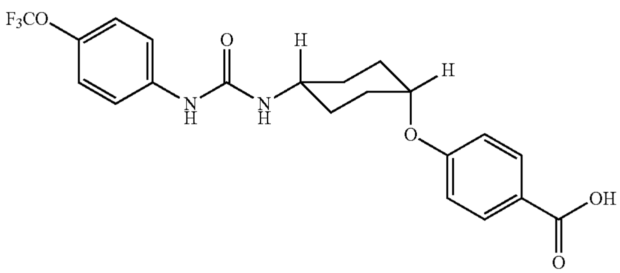 [SMILES: O=C(Nc1ccc(OC(F)(F)F)cc1)NC1CCC(Oc2ccc(C(=O)O)cc2)CC1] | cis-4-[4-(3-Adamantan-1-yl-ureido)-cyclohexyloxy]-benzoic acid | 1686 (cAUCB) |
| 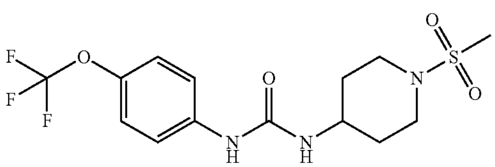 [SMILES: CS(=O)(=O)N1CCC(NC(=O)Nc2ccc(OC(F)(F)F)cc2)CC1] | 1-(1-methylsulfonyl-piperidin-4-yl)-3-(4-trifluoromethoxy-phenyl)-urea | 1709 (TUPS) |
| 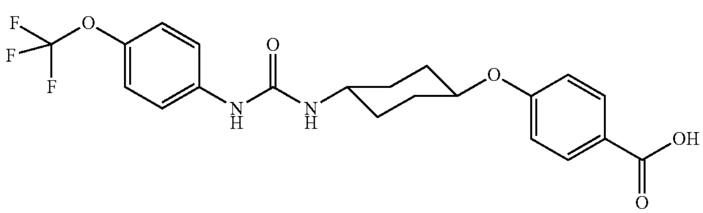 [SMILES: O=C(Nc1ccc(OC(F)(F)F)cc1)NC1CCC(Oc2ccc(C(=O)O)cc2)CC1] | trans-4-{4-[3-(4-Trifluoromethoxy-phenyl)-ureido]-cyclohexyloxy}-benzoic acid | 1728 (tTUCB) |
| 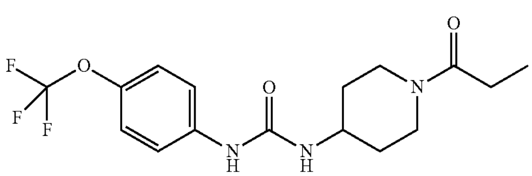 [SMILES: CCC(=O)N1CCC(NC(=O)Nc2ccc(OC(F)(F)F)cc2)CC1] | 1-trifluoromethoxyphenyl-3-(1-propionylpiperidin-4-yl) urea | 1770 (TPPU) |
| 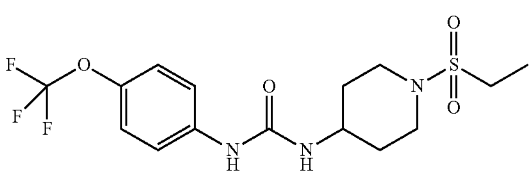 [SMILES: CCS(=O)(=O)N1CCC(NC(=O)Nc2ccc(OC(F)(F)F)cc2)CC1] | 1-(1-ethylsulfonyl-piperidin-yl)-3-(4-trifluoromethoxy-phenyl)-urea | 2213 (TUPSE) |
| 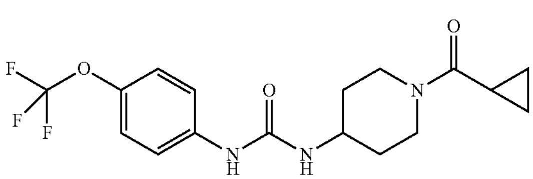 [SMILES: O=C(Nc1ccc(OC(F)(F)F)cc1)NC1CCN(C(=O)C2CC2)CC1] | 1-(1-(cyclopropanecarbonyl)piperidin-4-yl)-3-(4-(trifluoromethoxy)phenyl)urea | 2214 (CPTU) |
| 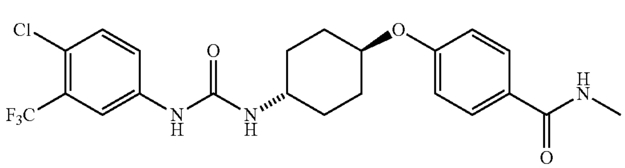 | trans-N-methyl- 4-[4-((3-trifluoromethyl-4-chlorophenyl)-ureido)-cyclohexyloxy]-benzamide | 2226 (tMTCUCB) |

TABLE 2-continued sEH inhibitors

| Structure | Name | sEHI # |
|---|---|---|
| 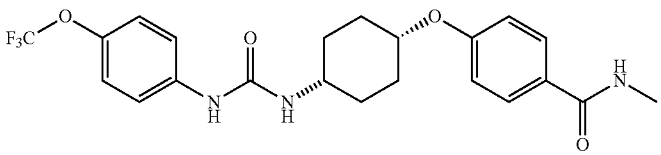 | cis-N-methyl-4-{4-[3-(4-trifluoromethoxy-phenyl)-ureido]-cyclohexyloxy}-benzamide | 2228 (cMTUCB) |
| 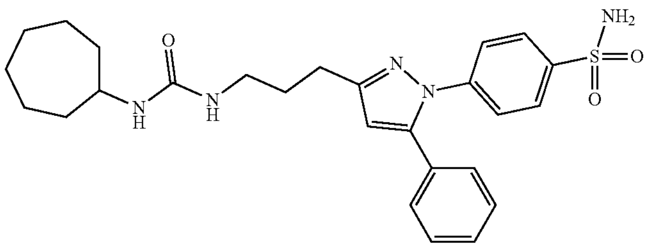 [SMILES: NS(=O)(=O)c1ccc(-n2nc(CCCNC(=O)NC3CCCCCC3)cc2-c2ccccc2)cc1] | 1-cycloheptyl-3-(3-(1,5-diphenyl-1H-pyrazol-3-yl)propypurea | 2247 (HDP3U) |

A number of other sEH inhibitors which can be used in the methods and compositions are described in published International Application Nos PCT/US2015/023048, PCT/US2013/024396, PCT/US2012/025074, PCT/US2011/064474, PCT/US2011/022901, PCT/US2008/072199, PCT/US2007/006412, PCT/US2005/038282, PCT/US2005/08765, PCT/US2004/010298; U.S. Published Patent Application Publication Nos: 2016/0200683, 2015/0011586, 2014/0088156, 2014/0038923, 2013/0274476, 2013/0143925, 2013/0137726, 2011/0098322, 2005/0026844, and U.S. Pat. No. 9,850,207 each of which is hereby incorporated herein by reference in its entirety for all purposes.

Additional piperidine inhibitors of sEH that find use in the present methods are described in U.S. Pat. No. 9,850,207 and WO 2015/148954. Piperidine compounds of interest are provided in Table 3. In some embodiments, the inhibitor of sEH is piperidine compound from Table 3 selected from the group consisting of 1-(3-fluoro-4-(trifluoromethoxy)phenyl)-3-(1-isobutyrylpiperidin-4-yl)ure-a (Compound 19); 1-(1-(tetrahydro-2H-pyran-4-carbonyl)piperidin-4-yl)-3-(4-(trifluorometho-xy)phenyl)urea (Compound 1); 1-(1-(cyclopropanecarbonyl)piperidin-4-yl)-3-(3-fluoro-4-(trifluoromethox-y)phenyl)urea (Compound 24); (S)-1-(3-fluoro-4-(trifluoromethoxy)phenyl)-3-(1-(2-methylbutanoyl)piperidin-4-yl)urea (Compound 26); and 1-(3-fluoro-4-(trifluoromethoxy)phenyl)-3-(1-(tetrahydro-2H-pyran-4-carbo-nyl)piperidin-4-yl)urea (Compound 29). Compound 29 has been demonstrated to cross the blood-brain barrier in a Pentylenetetrazol (PTZ) Induced Seizure Model (See, Example 52 and FIG. 7 of WO 2015/148954).

A further inhibitor of soluble epoxide hydrolase useful in the present methods is GSK2256294A (IUPAC/Chemical Name: (1R,3S)-N-(4-cyano-2-(trifluoromethyl)benzyl)-3-((4-methyl-6-(methylamino)-1,3,5-triazin-2-yl)amino)cyclohexane-1-carboxamide; CAS #: 1142090-23-0), described in Podolin, et al., *Prostaglandins Other Lipid Mediat.* (2013) 104-105:25-31, the structure of which is provided below:

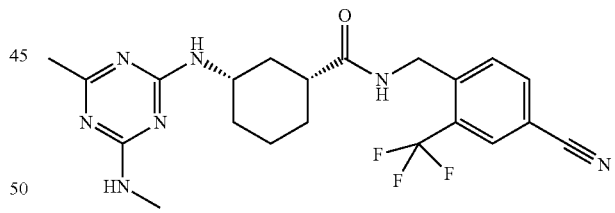

U.S. Pat. No. 5,955,496 (the '496 patent) also sets forth a number of sEH inhibitors which can be used in the methods. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

TABLE 3
POTENT PIPERIDINE INHIBITORS OF SEH
| Structure and Compound No. | Mol. Weight | Exp. logP[a] | Cal. log P[b] | Ki (nM) (human sEH)[c] | t$_{1/2}$ (min) (human sEH)[d] |
|---|---|---|---|---|---|
| 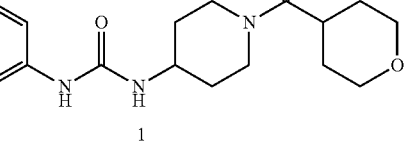 1 | 415.11 | 3.26 | 0.6 | 1.43 ± 0.01 | 14 |
| 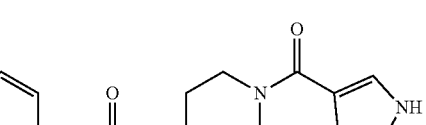 2 | 396.14 | 3.34 | 1.8 | 0.64 ± 0.17 | 15 |
| 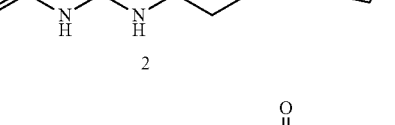 3 | 397.12 | 3.63 | 2.0 | 0.33 ± 0.34 | 17 |
| 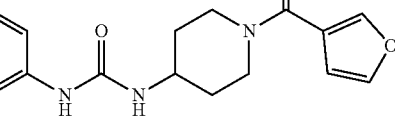 4 | 401.16 | 3.38 | 1.4 | 1.41 ± 0.11 | 17 |
| 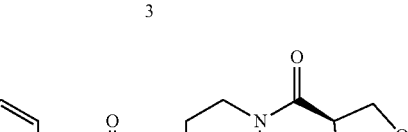 5 | 399.14 | 3.49 | 2.6 | 0.77 ± 0.02 | 13 |
| 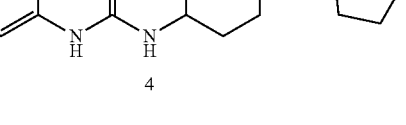 6 | 411.14 | 4.30 | 2.5 | 0.55 ± 0.06 | 15 |
| 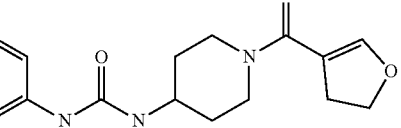 7 | 411.14 | 4.48 | 2.5 | 0.26 ± 0.11 | 21 |

TABLE 3-continued
POTENT PIPERIDINE INHIBITORS OF SEH
| Structure and Compound No. | Mol. Weight | Exp. logP[a] | Cal. log P[b] | Ki (nM) (human sEH)[c] | $t_{1/2}$ (min) (human sEH)[d] |
|---|---|---|---|---|---|
| 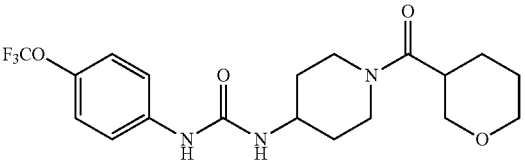<br>8 | 415.17 | 3.42 | 1.8 | 1.99 ± 0.23 | 13 |
| 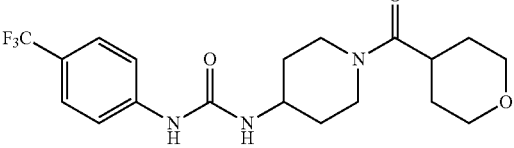<br>9 | 399.18 | 3.16 | 0.8 | 1.73 ± 0.01 | 11 |
| 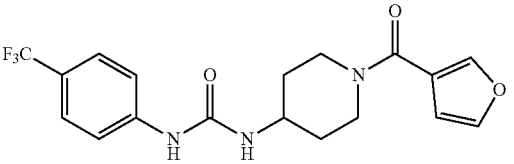<br>10 | 381.13 | 3.50 | 1.6 | 1.21 ± 0.2 | 11 |
| 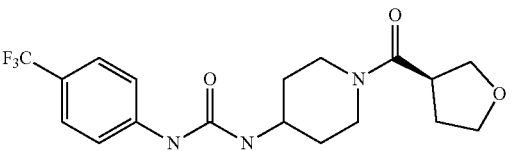<br>11 | 385.16 | 3.27 | 2.2 | 1.19 ± 0.08 | 13 |
| 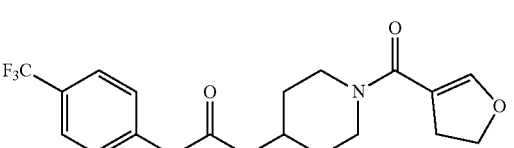<br>12 | 383.15 | 3.37 | 2.8 | 1.03 ± 0.20 | 8 |
| 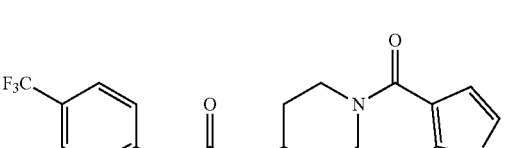<br>13 | 395.15 | 4.19 | 2.7 | 0.51 ± 0.03 | 11 |
| 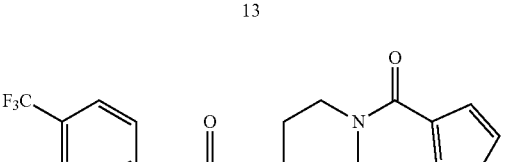<br>14 | 395.15 | 4.29 | 2.7 | 0.22 ± 0.01 | 15 |

TABLE 3-continued
POTENT PIPERIDINE INHIBITORS OF SEH
| Structure and Compound No. | Mol. Weight | Exp. logP[a] | Cal. log P[b] | Ki (nM) (human sEH)[c] | $t_{1/2}$ (min) (human sEH)[d] |
|---|---|---|---|---|---|
| 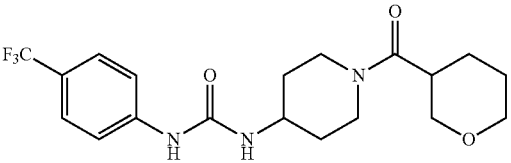 15 | 399.18 | 3.41 | 2.0 | 2.40 ± 0.08 | 11 |
| 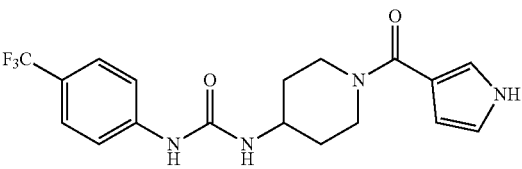 16 | 380.15 | 3.26 | 2.0 | 0.50 ± 0.01 | 10 |
| 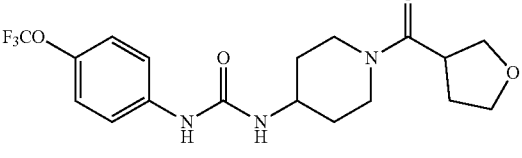 17 | 401.16 | 3.22 | 1.4 | 1.70 ± 0.01 | 12 |
| 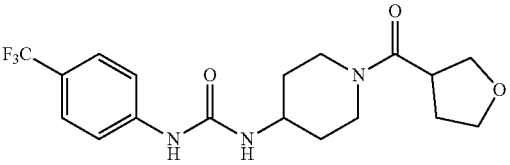 18 | 385.16 | 3.16 | 1.6 | 1.74 ± 0.11 | 10 |
| 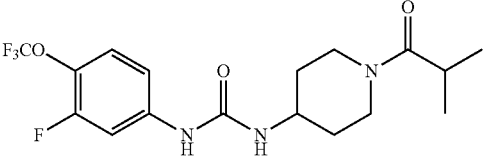 19 | 391.15 | 4.73 | 2.0 | 0.31 ± 0.01 | 22 |
| 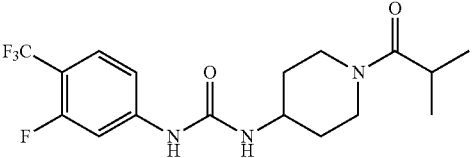 20 | 375.16 | 4.40 | 2.3 | 0.49 ± 0.4 | 12 |
| 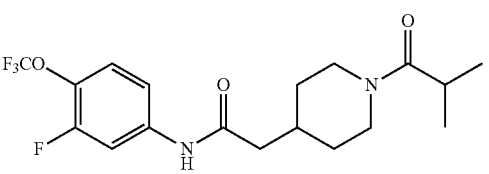 21 | 390.38 | 5.81 | 2.6 | 4.72 ± 0.70 | 3.4 |

TABLE 3-continued
POTENT PIPERIDINE INHIBITORS OF SEH
| Structure and Compound No. | Mol. Weight | Exp. logP[a] | Cal. log P[b] | Ki (nM) (human sEH)[c] | $t_{1/2}$ (min) (human sEH)[d] |
|---|---|---|---|---|---|
| 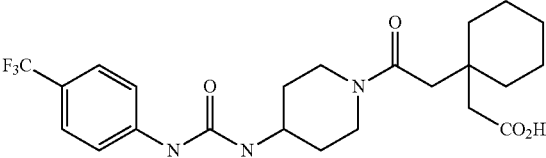 22 | 469.22 | — | — | 10.2 ± 1.1 | — |
| 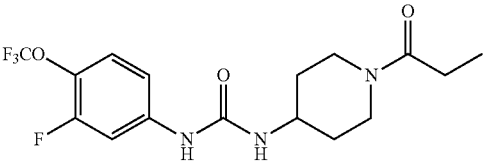 23 | 377.34 | 4.00 | 1.7 | 0.87 ± 0.13 | 11 |
| 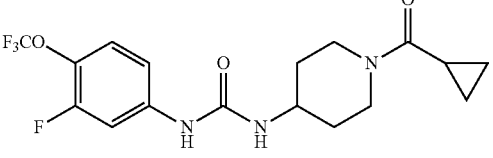 24 | 389.35 | 4.19 | 1.7 | 0.15 ± 0.04 | 19 |
| 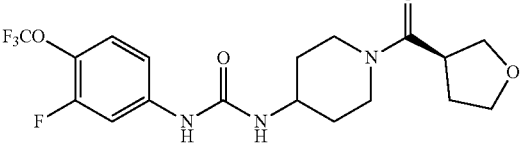 25 | 419.38 | 3.59 | 1.6 | 0.70 ± 0.01 | 13 |
| 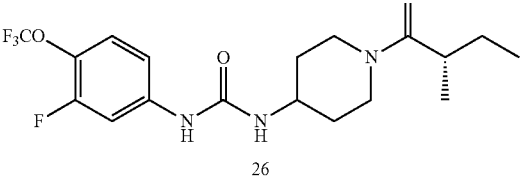 26 | 405.39 | 4.16 | 2.5 | <0.05 | 22 |
| 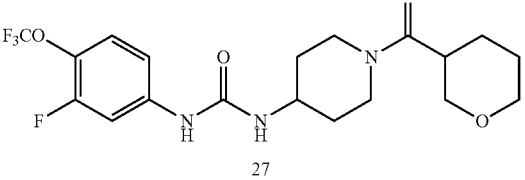 27 | 433.40 | 4.09 | 2.0 | 0.78 ± 0.19 | 12 |
| 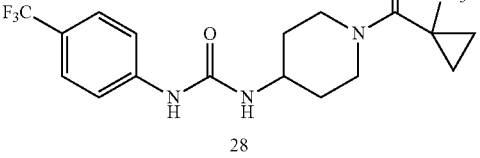 28 | 439.36 | 4.63 | 2.0 | 0.05 ± 0.04 | 24 |

TABLE 3-continued
POTENT PIPERIDINE INHIBITORS OF SEH
| Structure and Compound No. | Mol. Weight | Exp. logP[a] | Cal. log P[b] | Ki (nM) (human sEH)[c] | $t_{1/2}$ (min) (human sEH)[d] |
|---|---|---|---|---|---|
| 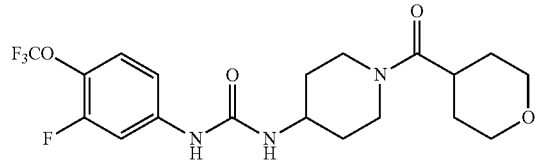 29 | 433.4 | 3.73 | 0.8 | 0.75 ± 0.05 | 11 |
| 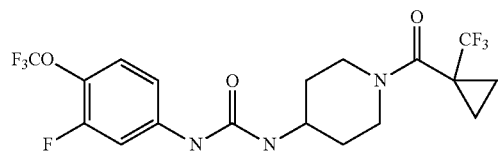 30 | 457.35 | 5.94 | 2.0 | <0.05 | 18 |
| 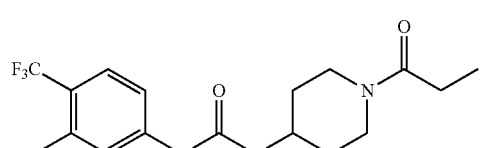 31 | 361.33 | 3.76 | 1.9 | 2.94 ± .01 | 3.3 |
| 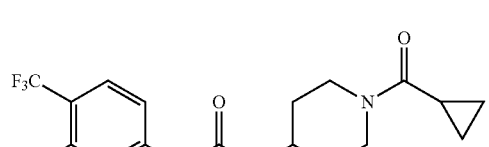 32 | 389.34 | 3.94 | 2.0 | 0.38 ± 0.08 | 8.2 |
| 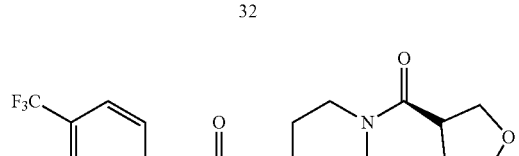 33 | 403.37 | 3.41 | 1.9 | 2.09 ± 0.24 | 5.3 |
| 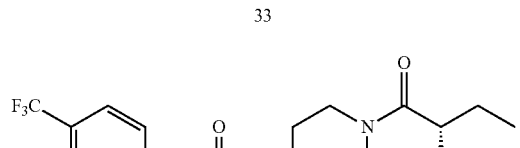 34 | 389.39 | 5.48 | 2.8 | 0.37 ± 0.03 | 13 |
| 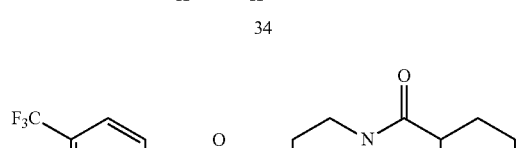 35 | 417.40 | 3.84 | 2.3 | 2.66 ± 0.19 | 6.8 |

TABLE 3-continued
POTENT PIPERIDINE INHIBITORS OF SEH
| Structure and Compound No. | Mol. Weight | Exp. logP[a] | Cal. log P[b] | Ki (nM) (human sEH)[c] | $t_{1/2}$ (min) (human sEH)[d] |
|---|---|---|---|---|---|
| 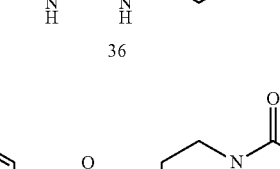 36 | 441.34 | 5.52 | 2.5 | 0.08 ± 0.01 | 21 |
| 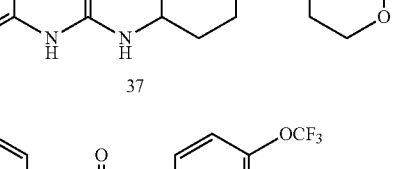 37 | 417.40 | 3.52 | 1.1 | 3.83 ± 0.41 | 6.9 |
| 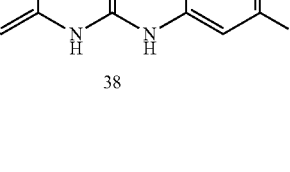 38 | 416.23 | ND | ND | 1.95 ± 0.30 | ND |
| 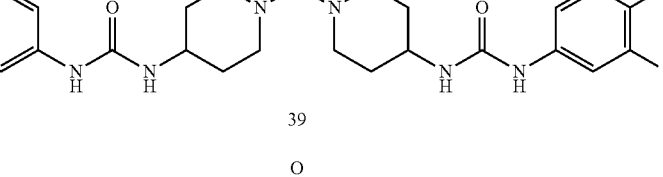 39 | 668.50 | ND | ND | 10.1 ± 1.8 | ND |
| 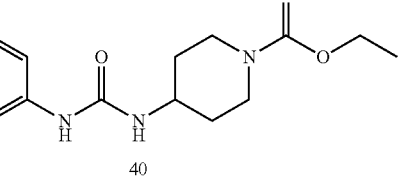 40 | 393.34 | 5.94 | 3.3 | <0.05 | 18 |
| 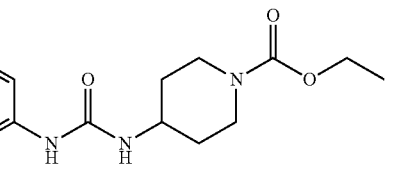 41 | 377.34 | 5.46 | 3.6 | 0.38 ± 0.03 | 7.6 |
| 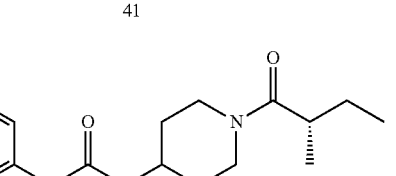 42 | 372.39 | 3.22 | 1.7 | 45.0 ± 2.3 | 3.7 |

TABLE 3-continued
POTENT PIPERIDINE INHIBITORS OF SEH
| Structure and Compound No. | Mol. Weight | Exp. logP[a] | Cal. log P[b] | Ki (nM) (human sEH)[c] | t$_{1/2}$ (min) (human sEH)[d] |
|---|---|---|---|---|---|
| 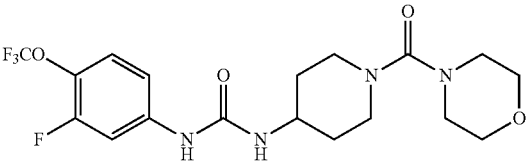 43 | 434.39 | 3.93 | 2.6 | 0.70 ± 0.06 | 15 |
| 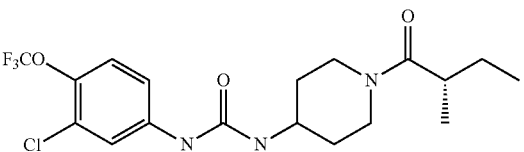 44 | 421.85 | 7.70 | 3.0 | 3.35 ± 0.42 | 10 |
| 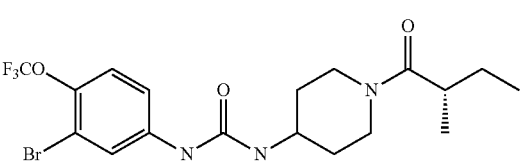 45 | 465.29 | 8.07 | 3.2 | 3.40 ± 1.38 | 9.3 |
| 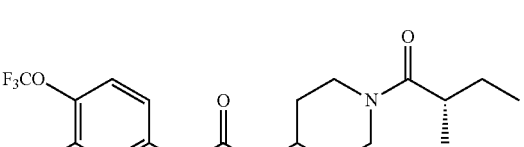 46 | 455.40 | 9.02 | 3.7 | 9.91 ± 3.37 | 5.9 |
| 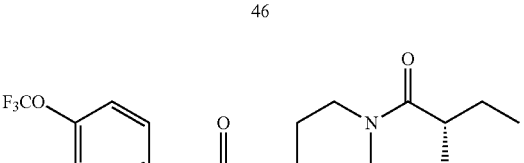 47 | 471.40 | 10.62 | 3.1 | 9.07 ± 0.36 | 11 |
| 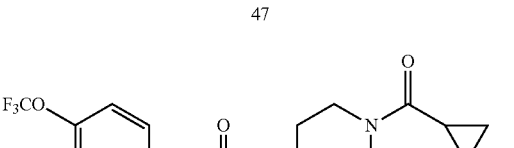 48 | 388.36 | 5.11 | 2.3 | 6.60 ± 0.01 | 3.3 |
| 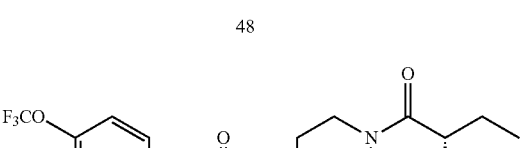 49 | 404.41 | 7.68 | 3.1 | 3.14 ± 0.70 | 4.5 |

TABLE 3-continued

POTENT PIPERIDINE INHIBITORS OF SEH

| Structure and Compound No. | Mol. Weight | Exp. logP[a] | Cal. log P[b] | Ki (nM) (human sEH)[c] | $t_{1/2}$ (min) (human sEH)[d] |
|---|---|---|---|---|---|
| 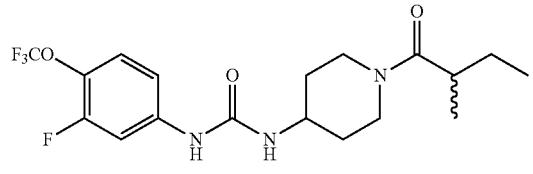 51 | 405.39 | ND | 2.5 | 0.06 ± 0.01 | ND |

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods are set forth in U.S. Pat. No. 6,150,415 (the '415 patent) and U.S. Pat. No. 6,531,506 (the '506 patent).

Derivatives of the sEHI can be designed. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (*Goodman and Gilman's The Pharmacological Basis of Therapeutics,* 13th Edition, 2017, McGraw-Hill). Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

In various embodiments, the inhibitor inhibits sEH without also significantly inhibiting microsomal epoxide hydrolase ("mEH"). In various embodiments, at concentrations of 100 μM, the inhibitor inhibits sEH activity by at least 50% while not inhibiting mEH activity by more than 10%. Compounds have an $IC_{50}$ (inhibition potency or, by definition, the concentration of inhibitor which reduces enzyme activity by 50%) of less than about 100 μM. Inhibitors with $IC_{50}$s of less than 100 M are of use, e.g., compounds with $IC_{50}$s of less than 75 M e.g., compounds with an $IC_{50}$ of 50 PM, 40 M, 30 μM, 25 μM, 20 μM, 15 μM, 10 μM, 5 μM, 3 μM, 2 μM, 1 μM, 100 nM, 10 nM, 1.0 nM, or even less. Assays for determining sEH activity are known in the art and described elsewhere herein. The $IC_{50}$ determination of the inhibitor can be made with respect to an sEH enzyme from the species subject to treatment (e.g., the subject receiving the inhibitor of sEH).

b. Phosphodiesterase Inhibitors (PDEi)

Phosphodiesterase inhibitors (PDEi) are well known anti-inflammatory agents. Many different classes of isozyme selective PDEi lead to remarkable increases in the plasma levels of a broad range of epoxy-fatty acids (EFA). The magnitude of this increase is so dramatic that PDEi can elevate epoxy-fatty acids as well as highly potent inhibitors of soluble epoxide hydrolase. Accordingly, levels of epoxy-fatty acids (e.g., in blood, plasma, serum) can be increased by administration of a phosphodiesterase inhibitor (PDEi).

The PDEi may or may not be selective, specific or preferential for cAMP. Exemplary PDEs that degrade cAMP include without limitation PDE3, PDE4, PDE7, PDE8 and PDE10. Exemplary cAMP selective hydrolases include PDE4, 7 and 8. Exemplary PDEs that hydrolyse both cAMP and cGMP include PDEI, PDE2, PDE3, PDE10 and PDE11. Isoenzymes and isoforms of PDEs are well known in the art. See, e.g., Boswell-Smith et al., *Brit. J. Pharmacol.* 147: 5252-257 (2006), and Reneerkens, et al., *Psychopharmacology* (2009) 202:419-443, the contents of which are incorporated herein by reference.

In some embodiments, the PDE inhibitor is a non-selective inhibitor of PDE. Exemplary non-selective PDE inhibitors that find use include without limitation caffeine, theophylline, isobutylmethylxanthine, aminophylline, pentoxifylline, vasoactive intestinal peptide (VIP), secretin, adrenocorticotropic hormone, pilocarpine, alpha-melanocyte stimulating hormone (MSH), beta-MSH, gamma-MSH, the ionophore A23187, prostaglandin E1.

In some embodiments, the PDE inhibitor used specifically or preferentially inhibits PDE4. Exemplary inhibitors that selectively inhibit PDE4 include without limitation rolipram, roflumilast, cilomilast, ariflo, HT0712, ibudilast and mesembrine.

In some embodiments, the PDE inhibitor used specifically or preferentially inhibits a cAMP PDE, e.g., PDE4, PDE7 or PDE8. In some embodiments, the PDE inhibitor used inhibits a cAMP PDE, e.g., PDE1, PDE2, PDE3, PDE4, PDE7, PDE8, PDE10 or PDE11. Exemplary agents that inhibit a cAMP phosphodiesterase include without limitation rolipram, roflumilast, cilomilast, ariflo, HT0712, ibudilast, mesembrine, cilostamide, enoxamone, milrinone, siguazodan and BRL-50481.

In some embodiments, the PDE inhibitor used specifically inhibits PDE5. Exemplary inhibitors that selectively inhibit PDE5 include without limitation sildenafil, zaprinast, tadalafil, udenafil, avanafil and vardenafil.

c. Assays for Detecting Epoxide Hydrolase Activity

Any of a number of standard assays for determining epoxide hydrolase activity can be used to determine inhibition of sEH. For example, suitable assays are described in Gill,. et al., Anal Biochem 131:273-282 (1983); and Borhan, et al., Analytical Biochemistry 231:188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J.H. and H.C. Rilling, eds. 1985), Academic Press, Orlando, Florida, pp. 303-311 and Wixtrom et al. , In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174: 291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

d. Other Means of Inhibiting sEH Activity

Provided herein are methods for reducing, inhibiting and/or reversing one or more symptoms and/or progression of a neurodegenerative disorder associated with, caused and/or mediated at least in part by alpha-synuclein aggregates or deposits, comprising administering to a subject in need thereof a therapeutically effective amount of a nucleic acid that reduces or inhibits the expression of sEH (EPHX2). Decreasing or inhibiting sEH (EPHX2) gene expression can be achieved using any method in the art, including through the use of inhibitory nucleic acids (e.g., small interfering RNA (siRNA), micro RNA (miRNA), antisense RNA, ribozymes, etc.). Inhibitory nucleic acids can be single-stranded nucleic acids that can specifically bind to a complementary nucleic acid sequence. By binding to the appropriate target sequence, an RNA-RNA, a DNA-DNA, or an RNA-DNA duplex or triplex is formed. Such inhibitory nucleic acids can be in either the "sense" or "antisense" orientation. See, for example, Tafech, et al., Curr Med Chem (2006) 13:863-81; Mahato, et al., Expert Opin Drug Deliv (2005) 2:3-28; Scanlon, Curr Pharm Biotechnol (2004) 5:415-20; and Scherer and Rossi, Nat Biotechnol (2003) 21:1457-65.

In one embodiment, the inhibitory nucleic acid can specifically bind to a target nucleic acid sequence or subsequence that encodes a human sEH (EPHX2). Administration of such inhibitory nucleic acids can decrease or inhibit the expression or overexpression of sEH (EPHX2) and consequently the progression of the neurodegenerative disorder associated with, caused and/or mediated at least in part by alpha-synuclein aggregates or deposits. Nucleotide sequences encoding a sEH (EPHX2) are known for several sEH (EPHX2) species, including humans, e.g., Ref Seq Nos. NM_001979.5→NP_001970.2 (isoform a); NM_001256484.1→NP_001243413.1 (isoform b); NM_001256482.1→NP_001243411.1 (isoform b); NM_001256483.1→NP_001243412.1 (isoform c). From these nucleotide sequences, one can design and produce a suitable inhibitory nucleic acid. In various embodiments, the inhibitory nucleic acid is a small interfering RNA (siRNA), a microRNA (miRNA), a Piwi-interacting RNA (piRNA), a small nuclear RNA (snRNA), an antisense oligonucleotide or a ribozyme. Various types of inhibitors for inhibiting nucleic acid function are well known in the art. See e.g., International patent application WO/2012/018881; U.S. patent application 2011/0251261; U.S. Pat. No. 6,713,457; Kole et al. (2012) Nat. Rev. Drug Discov. 11(2):125-40; Sanghvi (2011) Curr. Protoc. Nucleic Acid Chem. Chapter 4:Unit 4.1.1-22; herein incorporated by reference in their entireties.

Inhibitors can be single stranded or double stranded polynucleotides and may contain one or more chemical modifications, such as, but not limited to, locked nucleic acids, peptide nucleic acids, sugar modifications, such as 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages. In addition, inhibitory RNA molecules may have a "tail" covalently attached to their 3'- and/or 5'-end, which may be used to stabilize the RNA inhibitory molecule or enhance cellular uptake. Such tails include, but are not limited to, intercalating groups, various kinds of reporter groups, and lipophilic groups attached to the 3' or 5' ends of the RNA molecules. In certain embodiments, the RNA inhibitory molecule is conjugated to cholesterol or acridine. See, for example, the following for descriptions of syntheses of 3'-cholesterol or 3'-acridine modified oligonucleotides: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993); herein incorporated by reference in their entireties. Additional lipophilic moieties that can be used, include, but are not limited to, oleyl, retinyl, and cholesteryl residues, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O.sub.3-(oleoyl)lithocholic acid, 0.sub.3-(oleoyl)cholenic acid, dimethoxytrityl, or phenoxazine. Additional compounds, and methods of use, are set out in US Patent Publication Nos. 2010/0076056, 2009/0247608 and 2009/0131360; herein incorporated by reference in their entireties.

In one embodiment, inhibition of sEH (EPHX2) function may be achieved by administering antisense oligonucleotides targeting sEH (EPHX2). The antisense oligonucleotides may be ribonucleotides or deoxyribonucleotides. Preferably, the antisense oligonucleotides have at least one chemical modification. Antisense oligonucleotides may be comprised of one or more "locked nucleic acids". "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. Alternatively, the antisense oligonucleotides may comprise peptide nucleic acids (PNAs), which contain a peptide-based backbone rather than a sugar-phosphate backbone. The antisense oligonucleotides may contain one or more chemical modifications, including, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods. Antisense oligonucleotides may comprise a sequence that is at least partially complementary to a sEH (EPHX2) target sequence, e.g., at least about 75%, 80%, 85%, 90%, 91%, 92%, 93%, 94%, 95%, 96%, 97%, 98%, or 99% complementary to the sEH (EPHX2) target sequence. In some embodiments, the antisense oligonucleotide may be substantially complementary to the sEH (EPHX2) target sequence, that is at least about 95%, 96%, 97%, 98%, or 99% complementary to a target polynucleotide sequence. In one embodiment, the antisense oligonucleotide comprises a sequence that is 100% complementary to the sEH (EPHX2) target sequence.

In another embodiment, the inhibitor of sEH (EPHX2) is an inhibitory RNA molecule (e.g., a miRNA, a siRNA, a piRNA, or a snRNA) having a single-stranded or double-stranded region that is at least partially complementary to the target sequence of sEH (EPHX2), e.g., about 75%, 80%, 85%, 90%, 91%, 92%, 93%, 94%, 95%, 96%, 97%, 98%, or 99% complementary to the target sequence of sEH (EPHX2). In some embodiments, the inhibitory RNA comprises a sequence that is substantially complementary to the target sequence of sEH (EPHX2), e.g., about 95%, 96%, 97%, 98%, or 99% complementary to a target polynucleotide sequence. In other embodiments, the inhibitory RNA molecule may contain a region that has 100% complementarity to the target sequence. In certain embodiments, the inhibitory RNA molecule may be a double-stranded, small interfering RNA or a short hairpin RNA molecule (shRNA) comprising a stem-loop structure.

In some embodiments, a sEH (EPHX2) nucleic acid inhibitor reduces the expression and/or activity of sEH (EPHX2) by at least about 10% to about 100%, 20% to about 100%, 30% to about 100%, 40% to about 100%, 50% to about 100%, 60% to about 100%, 70% to about 100%, 10% to about 90%, 20% to about 85%, 40% to about 84%, 60% to about 90%, including any percent within these ranges, such as but not limited to 15%, 20%, 25%, 30%, 35%, 40%, 45%, 50%, 55%, 60%, 65%, 70%, 75%, 80%, 85%, 90%, 95%, 96%, 97%, 98%, and 99%.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993).

A program, siDESIGN from Dharmacon, Inc. (Lafayette, CO), permits predicting siRNAs for any nucleic acid sequence, and is available on the World Wide Web at dharmacon.com. Programs for designing siRNAs are also available from others, including Genscript (available on the Web at genscript.com/ssl-bin/app/mai) and, to academic and non-profit researchers, from the Whitehead Institute for Biomedical Research found on the worldwide web at "jura.wi.mit.edu/pubint/http://iona.wi.mit.edu/siRNAext/."

For example, using the program available from the Whitehead Institute, the following sEH target sequences and siRNA sequences can be generated:

```
1) Target:
                                    (SEQ ID NO: 3)
CAGTGTTCATTGGCCATGACTGG Sense-siRNA:
                                    (SEQ ID NO: 4)
5'-GUGUUCAUUGGCCAUGACUTT-3'

Antisense-siRNA:
                                    (SEQ ID NO: 5)
5'-AGUCAUGGCCAAUGAACACTT-3'

2) Target:
                                    (SEQ ID NO: 6)
GAAAGGCTATGGAGAGTCATCTG Sense-siRNA:
                                    (SEQ ID NO: 7)
5'-AAGGCUAUGGAGAGUCAUCTT-3'

Antisense-siRNA:
                                    (SEQ ID NO: 8)
5'-GAUGACUCUCCAUAGCCUUTT-3'

3) Target
                                    (SEQ ID NO: 9)
AAAGGCTATGGAGAGTCATCTGC Sense-siRNA:
                                    (SEQ ID NO: 10)
5'-AGGCUAUGGAGAGUCAUCUTT-3'

Antisense-siRNA:
                                    (SEQ ID NO: 11)
5'-AGAUGACUCUCCAUAGCCUTT-3'

4) Target:
                                    (SEQ ID NO: 12)
CAAGCAGTGTTCATTGGCCATGA Sense-siRNA:
                                    (SEQ ID NO: 13)
5'-AGCAGUGUUCAUUGGCCAUTT-3'

Antisense-siRNA:
                                    (SEQ ID NO: 14)
5'-AUGGCCAAUGAACACUGCUTT-3'

5) Target:
                                    (SEQ ID NO: 15)
CAGCACATGGAGGACTGGATTCC Sense-siRNA:
                                    (SEQ ID NO: 16)
5'-GCACAUGGAGGACUGGAUUTT-3'

Antisense-siRNA:
                                    (SEQ ID NO: 17)
5'-AAUCCAGUCCUCCAUGUGCTT-3'
```

Alternatively, siRNA can be generated using kits which generate siRNA from the gene. For example, the "Dicer siRNA Generation" kit (catalog number T510001, Gene Therapy Systems, Inc., San Diego, CA) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, TX) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, WA). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

```
1) Target:
                                    (SEQ ID NO: 19)
CAGTGTTCATTGGCCATGACTGG Sense strand:
                                    (SEQ ID NO: 20)
5'-GATCCCCGTGTTCATTGGCCATGACTTTCAA

GAGAAGTCATGGCCAATGAACACTTTTT-3'

Antisense strand:
```

```
                                             (SEQ ID NO: 21)
5'-AGCTAAAAAGTGTTCATTGGCCATGACTTCT

CTTGAAAGTCATGGCCAATGAACACGGG-3'

2) Target:
                                             (SEQ ID NO: 22)
GAAAGGCTATGGAGAGTCATCTG Sense strand:
                                             (SEQ ID NO: 23)
5'-GATCCCCAAGGCTATGGAGAGTCATCTTCAAG

AGAGATGACTCTCCATAGCCTTTTTTT-3'

Antisense strand:
                                             (SEQ ID NO: 24)
5'-AGCTAAAAAAAGGCTATGGAGAGTCATCTCTC

TTGAAGATGACTCTCCATAGCCTTGGG-3'

3) Target:
                                             (SEQ ID NO: 25)
AAAGGCTATGGAGAGTCATCTGC Sense strand:
                                             (SEQ ID NO: 26)
5'-GATCCCCAGGCTATGGAGAGTCATCTTTC

AAGAGAAGATGACTCTCCATAGCCTTTTTT-3'

Antisense strand:
                                             (SEQ ID NO: 27)
5'-AGCTAAAAAAGGCTATGGAGAGTCATCATC

TCTTGAAAGATGACTCTCCATAGCCTGGG-3'

4) Target:
                                             (SEQ ID NO: 28)
CAAGCAGTGTTCATTGGCCATGA Sense strand:
                                             (SEQ ID NO: 29)
5'-GATCCCCAGCAGTGTTCATTGGCCATTTCAAGAGAATG

GCCAATGAACACTGCTTTTTT-3'

Antisense strand:
                                             (SEQ ID NO: 30)
5'-AGCTAAAAAAGCAGTGTTCATTGGCCATTCTCTTGAAATG

GCCAATGAACACTGCTGGG-3'

5) Target:
                                             (SEQ ID NO: 31)
CAGCACATGGAGGACTGGATTCC Sense strand
                                             (SEQ ID NO: 32)
5'-GATCCCCGCACATGGAGGACTGGATTTTCAAGAGAAATC

CAGTCCTCCATGTGCTTTTT-3'

Antisense strand:
                                             (SEQ ID NO: 33)
5'-AGCTAAAAAGCACATGGAGGACTGGATTTCTCTTGAAAA

TCCAGTCCTCCATGTGCGGG-3'
```

More recently, it has been discovered that siRNAs can be introduced into mammals without eliciting an immune response by encapsulating them in nanoparticles of cyclodextrin. Information on this method can be found on the worldwide web at "nature.com/news/2005/050418/full/050418-6.html."

The nucleic acid can also be introduced into the body in a virus modified to serve as a vehicle without causing pathogenicity. The virus can be, for example, adenovirus, fowlpox virus or vaccinia virus. In some embodiments, the inhibitory nucleic acid is administered intranasally (Aly, et al., *Expert Opin Drug Deliv.* 2015; 12(12):1923-41).

In some embodiments, the endogenous polynucleotide encoding sEH in the subject can be rendered non-functional or non-expressing, e.g., by employing gene therapy methodologies. This can be accomplished using any method known in the art, including the working embodiment described herein. In various embodiments, the endogenous gene encoding sEH in the subject is rendered non-functional or non-expressing in certain desired tissues, e.g., in brain tissue or more specifically in brain cells, as demonstrated herein. In various embodiments, the endogenous gene encoding sEH in the subject is rendered non-functional or non-expressing by employing homologous recombination, mutating, replacing or eliminating the functional or expressing gene encoding sEH. Illustrative methods are known in the art and described, e.g., in Flynn, et al., *Exp Hematol.* (2015) Jun. 19. pii: S0301-472X(15)00207-6 (using CRISPR); Truong, et al, *Nucleic Acids Res.* (2015) Jun. 16. pii: gkv601 (using split-Cas9); Yang, *Mil Med Res.* (2015) May 9; 2:11 (using CRISPR-Cas9); and Imai, et al., *Intern Med.* (2004) February;43(2):85-96.

5. Co-Inhibition Strategies

In various embodiments, the sEHI is co-administered with an enhancing or synergizing agent. Illustrative agents that enhance the activity or efficaciousness of directly inhibiting soluble epoxide hydrolase include without limitation inhibitors of cyclooxygenase-2 (COX-2), inhibitors of phosphodiesterase, agonists of peroxisome proliferator activated receptor alpha (PPARα) and agonists of peroxisome proliferator activated receptor gamma (PPARγ).

Illustrative selective or preferential inhibitors of COX-2 that may be co-administered with an inhibitor of soluble epoxide hydrolase include without limitation celecoxib, valdecoxib, lumiracoxib, etoricoxib, and rofecoxib. Illustrative inhibitors of phosphodiesterase 4 that may be co-administered with an inhibitor of soluble epoxide hydrolase include without limitation rolipram, roflumilast, cilomilast, ariflo, HT0712, ibudilast and mesembrine. Illustrative inhibitors of phosphodiesterase 5 that may be co-administered with an inhibitor of soluble epoxide hydrolase include without limitation sildenafil, zaprinast, tadalafil, udenafil, avanafil and vardenafil. Illustrative agonists of PPARα that may be co-administered with an inhibitor of soluble epoxide hydrolase include without limitation clofibrate, gemfibrozil, ciprofibrate, bezafibrate, and fenofibrate. Illustrative agonists of PPARγ that may be co-administered with an inhibitor of soluble epoxide hydrolase include without limitation thiazolidinediones (TZDs).

In various embodiments, a compound with combined functionality to concurrently inhibit sEH and COX-2 is administered. Urea-containing pyrazoles that function as dual inhibitors of cyclooxygenase-2 and soluble epoxide hydrolase are described, e.g., in Hwang, et al., *J Med Chem.* (2011) 28;54(8):3037-50 and WO 2012/082647.

A general structure of inhibitors that inhibit both COX-2 and sEH are provided below.

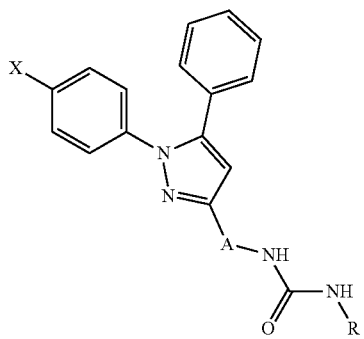

general structure may have different functional groups on:
X: MeSO₂ or H₂NSO₂
A: various carbon linkers
R: carbocyclic, aryl groups, or heterocyclic groups Inhibitory activities against sEH, COX-1 and COX-2 of illustrative dual inhibitors of COX-2 and sEH are provided in Table 4 below.

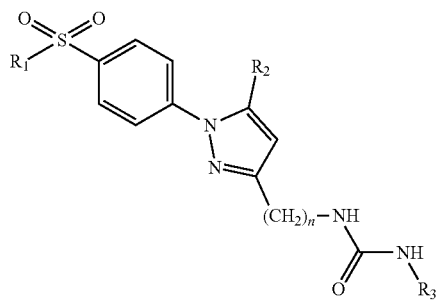

In some embodiments, the dual inhibitor of sEH and COX-2 is 4-(5-phenyl-3-{3-[3-(4-trifluoromethyl-phenyl)-ureido]-propyl}-pyrazol-1-yl)-benzenesulfonamide (PTUPB). In some embodiments, the dual inhibitor of sEH and COX 2 is a compound in Table 4 selected from the group consisting of:

compound 1860 (1-Adamantan-1-yl-3-[1-(4-methanesulfonyl-phenyl)-5-phenyl-1H-pyrazol-3-ylmethyl]-urea),
compound 2321 (1-Cycloheptyl-3-[1-(4-methanesulfonyl-phenyl)-5-phenyl-1H-pyrazol-3-ylmethyl]-urea),
compound 2322 (1-[1-(4-Methanesulfonyl-phenyl)-5-phenyl-1H-pyrazol-3-ylmethyl]-3-phenyl-urea), compound 2323 (1-[1-(4-Methanesulfonyl-phenyl)-5-phenyl-1H-pyrazol-3-ylmethyl]-3-(4-trifluoromethoxy-phenyl)-urea),
compound 2324 (1-[1-(4-Methanesulfonyl-phenyl)-5-phenyl-1H-pyrazol-3-ylmethyl]-3-(4-trifluoromethyl-phenyl)-urea),
compound 1861 (1-[I-(4-Methanesulfonyl-phenyl)-5-phenyl-1H-pyrazol-3-ylmethyl]-3-(3-trifluoromethyl-phenyl)-urea),
compound 2107 (4-{5-Phenyl-3-[3-(3-trifluoromethyl-phenyl)-ureidomethyl]-pyrazol-1-yl}-benzenesulfonamide),
compound 2106 (1-[5-tert-Butyl-1-(4-methanesulfonyl-phenyl)-1H-pyrazol-3-ylmethyl]-3-(3-trifluoromethyl-phenyl)-urea),
compound 2121 (4-{5-Phenyl-3-[3-(3-trifluoromethyl-phenyl)-ureido]-pyrazol-1-yl}-benzenesulfonamide),
compound 2313 (4-(5-Phenyl-3-{2-[3-(3-trifluoromethyl-phenyl)-ureido]-ethyl}-pyrazol-1-yl)-benzenesulfonamide),
compound 1862 (1-{3-[1-(4-Methanesulfonyl-phenyl)-5-phenyl-1H-pyrazol-3-yl]-propyl}-3-(3-trifluoromethyl-phenyl)-urea),
compound 2246 (4-(5-Phenyl-3-{3-[3-(3-trifluoromethyl-phenyl)-ureido]-propyl}-pyrazol-1-yl)-benzenesulfonamide),
compound 2152 (4-(5-p-Tolyl-3-{3-[3-(3-trifluoromethyl-phenyl)-ureido]-propyl}-pyrazol-1-yl)-benzenesulfonamide),

TABLE 4

Inhibitory activities against sEH, COX-1 and COX-2.

| sEH-COX-2 dual inhibitor | $R_1$ | $R_2$ | $R_3$ | n | COX-2 (µM) | COX-1 (% inhibition at 100 mM) | sEH (nM) |
|---|---|---|---|---|---|---|---|
| 1860 | Me | Ph | Adamantyl | 1 | >10 | 12.7 | 25 ± 1 |
| 2321 | Me | Ph | cHep | 1 | >10 | 3.4 | 2.6 ± 0.3 |
| 2322 | Me | Ph | Ph | 1 | >10 | 9.9 | 47 ± 4 |
| 2323 | Me | Ph | p-CF₃O-Ph | 1 | 7 | 10.4 | 6.0 ± 0.5 |
| 2324 | Me | Ph | p-CF₃-Ph | 1 | >10 | 10.7 | 110 ± 5 |
| 1861 | Me | Ph | m-CF₃-Ph | 1 | 2.5 | 7.8 | 72 ± 8 |
| 2107 | NH₂ | Ph | m-CF₃-Ph | 1 | 1 | 16.9 | 84 ± 6 |
| 2106 | Me | t-butyl | m-CF₃-Ph | 1 | >10 | 2.4 | 32 ± 3 |
| 2121 | NH₂ | Ph | m-CF₃-Ph | 0 | 2 | 33.9 | 88 ± 5 |
| 2313 | NH₂ | Ph | m-CF₃-Ph | 2 | 1 | 22.0 | 26 ± 3 |
| 1862 | Me | Ph | m-CF₃-Ph | 3 | 3 | 6.4 | 3.4 ± 0.2 |
| 2246 | NH₂ | Ph | m-CF₃-Ph | 3 | 0.71 | 27.2 | 4.1 ± 0.4 |
| 2152 | NH₂ | p-Me-Ph | m-CF₃-Ph | 3 | 2.8 | 12.1 | 10 ± 1 |
| 2325 | NH₂ | Ph | 2,6-diMe-Ph | 3 | >10 | 6.2 | 1550 ± 70 |
| 2245 | NH₂ | Ph | Ph | 3 | >10 | 15.8 | 0.8 ± 0.1 |
| 2326 | NH₂ | Ph | 1-Adamantyl | 3 | 7 | 6.7 | 0.5 ± 0.1 |
| 2247 | NH₂ | Ph | c-Hep | 3 | 2 | 10.2 | 0.5 ± 0.1 |
| 2327 | NH₂ | Ph | p-Cl-Ph | 3 | 6 | 15.2 | 0.8 ± 0.1 |
| 2328 (SHH07009A) | NH₂ | Ph | p-CF₃-Ph | 3 | 1.26 | 22.7 | 0.9 ± 0.1 |
| 2329 (SHH07009B) | NH₂ | Ph | p-CF₃O-Ph | 3 | 0.92 | 13.8 | 0.5 ± 0.1 | compound 2325 (4-(3-{3-[3-(2,6-Diisopropyl-phenyl)-ureido]-propyl}-5-phenyl-pyrazol-1-yl)-benzenesulfonamide), compound 2245 (4-{5-Phenyl-3-[3-(3-phenyl-ureido)-propyl]-pyrazol-1-yl}-benzenesulfonamide), compound 2326 (4-{3-[3-(3-Adamantan-1-yl-ureido)-propyl]-5-phenyl-pyrazol-1-yl}-benzenesulfonamide), compound 2247 (4-{3-[3-(3-Cycloheptyl-ureido)-propyl]-5-phenyl-pyrazol-1-yl}-benzenesulfonamide), compound 2327 (4-(3-{3-[3-(4-Chloro-phenyl)-ureido]-propyl}-5-phenyl-pyrazol-1-yl)-benzenesulfonamide), compound 2328 (4-(5-Phenyl-3-{3-[3-(4-trifluoromethyl-phenyl)-ureido]-propyl}-pyrazol-1-yl)-benzenesulfonamide); and compound 2329 (4-(5-Phenyl-3-{3-[3-(4-trifluoromethoxy-phenyl)-ureido]-propyl}-pyrazol-1-yl)-benzenesulfonamide).

In various embodiments, a compound with combined functionality to concurrently inhibit sEH and phosphodiesterase 4 (PDE4) is administered. Dual inhibitors of PDE4 and soluble epoxide hydrolase are described, e.g., in co-pending and co-owned U.S. Provisional Appl. No. 62/574,908, filed on Oct. 20, 2017 and entitled "ORALLY AVAILABLE sEH/PDE4 DUAL INHIBITORS FOR TREATMENT OF INFLAMMATORY PAIN," which is hereby incorporated herein by reference in its entirety for all purposes.

A general structure of inhibitors that inhibit both PDE4 and sEH are provided below, in Table 5.

TABLE 5

Evaluation of dual sEH/PDE4 inhibitors in vitro activity

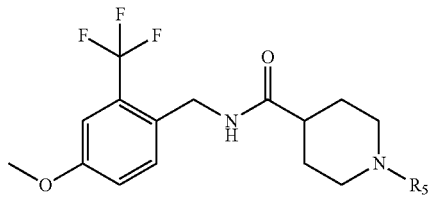

| ID | $R_1$ | $R_2$ | $IC_{50}{}^a$ [nM] | cAMP increase$^b$ (% of Rolipram) | w.s.$^c$ [nM] |
|---|---|---|---|---|---|
| 1 | $CF_3$ | OMe | 0.6 ± 0.1 | 240 ± 14 | 37.5 |
| 2 | $CF_3$ | — | 15 ± 3 | 180 ± 12 | 37.5 |
| 3 | Me | — | 180 ± 40 | 200 ± 11 | 37.5 |
| 4 | — | — | 2 ± 0.9 | 160 ± 12 | 100 |
| 5 | F | — | 2.8 ± 0.4 | 110 ± 13 | 100 |
| 6 | — | NHCOMe | 2.9 ± 1.1 | 140 ± 15 | 100 |
| 7 | — | NHCOEt | 3.7 ± 1 | 150 ± 18 | 50 |
| 8 | Me | NHCOMe | 13 ± 2 | 140 ± 15 | 20 |
| 9 | pyrrolidin-2-one | | 3 ± 2 | 130 ± 25 | 100 |
| 10 | NHCOMe | — | 44 ± 5 | 100 ± 19 | 50 |
| 11 | OMe | — | 1 ± 0.2 | 160 ± 17 | 100 |
| 14 | $OCHF_2$ | — | 1.5 ± 0.4 | 150 ± 14 | 10 |
| 19 | — | $OcC_5H_9$ | 0.4 ± 0.1 | 147 ± 9 | 10 |
| 20 | F | $OcC_5H_9$ | 0.4 ± 0 | 222 ± 8 | 100 |

| ID | $R_5$ | $IC_{50}{}^a$ [nM] | cAMP increase$^b$ (% of Rolipram) | w.s.$^c$ [nM] |
|---|---|---|---|---|
| TPPU$^D$ | — | 3.7 | 40 ± 10 | 200 |
| 21 | BOC | 1.7 ± 0.7 | 100 ± 12 | 100 |
| 22 | — | 370 ± 170 | 138 ± 5 | 1000 |
| 23/MPPA | COEt | 2.1 ± 0.5 | 200 ± 19 | 100 |
| 24 | COPr | 4 ± 2 | 110 ± 16 | 50 |
| 25 | s-Bu | 7 ± 3 | 160 ± 11 | 0.5 |
| 26 | Et | 109 ± 16 | 60 ± 10 | 1000 |
| 27 | n-Pr | 190 ± 20 | 60 ± 14 | 1000 |

In vitro evaluation of sEH/PDE4 dual inhibitors Group 1: 1-3, Group 2: 4-11, 14, 19-20 and Group 3: 21-27. $^a$The sEH IC50 values were recorded on recombinant human sEH protein (hsEH) using PHOME as substrate at 5 μM concentration30; $^b$ PDE4 inhibition was evaluated by cAMP increase in live human embryonic kidney (HEK) cells, transfected with a PKA biosensor and visualized relative to Rolipram at 1 μM; $^c$water solubility (w.s.) is measured in sodium phosphate buffer (0.1 M, pH 7.4) with 1% DMSO by precipitation.

In some embodiments, the dual inhibitor of PDE4 and sEH is a compound in Table 5 selected from the group consisting of:

compound 1; 3-(Cyclopentyloxy)-4-methoxy-N-(4-methoxy-2-(trifluoromethyl)benzyl)benzamide;
compound 2; 3-(Cyclopentyloxy)-4-methoxy-N-(2-(trifluoromethyl)benzyl)benzamide;
compound 3; 3-(Cyclopentyloxy)-4-methoxy-N-(2-methylbenzyl)benzamide;
compound 4; N-(4-Methoxy-2-(trifluoromethyl)benzyl)benzamide;
compound 5; 4-Fluoro-N-(4-methoxy-2-(trifluoromethyl)benzyl)benzamide;
compound 6; 3-Acetamido-N-(4-methoxy-2-(trifluoromethyl)benzyl)benzamide;
compound 7; N-(4-Methoxy-2-(trifluoromethyl)benzyl)-3-propionamidobenzamide;
compound 8; 3-Acetamido-N-(4-methoxy-2-(trifluoromethyl)benzyl)-4-methylbenzamide;
compound 9; N-(4-Methoxy-2-(trifluoromethyl)benzyl)-2-oxoindoline-6-carboxamide;
compound 10; 4-Acetamido-N-(4-methoxy-2-(trifluoromethyl)benzyl)benzamide;
compound 11; 4-Methoxy-N-(4-methoxy-2-(trifluoromethyl)benzyl)benzamide;
compound 14; 4-(Difluoromethoxy)-N-(4-methoxy-2-(trifluoromethyl)benzyl)benzamide;
compound 19; 3-(Cyclopentyloxy)-N-(4-methoxy-2-(trifluoromethyl)benzyl)benzamide;
compound 20; 3-(Cyclopentyloxy)-4-fluoro-N-(4-methoxy-2-(trifluoromethyl)benzyl)benzamide;
compound 21; tert-Butyl 4-((4-methoxy-2-(trifluoromethyl)benzyl)carbamoyl)piperidine-1-carboxylate;
compound 22; N-(4-Methoxy-2-(trifluoromethyl)benzyl)piperidine-4-carboxamide;
compound 23; N-(4-methoxy-2-(trifluoromethyl)benzyl)-1-propionylpiperidine-4-carboxamide (MPPA);
compound 24; 1-Butyryl-N-(4-methoxy-2-(trifluoromethyl)benzyl)piperidine-4-carboxamide;
compound 25; N-(4-Methoxy-2-(trifluoromethyl)benzyl)-1-(2-methylbutanoyl)piperidine-4-carboxamide;
compound 26; 1-Ethyl-N-(4-methoxy-2-(trifluoromethyl)benzyl)piperidine-4-carboxamide; and
compound 27; N-(4-Methoxy-2-(trifluoromethyl)benzyl)-1-propylpiperidine-4-carboxamide.

6. Formulation and Administration

In some embodiments, the sEHI is administered as the sole active agent. In various embodiments of the compositions, the sEHI is co-administered with the second agent (e.g., COX-2 inhibitor, PDE4 inhibitor, inhibitor of ER stress, inhibitor of ER stress, carbidopa/levodopa, dopamine agonists, and monoamine oxidase type B (MAO-B) inhibitors). In some embodiments, the sEHI is not co-administered with an inhibitor of ER stress, e.g., is not co-administered with 4-phenyl butyric acid (4-PBA), 3-phenylpropionic acid (3-PPA), 5-phenylvaleric acid (5-PVA), 6 phenylhexanoic acid (6-PHA), esters thereof (e.g., esters of 4-phenyl butyric acid (4-PBA), 3-phenylpropionic acid (3-PPA), 5-phenylvaleric acid (5-PVA), 6 phenylhexanoic acid (6-PHA)), pharmaceutically acceptable salts thereof (e.g., salts of 4-phenyl butyric acid (4-PBA), 3-phenylpropionic acid (3-PPA), 5-phenylvaleric acid (5-PVA), 6 phenylhexanoic acid (6-PHA)), or mixtures thereof.

The sEHI and the second agent (e.g., COX-2 inhibitor, PDE4 inhibitor, inhibitor of ER stress, carbidopa/levodopa, dopamine agonists, and monoamine oxidase type B (MAO-B) inhibitors) independently can be prepared and administered in a wide variety of oral, parenteral and topical dosage forms. The sEHI and the second agent (e.g., COX-2 inhibitor, PDE4 inhibitor, inhibitor of ER stress, carbidopa/levodopa, dopamine agonists, and monoamine oxidase type B (MAO-B) inhibitors) can be administered via the same or different routes of administration. In various embodiments, the sEHI and the second agent (e.g., COX-2 inhibitor, PDE4 inhibitor, inhibitor of ER stress, carbidopa/levodopa, dopamine agonists, and monoamine oxidase type B (MAO-B) inhibitors) independently can be administered orally, by injection, that is, intravenously, intramuscularly, intracutaneously, subcutaneously, intraduodenally, or intraperitoneally. The sEHI and the second agent (e.g., COX-2 inhibitor, PDE4 inhibitor, inhibitor of ER stress, carbidopa/levodopa, dopamine agonists, and monoamine oxidase type B (MAO-B) inhibitors) can also be administered by inhalation, for example, intranasally. Additionally, the sEHI and the second agent (e.g., COX-2 inhibitor, PDE4 inhibitor, inhibitor of ER stress, carbidopa/levodopa, dopamine agonists, and monoamine oxidase type B (MAO-B) inhibitors) can be administered transdermally.

In various embodiments, one or both of the sEHI, and/or the second agent (e.g., COX-2 inhibitor, PDE4 inhibitor, inhibitor of ER stress, carbidopa/levodopa, dopamine agonists, and monoamine oxidase type B (MAO-B) inhibitors) are specifically, predominantly or preferentially targeted to the brain. Methods for preferentially targeting therapeutic agents to brain tissues are known in the art and find use. Illustrative strategies useful for targeted and/or enhanced delivery of organic compounds and oligonucleotides to the brain are discussed in, e.g., Hanson, et al., *BMC Neurosci.* (2008) 9 Suppl 3:S5; Kim, et al., *Mol Ther.* (2012) 20(4): 829-39; Gong, et al., *Biomaterials.* (2012) 33(12):3456-63; Gomez, et al., *Front Biosci* (Schol Ed). (2012) 4:74-89; Patel, et al., *CNS Drugs.* (2009) 23(1):35-58; Fonseca-Santos, et al., *Int J Nanomedicine.* (2015) 10:4981-5003; Sela, et al., *J Nanobiotechnology.* (2015) Oct. 21; 13:71; and Rajadhyaksha, et al., *Curr Drug Discov Technol.* (2011) 8(2):87-101.

In various embodiments, in order to enhance delivery to the brain, the one or more agents or compounds can be co-administered with, conjugated to or encapsulated within an agent that facilitate transport across the blood-brain-barrier. Strategies and agents useful for facilitating delivery across the blood-brain-barrier are known in the art and can be employed in the present methods. Current strategies for delivering active agents across the blood-brain barrier and that find use in the present methods include without limitation nanocarriers and nanoparticles (Tam, et al., *Int J Pharm.* (2016) 515(1-2):331-342; Zhao, et al., *Nanoscale Res Lett.* 2016 December; 11(1):451; Song, et al., *Mol Pharm.* (2016) Oct. 4; PMID: 27700119; Lalatsa, et al., *Int Rev Neurobiol.* 2016; 130:115-53; Kundo, et al., ACS *Chem Neurosci.* (2016) Oct. 3; PMID: 27642670); functionalized carbon nanotubes (Costa, et al., *J Control Release.* (2016) 241:200-219); nanowires (Sharma, et al., *CNS Neurol Disord Drug Targets.* 2016 Aug. 19; PMID: 27538949); viral vectors (Fu, et al., *Curr Opin Virol.* (2016) 21:87-92); liposomes and exosomes (Tremmel, et al., *Int J Pharm.* (2016) 512(1):87-95; Sanchez-Purra, et al., *Int J Pharm.* (2016) 511(2):946-56; Bender, et al. *J Vis Exp.* (2016) Jul. 23;(113). doi: 10.3791/54106; Ha, et al., *Acta Pharm Sin B.* (2016) 6(4): 287-96); dendrimers (Jiang, et al, *Colloids Surf B Biointerfaces.* (2016) 147:242-9) and ultrasound (Park, et al., *J Control Release.* (2016) Oct. 11. pii: SO168-3659(16)

30955-5; Airan, et al., *Mol Imaging Biol.* (2016) Aug. 1; PMID: 27481359). In various embodiments, the one or more compounds can be conjugated to or administered in conjunction with a peptide that promotes transcytosis and traversal of the blood-brain barrier. Illustrative peptides include without limitation Angiopep-2 (Li, et al., *Oncotarget.* 2016 Oct. 17. doi: 10.18632; PMID: 27765902); Transferrin (Nanoscale. (2016) 8(37):16662-16669); penetratin (Spencer, et al., *Ann Clin Transl Neurol.* (2016) 3(8):588-606); and M36 fungalysin metalloprotease (WO 2013/036827).

Furthermore, the sEHI and the second agent (e.g., COX-2 inhibitor, PDE4 inhibitor, inhibitor of ER stress, carbidopa/levodopa, dopamine agonists, and monoamine oxidase type B (MAO-B) inhibitors) can be co-formulated in a single composition or can be formulated for separate co-administration. Accordingly, in some embodiments, the methods contemplate administration of compositions comprising a pharmaceutically acceptable carrier or excipient, an sEHI, and optionally the second agent (e.g., COX-2 inhibitor, PDE4 inhibitor, inhibitor of ER stress, carbidopa/levodopa, dopamine agonists, and monoamine oxidase type B (MAO-B) inhibitors). In some embodiments, the methods comprise administration of an sEHI and one or more epoxides of EPA or of DHA, or of both.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets can contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, polyethylene glycols and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, NY: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®, substances such as menthol, oil of wintergreen, camphor, or eucalyptus oil compounds which, when applied to skin over an area presumably alter or off-set pain in joints or muscles served by the same nerves) and salicylates (e.g. BenGay®), are known and can be readily adapted for topical administration of sEHI by replacing the active ingredient or ingredient with an sEHI, with or without EETs. It is presumed that the person of skill is familiar with these various vehicles and preparations and they need not be described in detail herein.

The sEHI can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, FL, 1997).

In some embodiments, the agents are in a cream. Typically, the cream comprises one or more hydrophobic lipids, with other agents to improve the "feel" of the cream or to provide other useful characteristics. In one embodiment, for example, a cream may contain 0.01 mg to 10 mg of sEHI, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In various embodiments, sEHI, and/or the second agent (e.g., COX-2 inhibitor, PDE4 inhibitor, inhibitor of ER stress, carbidopa/levodopa, dopamine agonists, and monoamine oxidase type B (MAO-B) inhibitors) can be mixed into a commercially available cream, Vanicream® (Pharmaceutical Specialties, Inc., Rochester, MN) comprising purified water, white petrolatum, cetearyl alcohol and ceteareth-20, sorbitol solution, propylene glycol, simethicone, glyceryl monostearate, polyethylene glycol monostearate, sorbic acid and BHT.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

Whatever the form in which the agents that inhibit sEH are topically administered (that is, whether by solid, liquid, lotion, gel, spray, etc.), in various embodiments they are administered at a therapeutically effective dosage of about 0.01 mg to 10 mg per 10 cm$^2$. An exemplary therapeutically effective dose for systemic administration of an inhibitor of sEH is from about 0.1 µg/kg to about 100 mg/kg, e.g., about 0.001 mg/kg to about 10 mg/kg, e.g., about 0.01 mg/kg to about 1.0 mg/kg, body weight of the mammal. In various embodiments, dose and frequency of administration of an sEH inhibitor are selected to produce plasma concentrations within the range of 2.5 µM and 30 nM.

The sEHI can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The pharmaceutical preparation can be in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification.

A therapeutically effective amount or a sub-therapeutic amount of the sEHI can be co-administered with the second agent (e.g., inhibitor of ER stress, carbidopa/levodopa, dopamine agonists, and monoamine oxidase type B (MAO-B) inhibitors). The dosage of the specific compounds depends on many factors that are well known to those skilled in the art. They include for example, the route of administration and the potency of the particular compound. An exemplary therapeutically effective dose is from about 0.1 µg/kg to about 100 mg/kg, e.g., about 0.001 mg/kg to about 10 mg/kg, e.g., about 0.01 mg/kg to about 1.0 mg/kg, body weight of the mammal. Determination of an effective amount is well within the capability of those skilled in the art, especially in light of the detailed disclosure provided herein. Generally, an efficacious or effective amount of a combination of one or more agents is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the one or more agents are described, for example, in *Goodman and Gilman's The Pharmacological Basis of Therapeutics,* 13th Edition, 2017, McGraw-Hill; in Physicians' Desk Reference (PDR), 71st Edition, 2017, PDR Network; in *Remington: The Science and Practice of Pharmacy,* 22nd Ed., 2012, supra; and in Brayfield, *Martindale: The Complete Drug Reference,* 39th Edition., 2017, Pharmaceutical Press, each of which are hereby incorporated herein by reference.

7. Methods of Monitoring

Clinical efficacy can be monitored using any method known in the art. Measurable parameters to monitor efficacy will depend on the condition being treated. For monitoring the status or improvement of one or more symptoms associated with a neurodegenerative illness, both subjective parameters (e.g., patient reporting) and objective parameters (e.g., reduction or elimination of motor and/or cognitive impairment symptoms and/or other symptoms associated with the neurodegenerative illness observable by a clinician; tissue biomarker levels, brain scans; motor, balance and gait functions; cognitive functions. Symptoms for patients with neurodegenerative illness associated with, caused and/or mediated at least in part by alpha-synuclein deposits can be measured and quantified using appropriate tests and scales established in the art, e.g., Hoehn and Yahr staging, Clinical Impression of Severity Index for PD, NMS Scale, NMS Questionnaire, and Movement Disorder Society (MDS)-Unified Parkinson's Disease Rating Scale (UPDRS). See, Martinez-Martin, et al., *Expert Rev Neurother.* 2018 January;18(1):41-50. Applicable assays or diagnostic parameters for the monitoring neurodegenerative illness such as Parkinson's Disease are known in the art, e.g., as set forth in the MDS-UPDRS, described in, e.g., Goetz, et al., *Mov Disord.* 2008 Nov. 15; 23(15):2129-70; and Martinez-Martin, et al., *Parkinsonism Relat Disord.* 2015 January;21(1):50-4. Behavioral changes in the subject (e.g., attitude, mood, appetite, grooming, sociability, energy levels, increased activity levels, weight gain/loss, exhibition of increased comfort) are also relevant to neurodegenerative disorders having depressive symptoms. These parameters can be measured using any methods known in the art. In various embodiments, the different parameters can be assigned a score. Further, the scores of two or more parameters can be combined to provide an index for the subject.

Observation of the stabilization, improvement and/or reversal of one or more symptoms or parameters by a measurable amount indicates that the treatment or prevention regime is efficacious. Observation of the progression, increase or exacerbation of one or more symptoms indicates that the treatment or prevention regime is not efficacious. For example, in the case of a neurodegenerative illness (e.g., Parkinson's, Dementia with Lewy Bodies, Alzheimer's), observation the improvement of one or both of subjective parameters (e.g., patient reporting) and objective parameters (e.g., reduction or elimination of motor impairment and/or cognitive symptoms and/or other symptoms associated with the neurodegenerative illness observable by a clinician; tissue biomarker levels, brain scans; motor, gait and/or cognitive functions (e.g., verbal learning, speed of processing, attention/vigilance, working memory, visual learning, reasoning and problem solving, social cognition)) and/or behavioral changes in the subject (e.g., attitude, mood, appetite, grooming, sociability, energy levels, increased activity levels, weight gain/loss, exhibition of increased comfort) after one or more co-administrations of the sEHI indicates that the treatment or prevention regime is efficacious. Likewise, observation of reduction or decline, lack of improvement or worsening of one or both of subjective parameters (e.g., patient reporting) and objective parameters (e.g., reduction or elimination of depressive symptoms and/ or other symptoms associated with the neurodegenerative illness observable by a clinician; brain scans; cognitive functions (e.g., verbal learning, speed of processing, attention/vigilance, working memory, visual learning, reasoning and problem solving, social cognition)), and/or behavioral changes in the subject (e.g., attitude, mood, appetite, grooming, sociability, energy levels, increased activity levels, weight gain/loss, exhibition of increased comfort) after one or more co-administrations of the agent that increases epoxy-fatty acids (e.g., an inhibitor of sEH) indicates that the treatment or prevention regime is not efficacious.

In certain embodiments, the monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. In certain embodiments, the individuals in the control population have not received prior treatment and do not have the disease condition subject to treatment, nor are at risk of developing the disease condition subject to treatment (e.g., do not have and are not at risk of developing a neurodegenerative illness associated with, caused and/or mediated at least in part by alpha-synuclein deposits). In such cases, if the value of the measurable biomarker or clinical parameter approaches the control value, then treatment is considered efficacious. In other embodiments, the individuals in the control population have not received prior treatment and have been diagnosed with the disease condition subject to treatment (e.g., has been diagnosed with a neurodegenerative illness associated with, caused and/or mediated at least in part by alpha-synuclein deposits). In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (i.e., more than a standard deviation) is an indicator that treatment should be resumed in the subject.

EXAMPLES

The following examples are offered to illustrate, but not to limit the claimed invention.

Example 1

Inhibition Of Soluble Epoxide Hydrolase Mitigates The Pathogenesis Of A-Synuclein-Related Neurodegenerative Disorders Materials and Methods Animals and animal care. Male adult C57BL/6 mice, aged 12 weeks (body weight 25-30 g, Japan SLC, Inc., Hamamatsu, Japan) were used. sEH KO mice (body weight 26-32 g) with targeted deletion of sEH gene (Ephx2) which is backcrossed to C57BL/6 background w used (50). Animals were housed under controlled temperatures and 12 hour light/dark cycles (lights on between 07:00-19:00 h), with ad libitum food (CE-2; CLEA Japan, Inc., Tokyo, Japan) and water. This study was carried out in strict accordance with the recommendations in the Guide for the Care and Use of Laboratory Animals of the National Institutes of Health, USA. The protocol was approved by the Chiba University Institutional Animal Care and Use Committee.

Materials. 1-Methyl-4-phenyl-1,2,3,6-tetrahydropyridine (MPTP: Tokyo Chemical Industry CO., LTD., Tokyo, Japan) was dissolved in saline. The sEH inhibitor TPPU, I-trifluoromethoxyphenyl-3-(1-propionyl)piperidin-4-yl)urea, was synthesized as previously described (32). TPPU (0.3-3.0 mg/kg) was dissolved in 10% polyethylene glycol 400 (PEG400: Wako Pure Chemical Co., Tokyo, Japan). Detailed information of antibodies used in this study was included in the Table 6. Other reagents were purchased commercially.

TABLE 6A

Primary Antibodies Used in this Example

| Antibody | | Species Isotype | Label | Dilution | Manufactor | Catalog number |
|---|---|---|---|---|---|---|
| Primary antibody | Phospho-PERK (Thr980) | Rabbit IgG | — | 1:1000 | Cell Signaling Technology | #3179 |
| | PERK | Rabbit IgG | — | 1:1000 | Cell Signaling Technology | #3192 |
| | Phospho-eIF2α(Scr51) | RabbitIgG | — | 1:1000 | Cell Signaling Technology | #3598 |
| | eIF2α | Rabbit IgG | — | 1:1000 | Cell Signaling Technology | #5324 |
| | Bip | Rabbit IgG | — | 1:1000 | Cell Signaling Technology | #3177 |
| | IRE1α(phospho S724) | Rabbit IgG | — | 1:1000 | abcam | ab18187 |
| | IRE1α | Rabbit IgG | — | 1:1000 | Cell Signaling Technology | #3294 |
| | XBP-1s | Rabbit IgG | — | 1:1000 | Cell Signaling Technology | #12782 |
| | JNK1 + JNK2 (phospho T183 + Y185) | Rabbit IgG | — | 1:1000 | abcam | ab4823 |
| | JNK1 + JNK2 | Rabbit IgG | — | 1 µg/ml | abcam | ab112501 |
| | ATFα | Rabbit IgG | — | 1:1000 | Cell Signaling Technology | #65880 |
| | Phospho-p38 MAPK (Thr180/Ty182) | Rabbit IgG | — | 1:1000 | Cell Signaling Technology | #4511 |
| | p38 MAPK | Rabbit IgG | — | 1:1000 | Cell Signaling Technology | #8690 |
| | Glutathione | Rabbit IgG | — | 1:1000 | abcam | ab19534 |

TABLE 6B

Primary Antibodies Used in this Example

| Antibody | Species Isotype | Label | Dilution | Manufacture | Catalog number |
|---|---|---|---|---|---|
| iNOS | Rabbit IgG | — | 1:500 | abcam | ab3523 |
| Superoxide Dismutase 1 | Rabbit IgG | — | 0.2 µg/ml | abcam | ab13498 |
| Tyrosine Hydroxylase | Rabbit IgG | — | 1:1000 | Merck Millipore | AB152 |
| DAT | Rat IgG | — | 1:10000 or 1:1000 | Merck Millipore | MAB368 |
| α-Symclein (phospho 8129) | Rabbit IgG | — | 1:5000 | abcam | ab51253 |
| α-Symclein | Mouse IgG | — | 1:500 | BD Transduction Laboratories | 619787 |
| mouse sEM | Rabbit IgG | — | 1:5000 | UC Davis | — |
| Human sEM | Rabbit IgG | — | 1:10000 | UC Davis | — |
| β-Actin | Mouse IgG | — | 1:10000 | Sigma-Aldrich | A5443 |
| β3-tubulin | Mouse IgG2b | — | 1:1000 | Sigma-Aldrich | T8660 |
| Tyrosine Hydroxylase | Mouse IgG1 | — | 1:500 | Sigma-Aldrich | T1299 |
| Cleaved Caspase-3 | Rabbit IgG | — | 1:400 | Cell Signaling Technology | #9661 |

TABLE 6C

Secondary Antibodies Used in this Example

| | | | | | | |
|---|---|---|---|---|---|---|
| Secondary antibody | Anti-rabbit IgG | Goat IgG | — | 1:10000 | GE healthcare | NA934 |
| | Anti-mouse IgG | Goat IgG | — | 1:10000 | GE healthcare | NA933 |
| | Anti-Rat IgG | Goat IgG | — | 1:10000 | GE healthcare | NA935 |
| | Anti-rabbit IgG | Goat IgG | Alexa Fluor 481 | 1:1000 | Invitrogen | A11070 |
| | Anti-mouse IgG2h | Goat IgG | Alexa Fluor 647 | 1:500 | Invitrogen | A21242 |
| | Anti-mouse IgG1 | Goat IgG | Alexa Fluor 488 | 1:500 | Invitrogen | A21121 |
| | Anti-rabbit IgG | Goat IgG | Alexa Fluor 556 | 1:500 | Invitrogen | A21429 |
| Other | bisBenzimide H 33258 (Hocchst) | | | | Tokyo Chemical Industry Co., Ltd | H1343 |

MPTP-induced mouse model of PD. First, mice were divided into four groups: (1): control group, (2-4): MPTP (10, 15, or 20 mg/kg×3, 2-hr interval. 9:00, 11:00 and 13:00). Seven days after administration of MPTP, mice were deeply anesthetized with isoflurane and perfused transcardially with 10 ml of isotonic saline, followed by 40 ml of ice-cold 4% paraformaldehyde in 0.1 M phosphate buffer (pH 7.4). Brains were removed from the skulls and postfixed overnight at 4° C., and brain was used for immunohistochemistry of dopamine transporter (DAT) and tyrosine hydrogenase (TH).

Second, mice were randomly divided into six groups: (1): control group, (2): MPTP groups, (3) TPPU group. MPTP (10 mg/kg×3, 2-hr interval. 9:00, 11:00 and 13:00) or saline (10 ml/kg×3, 2-hr interval) was injected into mice. Vehicle (10 ml/kg) or TPPU (0.3, 1.0, or 3 mg/kg. 19:00) was administered orally 6 hours after the final administration of saline or MPTP. Subsequently, vehicle or TPPU (3.0 mg/kg) were injected orally twice day (9:00 and 19:00) for additional 6 days (days 2-7). Mice were sacrificed on day 8, and striatum from mouse brain was collected. Brain samples were stored at 80° C. before the use of high performance liquid chromatography (HPLC).

Third, mice were divided into four groups: (1): control group, (2-4): MPTP (10 mg/kg×3, 2-hr interval). MPTP (10 mg/kg×3, 2-hr interval. 9:00, 11:00 and 13:00) or saline (10 ml/kg×3, 2-hr interval) was injected i.p. into mice. Vehicle (10 ml/kg) or TPPU (3 mg/kg) were administered orally 6 hours after the final administration of saline or MPTP. Subsequently, vehicle or TPPU (3.0 mg/kg) were injected orally twice day (9:00 and 19:00) for additional 6 days (days 2-7). On day 8, mice were deeply anesthetized with isoflurane and perfused transcardially with 10 ml of isotonic saline, followed by 40 ml of ice-cold 4% paraformaldehyde in 0.1 M phosphate buffer (pH 7.4). Brains were removed from the skulls and postfixed overnight at 4° C., and brain was used for immunohistochemistry.

Fourth, wild mice and sEH KO mice were divided into two groups, respectively. Subsequently, these two groups were divided into control group and MPTP (10 mg/kg×3, 2-hr interval. 9:00, 11:00 and 13:00). On day 8, mice were deeply anesthetized with isoflurane and perfused transcardially with 10 ml of isotonic saline, followed by 40 ml of ice-cold 4% paraformaldehyde in 0.1 M phosphate buffer (pH 7.4). Brains were removed from the skulls and postfixed overnight at 4° C., and brain was used for immunohistochemistry.

Measurement of DA, DOPAC, and HVA in mouse striatum by HPLC. Tissue levels of DA and its metabolites (DOPAC, HVA) were measured as previously reported (51, 52). Tissue samples (striatum) were homogenized in 0.2 M perchloric acid (HC104) containing 100 µM disodium EDTA and 100 ng/ml isoproterenol (internal standard), and were then centrifuged at 20,000×g for 15 min at 4° C. The supernatants were filtered through a 0.45 µm pore membrane (Millex-LH, 4 mm; Millipore, Tokyo, Japan) and were analyzed for 5-HT, 5-HIAA, DA, and DOPAC by HPLC coupled with electrochemical detection. The HPLC system consisted of a liquid chromatograph pump (EP-300, Eicom, Kyoto, Japan), a degasser (DG-300, Eicom, Kyoto, Japan), a reversed phase column (Eicompak SC-50DS 150×3.0 mm; Eicom, Kyoto, Japan), an ECD-300 electrochemical detector (Eicom, Kyoto, Japan), and a data processor (EPC-300, Eicom, Kyoto, Japan). The mobile phase was 0.1 M acetate-citric acid buffer (pH 3.5) containing 16% methanol, 5 mg/l disodium EDTA and 190 mg/l sodium octyl sulfate.

Immunohistochemistry of DAT and TH in Mouse Brains

Immunohistochemistry of DAT and TH was performed as reported previously (51-53). The mouse brain sections (Bregma 0.86-1.54 mm) were identified according to stereotaxic coordinates in Franklin and Paxinos' Mouse Brain (54). Free-floating sections were treated with 0.3% H2O2 in 0.05M Tris-HCl saline (TBS) for 30 min and blocked in TBS containing 0.2% Triton X-100 (TBST) and 1.5% normal serum for 1 hour, at room temperature. Samples were then incubated for 36 hours at 4° C., with rat anti-DAT antibody or with rabbit TH antibody (1:1,000). The sections were washed three in TBST, and processed according to the avidin-biotin-peroxidase method (Vectastain Elite ABC, Vector Laboratories, Inc., Burlingame, CA, USA). Sections were then incubated for 5 minutes in a solution of 0.15 mg/ml diaminobenzidine, containing 0.01% H2O2. The sections were mounted on gelatinized slides, dehydrated, cleared, and coverslipped under Permount® (Fisher Scientific, Fair Lawn, NJ, USA).

For immunofluorescence detection of TH, the mouse brain section (Bregma-2.92-–3.88 mm) were identified according to stereotaxic coordinates in Franklin and Paxinos' Mouse Brain (54). The brain sections were blocked in TBS containing 0.2% Triton X (TBST) and 1.5% normal serum for 1 hour at room temperature. Then, sections were incubated overnight at 4° C., with rabbit TH antibody (1:1,000, Chemicon International Inc., Temecula, CA, USA). Next day, sections were washed three times in TBST, and incubated in fluorochrome-conjugated secondary antibody diluted in antibody dilution for 2 hours at room temperature in the dark. After wash three times with TBST, the sections were coverslipped under Permount® (Fisher Scientific, Fair Lawn, NJ, USA) with Prolong® Gold Antifade Reagent (Cell Signaling Technology, USA).

The staining intensity of DAT or TH immunoreactivity in the anterior regions (0.25 mm2) of the striatum, and the number of TH-positive cells in SNc were imaged and analyzed using Keyence BZ-9000 Generation microscope (Keyence Co., Ltd, Osaka, Japan) and ImageJ software package.

Viral vector preparation and injection. The transfer plasmid (pAAV-CAGGS-Ephx2-P2A-EmGFP) was constructed by Invitrogen. The viral vectors were prepared as described previously (55). Briefly, the AAV vectors were packaged using the AAV Helper Free Expression System (Cell Biolabs, Inc., San Diego, CA). The packaging plasmids (pAAV-DJ and pHelper) and transfer plasmid (pAAV-CAGGS-Ephx2-P2A-EmGFP or pAAV-CAGGS-EGFP) were transfected into HEK293T cells using the calcium phosphate method. After 48 h incubation, AAV vector particles were obtained and purified by serial ultracentrifugation with cesium chloride. The purified particles were dialyzed with PBS, and then concentrated by ultrafiltration using an Amicon 10 k MWCO filter (Merck Millipore, Darmstadt, Germany). The copy number of the viral genome (vg) was determined by the TaqMan Universal Master Mix II (Applied Biosystems, Foster City, CA). Real-time quantitative PCR was performed in duplicate samples using the StepOne real-time PCR system as follows: 95° C. for 10 min; 40 cycles of (95° C., 15 s and 60° C., 1 min).

To induce gene expression in the striatum, AAV DJ-CAGGS-Ephx2-P2A-EmGFP or AAV DJ-CAGGS- EGFP vectors (.0×10¹² vg/ml) were stereotaxically injected into the striatum of C57BL/6 male mice at 9 weeks old by microinjection tube connected to a microinfusion pump (0.5 μl/site, 0.1 μl/min). The anteroposterior, mediolateral, and dorsoventral coordinates relative to Bregma were as follows: +1.1 mm, ±1.0 mm and −3.0 mm (54).

Western blot analysis of mouse brain samples. Western blot analysis was performed as reported previously (53,56). Mice were killed by cervical dislocation and brains were rapidly removed from the skull, and the striatum of mice were dissected on ice. The tissue samples were homogenized in Laemmli lysis buffer. 50 g of protein were measured using the DC protein assay kit (Bio-Rad), and incubated for 5 min at 95° C., with an equal volume of 125 mM Tris-HCl, pH6.8, 20% glycerol, 0.1% bromophenol blue, 10% β-mercaptoethanol, 4% sodium dodecyl sulfate, and subjected to sodium dodecyl sulfate polyacrylamide gel electrophoresis, using 7.5% AnyKD mini-gels (Mini-PROTEAN® TGX™ Precast Gel; Bio-Rad, CA, USA). Proteins were transferred onto polyvinylidenedifluoride (PVDF) membranes using a Trans Blot Mini Cell (Bio-Rad). For immunodetection, the blots were blocked with 2% BSA in TBST (TBS+0.1% Tween-20) for 1 h at room temperature (RT), and kept with primary antibodies overnight at 4° C. The following primary antibodies were used: The next day, blots were washed three times in TBST and incubated with horseradish peroxidase conjugated anti-rabbit or anti-mouse antibody (1:10,000) 1 hour, at RT. After final three washes with TBST, bands were detected using enhanced chemiluminescence (ECL) plus the Western Blotting Detection system (GE Healthcare Bioscience). Images were captured with a ChemDoc imaging system (Bio-Rad), and the immunoreactive bands were analysis by Image Lab software.

Western blot analysis of postmortem brain samples. The postmortem brain samples from DLB patients (n=10, age: 86.7±2.28 years old (range: 72-93), 9 male and 1 female) and age-matched controls (n=10, age 79.1±3.19 years old (range: 62-94), 8 male and 2 female)) were collected at Tokyo Metropolitan Geriatric Hospital and Institute of Gerontology (Tokyo, Japan). Brain samples were selected using Brain Bank for Aging Research (BBAR) Lewy bodies rating system (57). Stages III to V correspond to the symptomatic Lewy body dementia cases of PD, PD with dementia, and DLB (including DLB with Alzheimer's disease)(58). Western blot analysis of DAT, TH, α-synuclein and phosphorylated α-synuclein in the striatum was performed as described above. This study was approved by Tokyo Metropolitan Geriatric Hospital and Institute of Gerontology (Tokyo, Japan) and the Research Ethics Committee of the Graduate School of Medicine, Chiba University (Chiba, Japan).

Oxylipin profiling. Mice were divided into control group and MPTP (10 mg/kg×3, 2-hr interval. 9:00, 11:00 and 13:00). On day 8, mice were deeply anesthetized with isoflurane and brains were removed from the skulls. Striatum was dissected from brain, and the samples were stored at −80° C. before assay. Measurement of eicosanoids was performed using the previous method (59).

Human iPS cells. The control human iPSC lines 201B7 (60) and familial PD (PARK2) lines PB20 (34) were cultured on mitomycin C-treated SNL murine fibroblast feeder cells in iPSC medium, according to the previous report (60). All experimental procedures for human iPSCs were approved by the Juntendo University School of medicine Ethics committee (Approval number: 2017032).

Total RNA isolated from induced Neuron from iPSC using RNeasy mini Kit (QIAGEN), according to the manufacturer's instructions. cDNA was generated from 0.5 μg of total RNA with SuperScript® III reverse transcriptase (Invitrogen) and random Hexamers (Invitrogen). qPCR analysis was performed with SYBR premix Ex Taq II (TaKaRa) on QuantStudio 7 Flex (Applied Biosystems). Values were normalized to β-actin and were analyzed by comparative (ΔΔCt) methods. The primer sequences were as follows:

```
human sEH forward
                                    (SEQ ID NO: 34)
5'-ACTTCGTGCTCGTTCCTCAG-3', Human sEH reverse
                                    (SEQ ID NO: 35)
5'-AGTGCCCACAGTCCTCAATG-3', Human β-actin forward
                                    (SEQ ID NO: 36)
5'-TGAAGTGTGACGTGGACATC-3', Human β-actin reverse
                                    (SEQ ID NO: 37)
5'-GGAGGAGCAATGATCTTGAT-3'.
```

For the differentiation of midbrain dopaminergic (mDA) neurons, we used a previously reported method (61-63), with slight modifications. Briefly, the iPSCs were cultured in iPSC medium supplemented with 3 μM SB431542 (Tocris), 3 μM Dorsomorphin (Sigma), and 3 μM CHIR99021 (Stemgent) for 5 days. For neurosphere formation, iPSC colonies were dissociated into single cells by TrypLE Select (Life technologies) and cultured in medium hormone mix (MHM) medium (KOHJIN BIO) supplemented with B27 (Life technologies), 20 ng/ml basic fibroblast growth factor (bFGF: Pepro Tech), 2 μM SB431542 (Tocris), 5 μM Y27632 (Wako) in 4% O2. Defining the day on which neurosphere culture was started as day 0, on day 3, 3 μM CHIR99021, and 2 μM Purmorphamine (Millipore) were added to culture medium. For terminal differentiation, on day 14, neurospheres were dissociated and seeded on poly-L-ornithine (Sigma) and Fibronectin (Corning)-coated 96 well culture plates in MHM supplemented with B27, 20 ng/ml brain-derived neurotrophic factor (BDNF; Biolegend), glial cell-derived neurotrophic factor (GDNF; Pepro Tech), 200 μM ascorbic acid (Sigma), 0.5 mM dibutyryl-cAMP (Nakalai Tesque), 1 ng/ml transforming growth factor β (TGF-β: Biolegend) and 10 μM DAPT (Sigma), and cultured for 17 days before analysis. Apoptosis was quantified and evaluated by the intensity of Cleaved Caspase-3 staining using IN Cell Analyzer 2200 (GE Healthcare). The mDA neurons were incubated with 10 μM TPPU or 0.1% DMSO as controls, for 10 days. After 10 days, mDA neuron were fixed with 4% paraformaldehyde (PFA) in PBS for 30 min at room temperature. Nonspecific proteins were blocked with 5% FBS and 0.3% Triton X-100 in PBS, and stained with the following primary antibodies; β3-tubulin (1:1000; Sigma), TH (1:500; Sigma), cleaved Caspase-3 (1:400; CST). The cells were then rinsed with incubated with species specific Alexa Fluor 488-, Alexa Fluor 555-, or Alexa Fluor 647-conjugated secondary antibodies (1:500; Thermo Fisher), and Hoechst 33258 (1:5000; Sigma) for 1 h at room temperature. The well for each experimental condition was duplicated. Fixed and Stained plates mDA neuron were imaged by IN Cell Analyzer 2200 (GE Healthcare), and 25 fields were collected from each well using 20× objective. The images were analyzed by IN Cell Developer Toolbox v1.9 (GE Healthcare), and identified nuclei with Hoechst, neuronal cell body with β3-tubulin, dopaminergic neuron with TH, and apoptosis with Cleaved Caspase-3. By setting the areas of β3-tubulin and TH-positive cells, the intensity of Cleaved Caspase-3 in dopaminergic neurons was analyzed.

Statistical analysis. The data show as the mean±standard error of the mean (S.E.M.). Analysis was performed using GraphPad Prism (La Jolla, CA). Comparisons between groups were performed using the one-way analysis of variance (ANOVA) or two-way ANOVA, followed by Fisher's LSD test. Comparisons between two groups were performed using Student t-test. The P-values of less than 0.05 were considered statistically significant.

Results

Figure 1B:
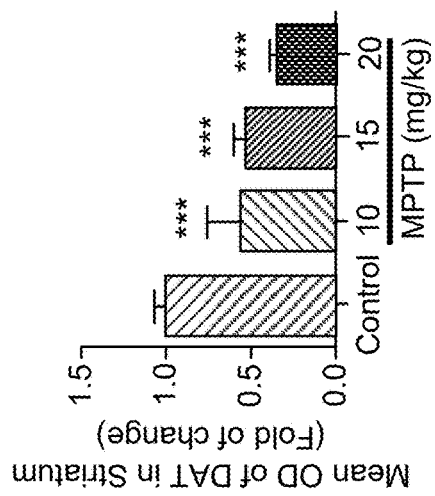
Figure 1B:
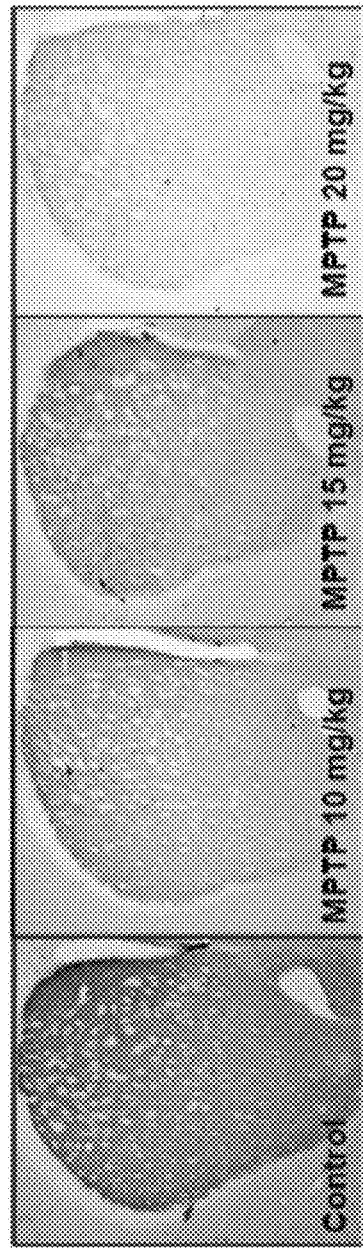
Figure 1C:
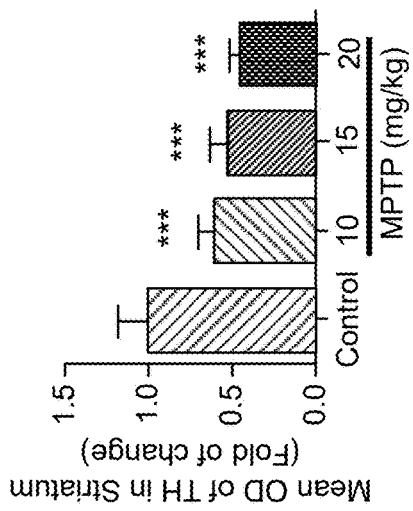
Figure 1C:
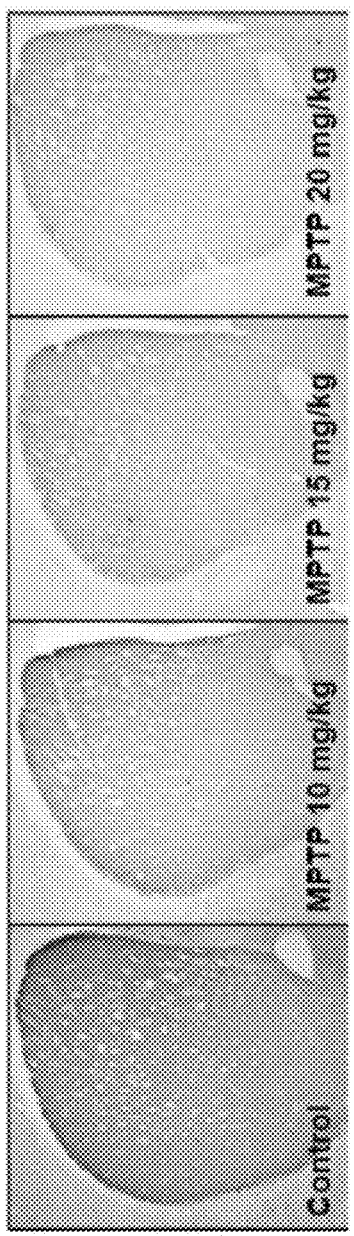
Figure 1D:
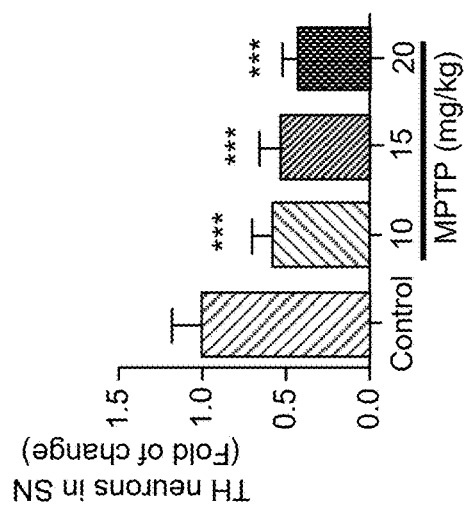
Figure 1D:
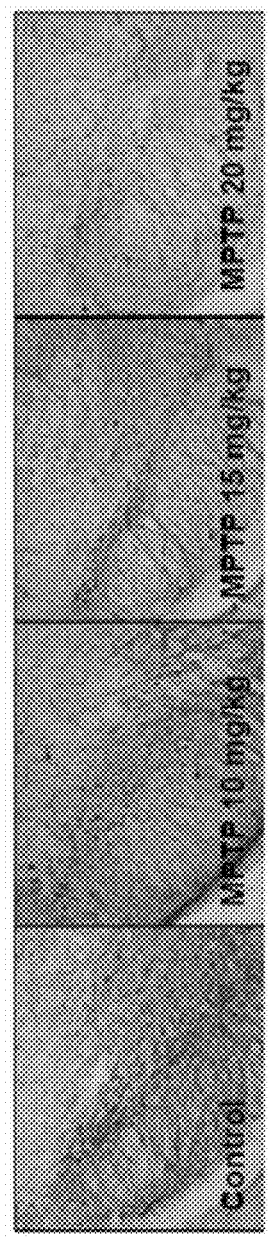

MPTP—induced neurotoxicity in the mouse brain. First, we examined the effects of MPTP on dopaminergic neurotoxicity in the mouse striatum and SN. Mice received three intraperitoneal (IP) injections of saline or MPTP [10, 15, or 20 mg/kg; 2-h intervals (9:00, 11:00, and 13:00)](FIG. 1A). For immunohistochemistry of DAT and TH, mice were perfused 7 days after MPTP injection (FIG. 1A). All doses of MPTP caused significant reductions of DAT and TH density in the striatum and TH-positive cell number in the SN compared with control mice (FIG. 1B-1D). For subsequent experiments, MPTP was administered at 10 mg/kg.

Figure 2E:
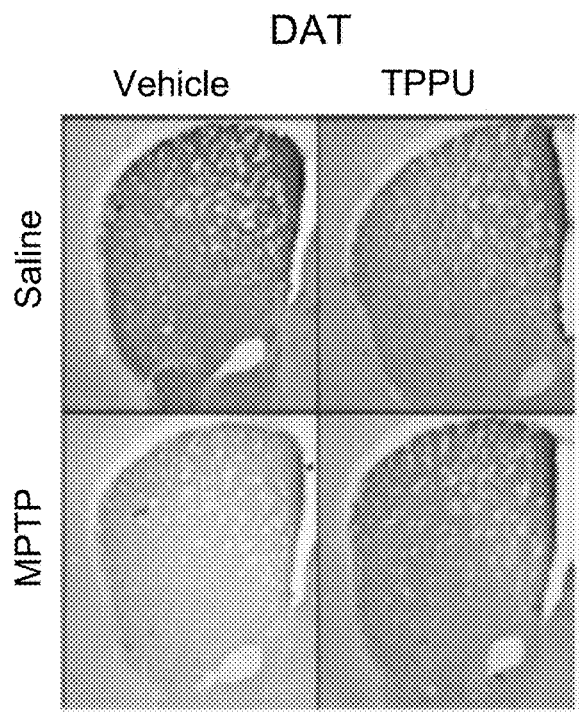
Figure 2F:
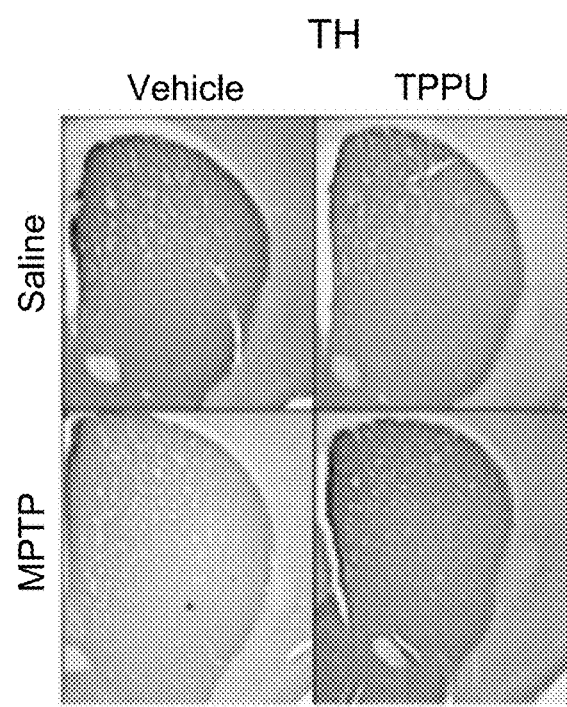

MPTP-induced neurotoxicity was attenuated after subsequent repeated administration of TPPU. We examined the effects of TPPU on MPTP-induced dopaminergic neurotoxicity in the mouse striatum. After repeated injections of saline or MPTP (10 mg/kg×3 at 2 h intervals, 9:00, 11:00, and 13:00), vehicle or TPPU (0.3, 1.0, or 3.0 mg/kg, 19:00) was administered orally to mice. Subsequently, vehicle or TPPU (0.3, 1.0, or 3.0 mg/kg, 9:00 and 19:00) was administered orally to mice from day 2-day 7 (FIG. 2A). Mice were sacrificed by decapitation on day 8 for measurement of DA and its metabolites [DOPAC (3,4-dihydroxyphenylacetic acid) and HVA (homovanillic acid)]. Repeated administration of TPPU (3 mg/kg, twice daily, PO) significantly attenuated the reduction of DA, DOPAC, and HVA in the striatum after MPTP injection, although TPPU alone did not alter the levels of these markers (FIG. 2B-2D).

Figure 2I:
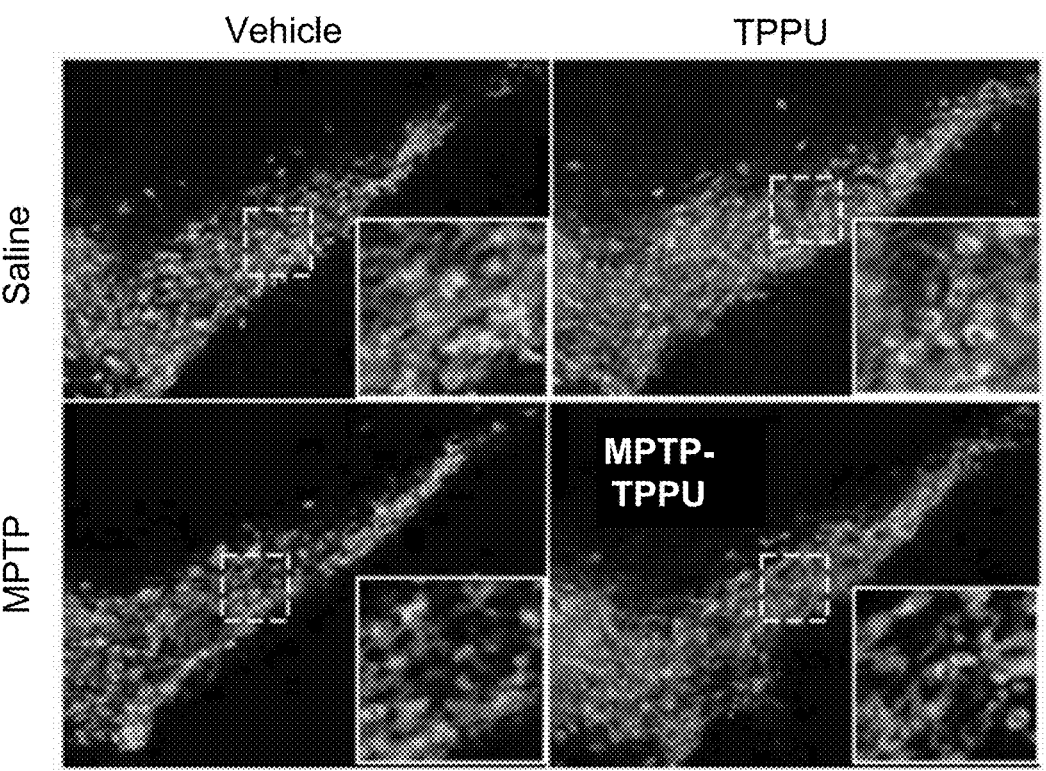
Figure 2G:
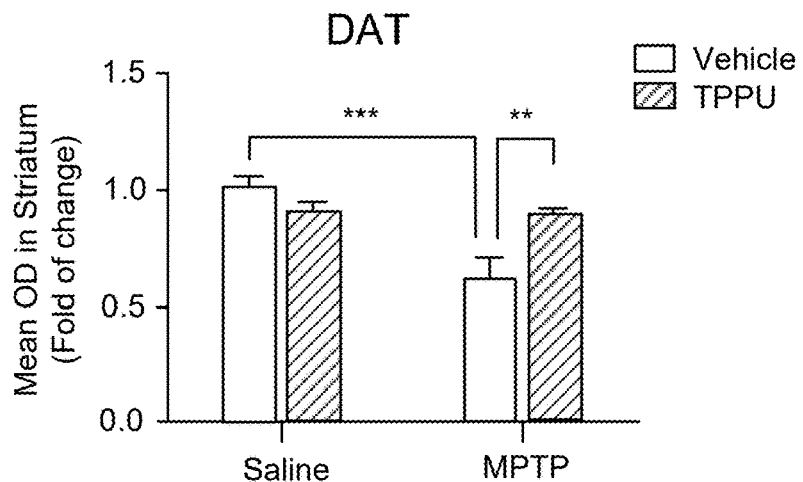
Figure 2H:
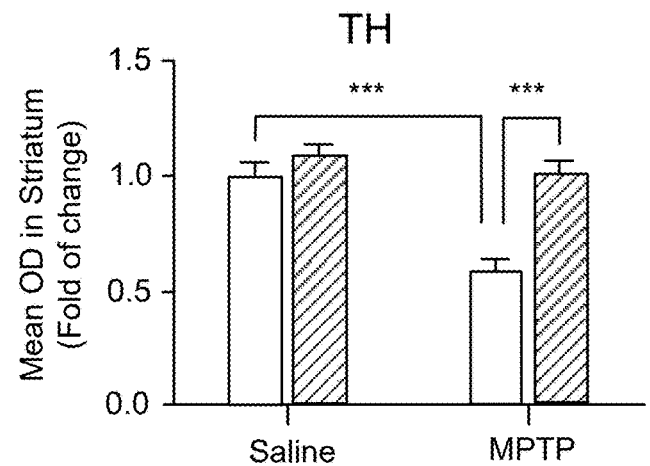
Figure 2J:
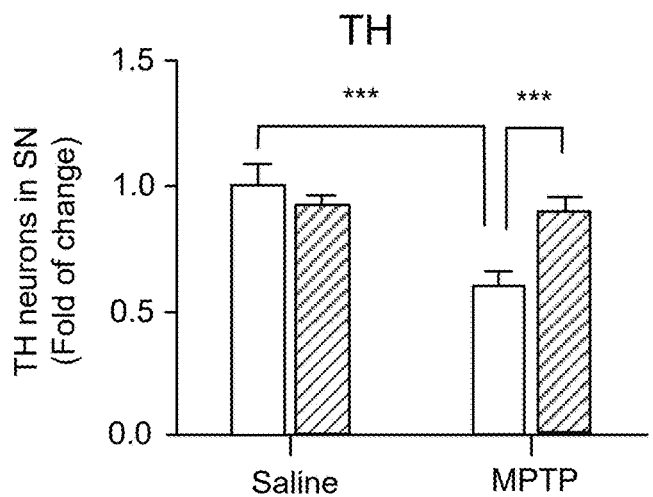

Next, we performed immunohistochemistry of DAT and TH in the striatum and SN of mouse brain samples. Repeated administration of MPTP (10 mg/kg×3 at 2 h intervals, 9:00, 11:00, and 13:00) significantly reduced DAT and TH immunoreactivity in the striatum (FIGS. 2E-2H) and the number of TH-positive cells in the SN (FIGS. 2I and 2J). Interestingly, MPTP-induced neurotoxicity in the striatum and SN was significantly attenuated after subsequent repeated administration of TPPU (3 mg/kg, 9:00 and 19:00).

Figure 3E:
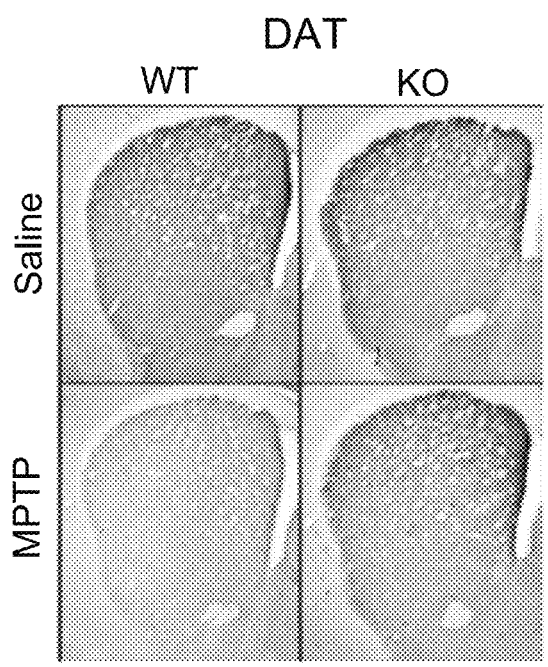
Figure 3F:
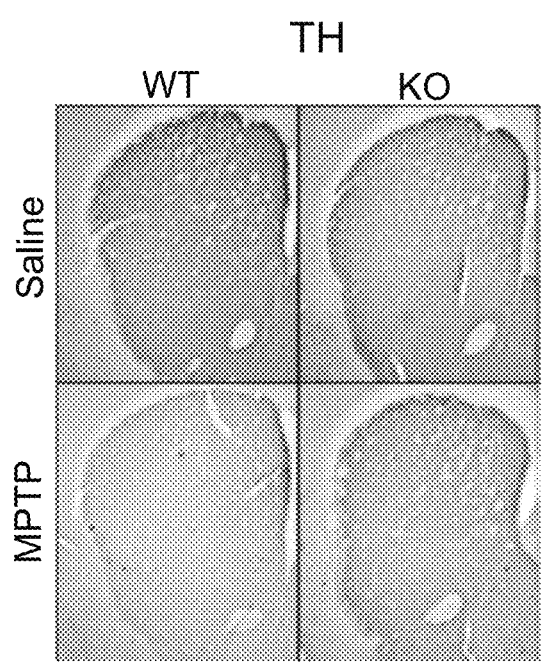
Figure 3I:
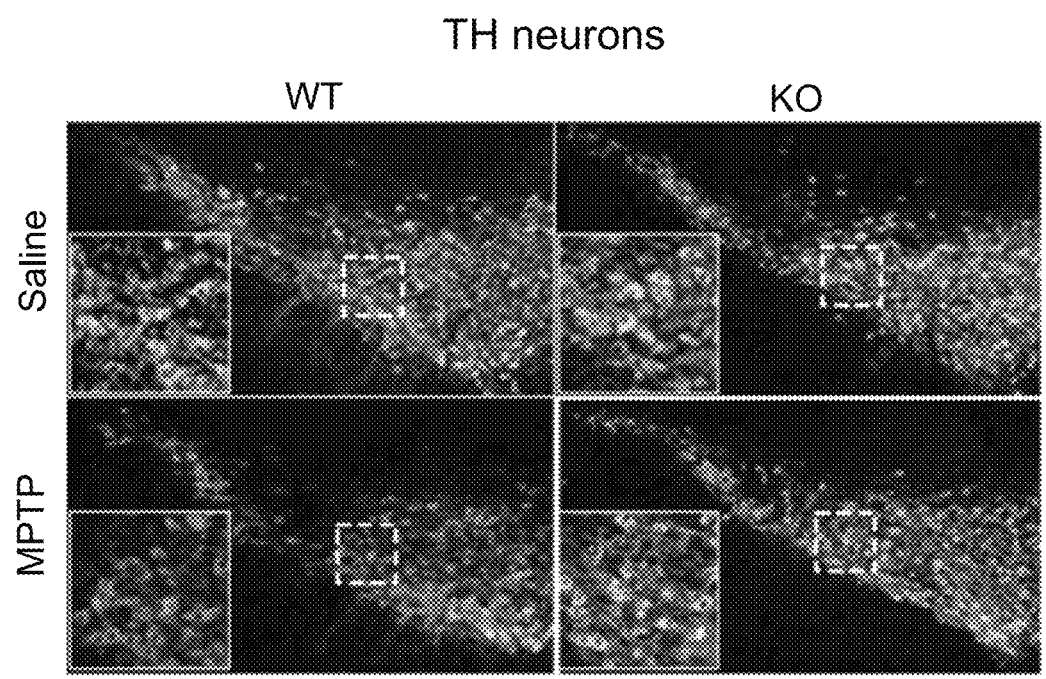
Figure 3G:
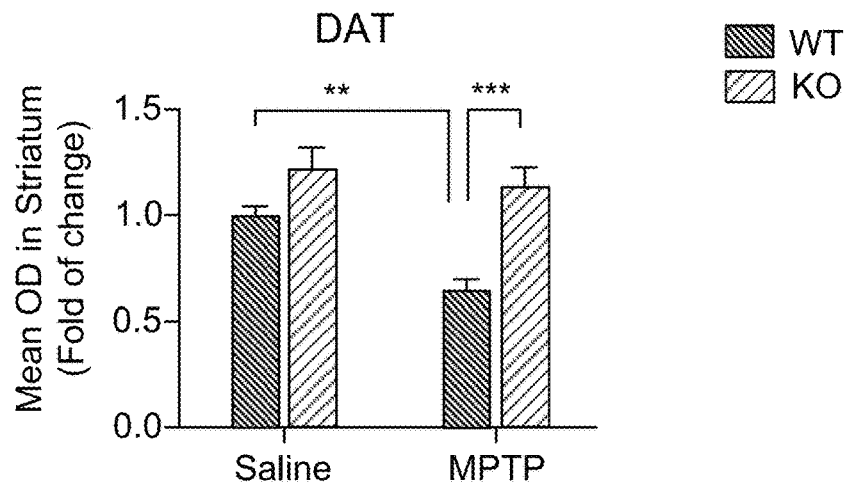
Figure 3H:
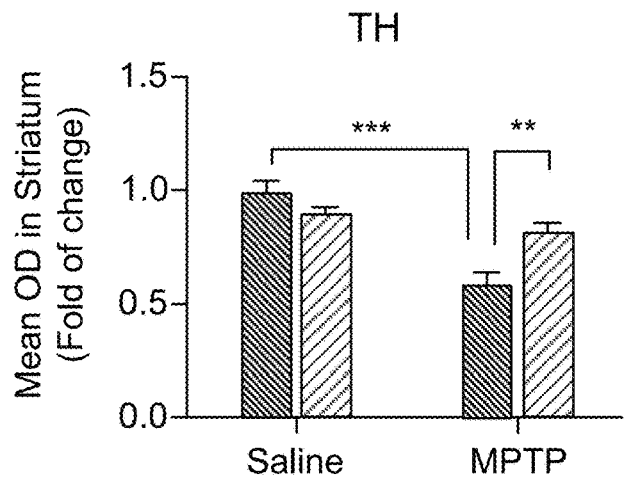
Figure 3J:
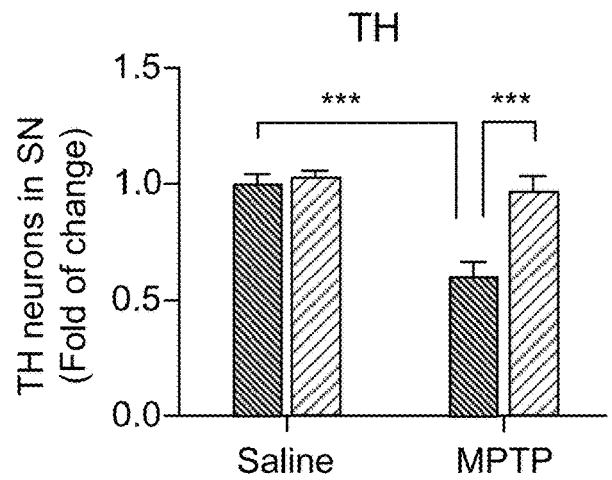

Deletion of the sEH gene protected against MPTP-induced neurotoxicity. To investigate the role of sEH in MPTP-induced neurotoxicity in the mouse brain, wild-type and sEH-KO mice received repeated injections of MPTP (10 mg/kg×3 at 2 h intervals, 9:00, 11:00, and 13:00) (FIG. 3A). Seven days after the administration of MPTP, mice were sacrificed for HPLC analysis or immunohistochemistry. Repeated administration of MPTP caused the reduction of DA and its metabolites (DOPAC and HVA) in the striatum of wild-type mice, although MPTP did not alter tissue levels of DA or its metabolites in the striatum of KO mice (FIG. 3B-3D). In addition, MPTP-induced reductions of DAT and TH in the striatum and SN were not detected in sEH KO mice (FIG. 3E-3J). These results suggest a key role of sEH in MPTP-induced neurotoxicity.

Figure 3K:
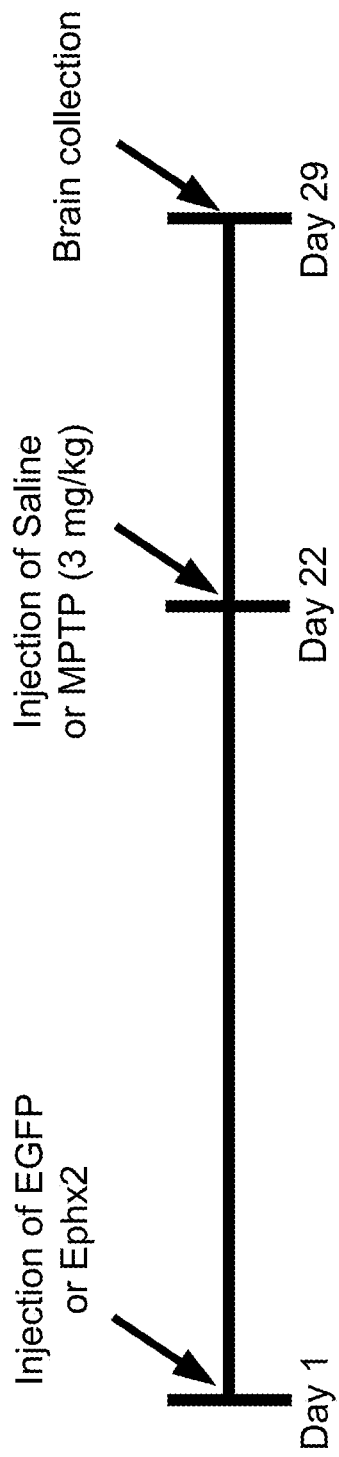
Figure 3K:
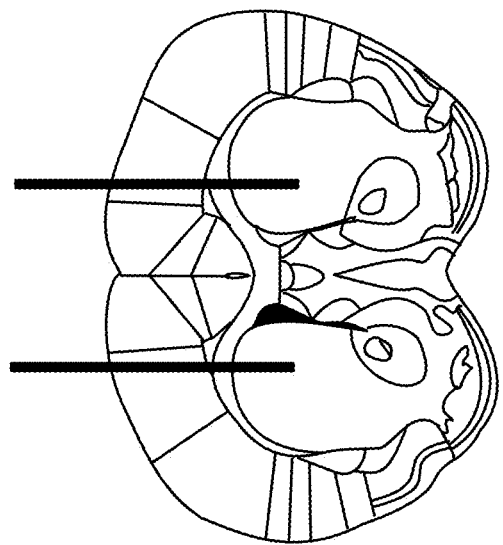
Figure 3K:
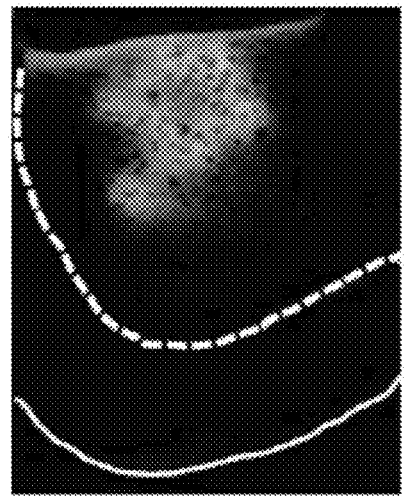
Figure 3L:
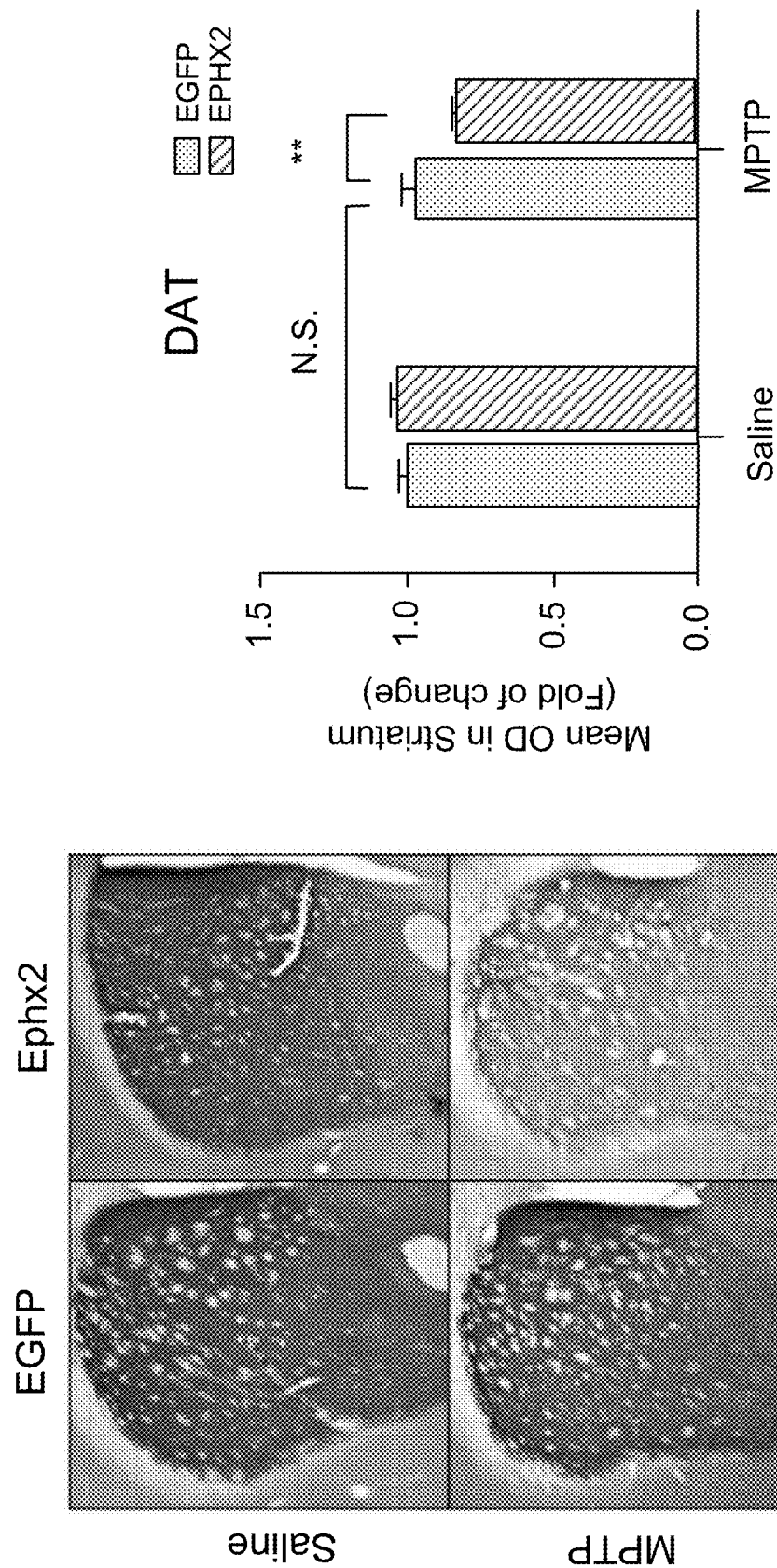

Overexpression of sEH enhanced MPTP-induced neurotoxicity. To further investigate the role of sEH in MPTP-induced neurotoxicity, we applied sEH-AAV (adeno-associated virus) to overexpress sEH in the mouse striatum (FIG. 3K). Overexpression of sEH in the striatum by AAV significantly enhanced low dose MPTP (3 mg/kg×3 at 2 h intervals, 9:00, 11:00, and 13:00)-induced neurotoxicity, although this treatment schedule did not alter DAT-immunoreactivity in the striatum of the control group (FIGS. 3K and 3L). These results suggest that increased levels of sEH play an important role in MPTP-induced dopaminergic neurotoxicity in the mouse brain.

Figure 4A:
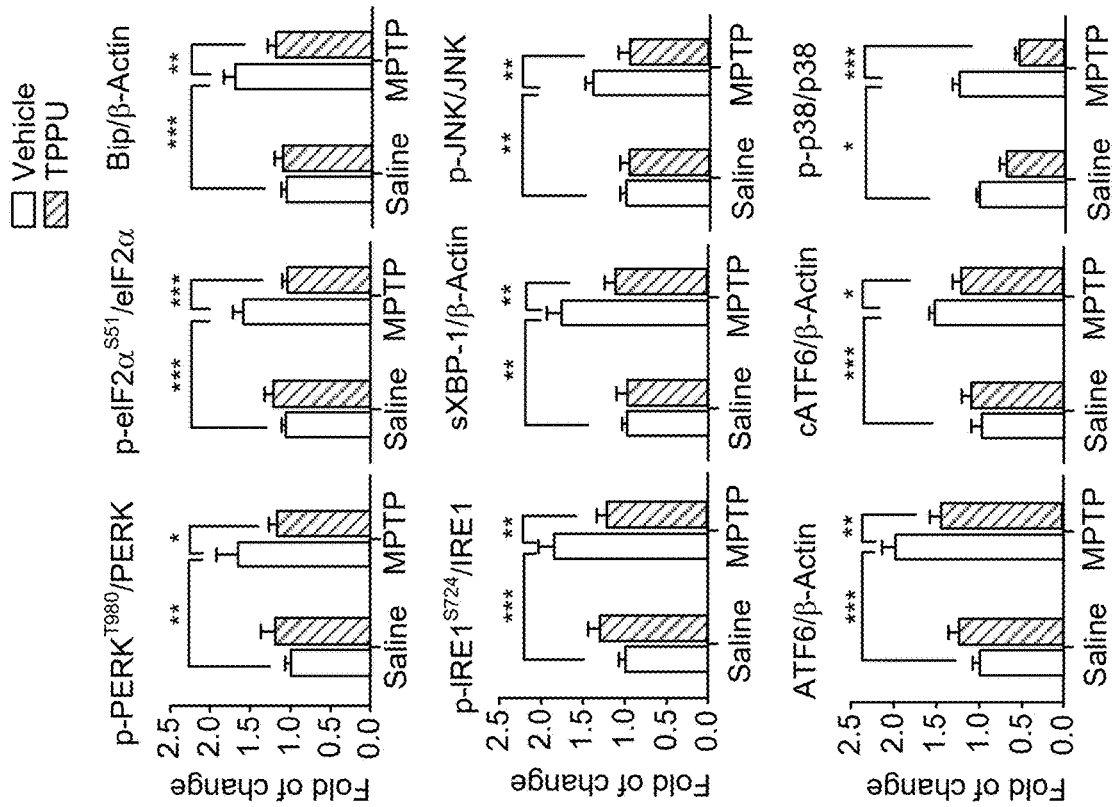
FIGS. 4A-D illustrate the effects of TPPU and deletion of sEH on elevated ER stress and oxidative stress in the MPTP-treated mice. (A): Markers of ER stress from saline or MPTP and vehicle or TPPU treated mice were measured by Western blotting. Representative immunoblots were shown from 2 mice of the four groups. Two-way ANOVA revealed the results; in the bar graphs diplayed, each pair of columns (for specific conditions tested, e.g., saline, MPTP) reports vehicle on the left and TPPU on the right (p-PERK/PERK, MPTP: $F_{1,24}$=3.784, P=0.0636, TPPU: $F_{1,24}$=0.8376, P=0.3692; interaction: $F_{1,24}$=4.600, P=0.0423), (p-eIF2α/eIF2α, MPTP: $F_{1,24}$=4.483, P=0.0448, TPPU: $F_{1,24}$=5.748, P=0.0246; interaction: $F_{1,24}$=18.67, P=0.0002), (Bip, MPTP: $F_{1,24}$=13.83, P=0.0011, TPPU: $F_{1,24}$=4.264, P=0.0499; interaction: $F_{1,24}$=6.871, P=0.0150), (p-IRE1/IRE1, MPTP: $F_{1,24}$=8.738, P=0.0069, TPPU: $F_{1,24}$=1.472, P=0.2369; interaction: $F_{1,24}$=12.80, P=0.0015), (sXBP-1, MPTP: $F_{1,24}$=11.37, P=0.0025, TPPU: $F_{1,24}$=6.163, P=0.0204; interaction: $F_{1,24}$=5.745, P=0.0247), (p-JNK/JNK, MPTP: $F_{1,24}$=3.597, P=0.070, TPPU: $F_{1,24}$=6.319, P=0.0191; interaction: $F_{1,24}$=4.528, P=0.0438), (ATF6, MPTP: $F_{1,24}$=23.36, P<0.0001, TPPU: $F_{1,24}$=1.219, P=0.2804; interaction: $F_{1,24}$=9.943, P=0.0043), (cATF6, MPTP: $F_{1,24}$=16.72, P=0.0004, TPPU: $F_{1,24}$=1.042, P=0.3175; interaction: $F_{1,24}$=6.880, P=0.0149), and (p-p38/p38, MPTP: $F_{1,24}$=0.7386, P=0.3986, TPPU: $F_{1,24}$=7.842, P=0.010; interaction: $F_{1,24}$=60.53, P<0.0001). Data are shown as mean±S.E.M. (n=7). *P<0.05, P<0.01, *P<0.001 compared to control group. (B): Markers of ER stress from WT or sEH-KO mice were treated with saline or MPTP were measured by Western blotting. Representative immunoblots were shown from 2 mice of the four groups. Two-way ANOVA revealed the results; in the bar graphs diplayed, each pair of columns (for specific conditions tested, e.g., saline, MPTP) reports WT on the left and KO on the right (p-PERK/PERK, MPTP: $F_{1,21}$=11.70, P=0.0026, KO: $F_{1,21}$=24.60, P<0.0001; interaction: $F_{1,21}$=4.472, P=0.0466), (p-eIF2α/eIF2α, MPTP: $F_{1,21}$=1.412, P=0.2486, KO: $F_{1,21}$=1.714, P=0.2053; interaction: $F_{1,21}$=4.565, P=0.0452), (Bip, MPTP: $F_{1,21}$=8.817, P=0.0073, KO: $F_{1,21}$=0.0281, P=0.8685; interaction: $F_{1,21}$=11.84, P=0.0025), (p-IRE1/IRE1, MPTP: $F_{1,21}$=15.29, P=0.0008, KO: $F_{1,21}$=18.84, P=0.0003; interaction: $F_{1,21}$=4.411, P=0.048), (sXBP-1, MPTP: $F_{1,21}$=5.806, P=0.0248, TPPU: $F_{1,21}$=9.558, P=0.0053; interaction: $F_{1,21}$=0.6413, P=0.4318,), (p-JNK/JNK, MPTP: $F_{1,21}$=8.730, P=0.0073, KO: $F_{1,21}$=3.841, P=0.0628; interaction: $F_{1,21}$=4.822, P=0.0389), (ATF6, MPTP: $F_{1,21}$=3.671 P=0.0679, KO: $F_{1,21}$=8.863, P=0.0067; interaction: $F_{1,21}$=25.40, P<0.0001), (cATF6, MPTP: $F_{1,21}$=1.308, P=0.265, KO: $F_{1,21}$=6.227, P=0.0201; interaction: $F_{1,21}$=10.92, P=0.0032), and (p-p38/p38, MPTP: $F_{1,21}$=4.274, P=0.0501, KO: $F_{1,21}$=1.095, P=0.3063; interaction: $F_{1,21}$=6.248, P=0.0197). Data are shown as mean±S.E.M. (n=6-7). *P<0.05, P<0.01, *P<0.001 compared to control group (post-hoc Tukey test). (C): Markers of oxidative stress from MPTP-treated mice were measured by Western blotting. Representative immunoblots were shown from mouse of the four groups. Two-way ANOVA revealed the results; in the bar graphs diplayed, each pair of columns (for specific conditions tested, e.g., saline, MPTP) reports vehicle on the left and TPPU on the right (GSH, MPTP: $F_{1,21}$=11.55, P=0.0026, TPPU: $F_{1,21}$=0.773, P=0.3875; interaction: $F_{1,21}$=4.456, P=0.0464), (iNOS, MPTP: $F_{1,21}$=17.10, P=0.0005, TPPU: $F_{1,21}$=14.08, P=0.0012; interaction: $F_{1,21}$=4.644, P=0.0429), (SOD, MPTP: $F_{1,21}$=5.253, P=0.0319, TPPU: $F_{1,21}$=0.0017, P=0.9676; interaction: $F_{1,21}$=12.52, P=0.0018). Data are shown as mean±S.E.M. (n=6-7). *P<0.05, ***P<0.001 compared to control group (post-hoc Tukey test). (D): Markers of oxidative stress from MPTP-treated mice were measured by Western blotting. Representative immunoblots were shown from mouse of the four groups. Two-way ANOVA revealed the results; in the bar graphs diplayed, each pair of columns (for specific conditions tested, e.g., saline, MPTP) reports WT on the left and KO on the right (GSH, MPTP: $F_{1,21}$=3.921, P=0.0609, KO: $F_{1,21}$=0.8553, P=0.3656; interaction: $F_{1,21}$=4.846, P=0.039), (iNOS, MPTP: $F_{1,21}$=8.234, P=0.0098, KO: $F_{1,21}$=0.008, P=0.0317; interaction: $F_{1,21}$=11.57, P=0.003), (SOD, MPTP: $F_{1,21}$=5.008, P=0.0347, KO: $F_{1,21}$=4.788, P=0.0414; interaction: $F_{1,21}$=1.208, P=0.2854). Data are shown as mean±S.E.M. (n=6 or 7). *P<0.05, ***P<0.001 compared to control group.
Figure 4A:
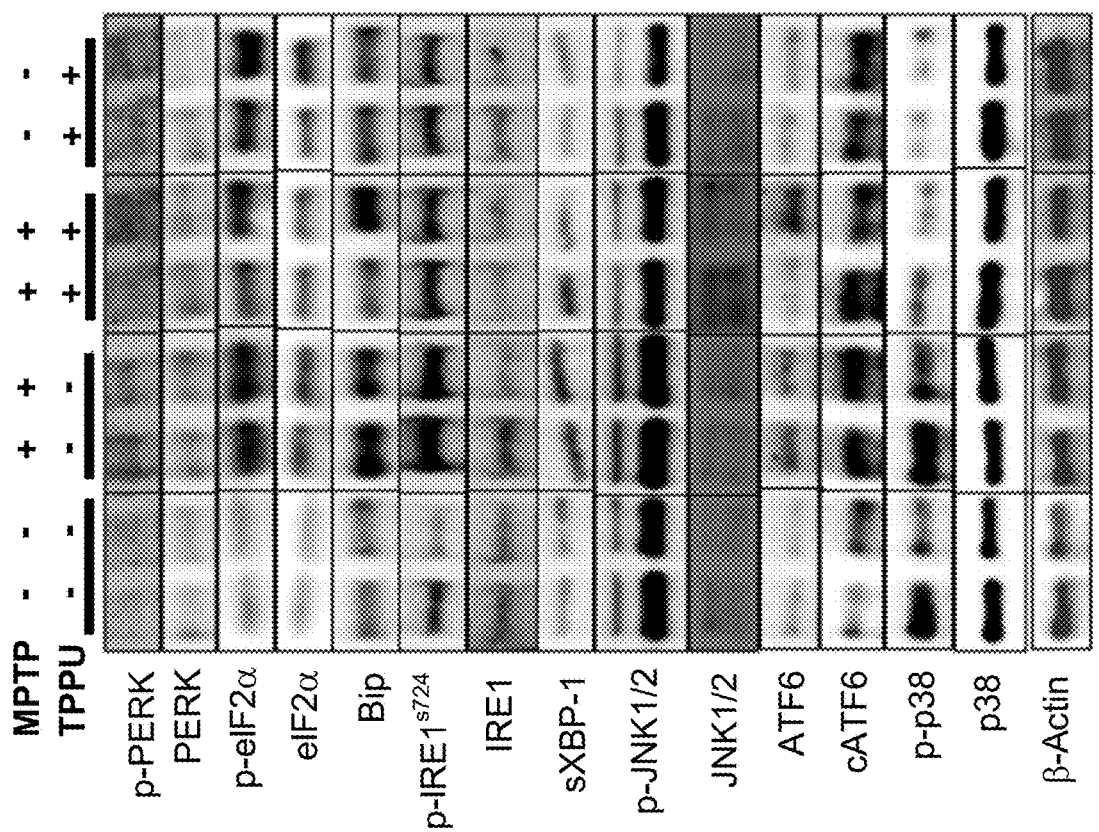
Figure 4B:
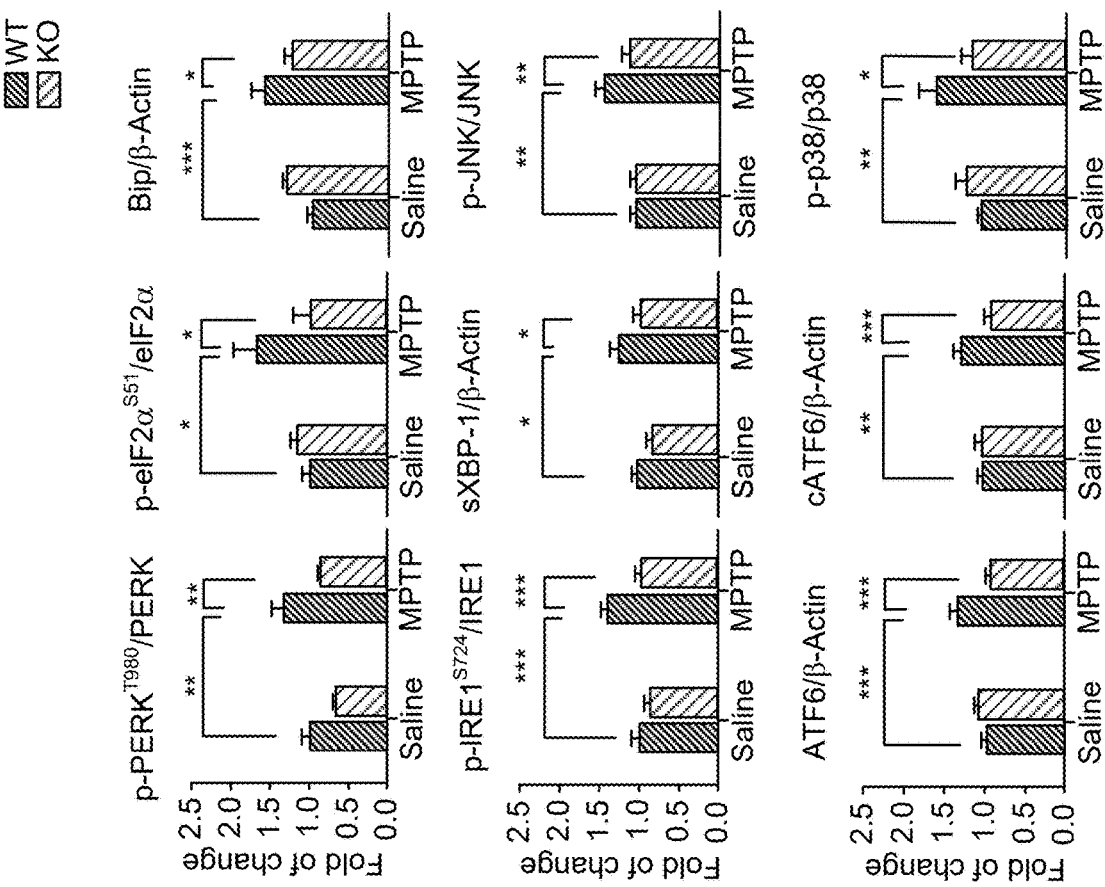
Figure 4B:
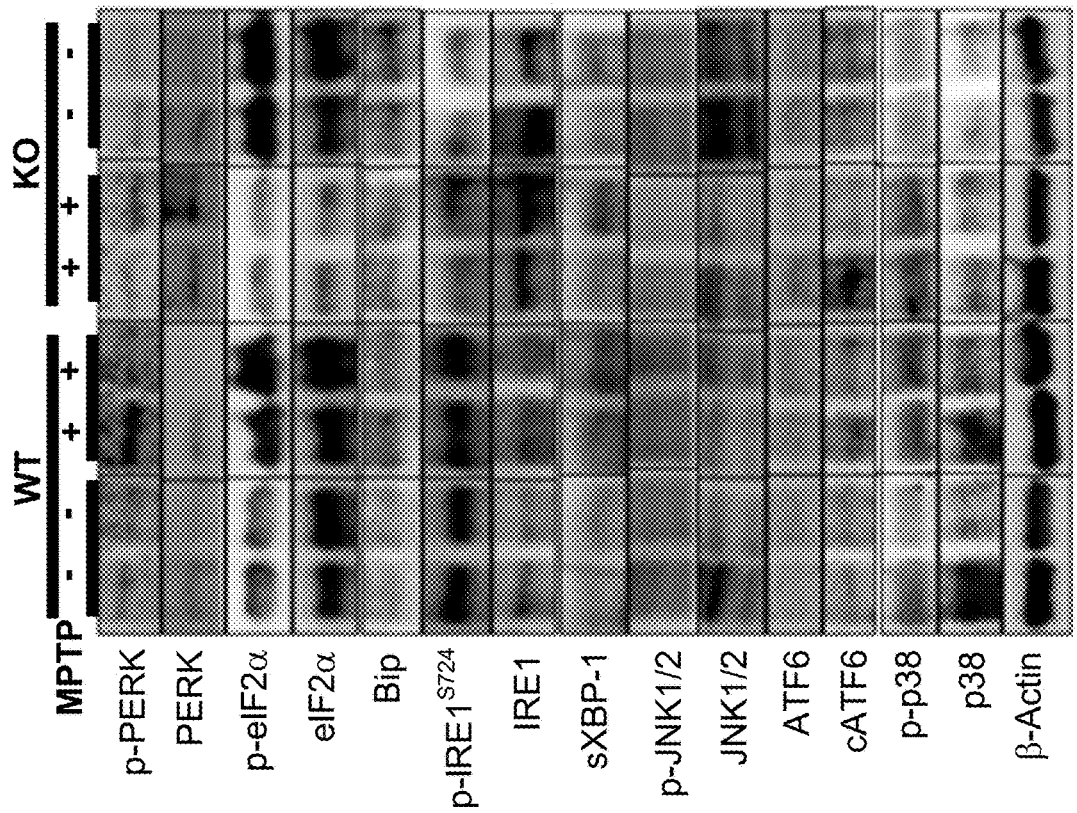

Role of sEH in MPTP-induced ER stress and oxidative stress in the striatum. It is well known that ER stress plays a role in the pathogenesis of PD (35), and that the sEH inhibitor attenuates activation of the ER (36-39). In this study, we examined the effects of TPPU and sEH deletion in the MPTP-induced activation of ER stress in the striatum. We found increased levels of three key sensors in the ER stress signaling pathway, including PKR-like ER-resident kinase (PERK), inositol-requiring enzyme 1α (IRE1α), and activating transcription factor 6 (ATF6) (FIGS. 4A and 4B). Levels of the associated downstream targets were elevated, suggesting full-scale activation of the ER stress pathway (37). Accordingly, phosphorylation of eukaryotic initiation factor 2 subunit α (eIF2α), mediated by phospho-PERK, was also increased. Phosphorylation of IRE1α led to a significant rise in total protein levels of spliced X-box binding protein 1 (Xbp1), as well as levels of the ER chaperone binding immunoglobulin protein. Increased phosphorylation of p38 and c-jun NH2-terminal kinase (JNK) 1/2 was also observed. Pharmacological inhibition by TPPU or sEH deficiency protected against MPTP (10 mg/kg×3 at 2 h intervals, 9:00, 11:00, and 13:00, 7 days after injection)-induced ER stress in the mouse striatum (FIGS. 4A and 4B).

Figure 4C:
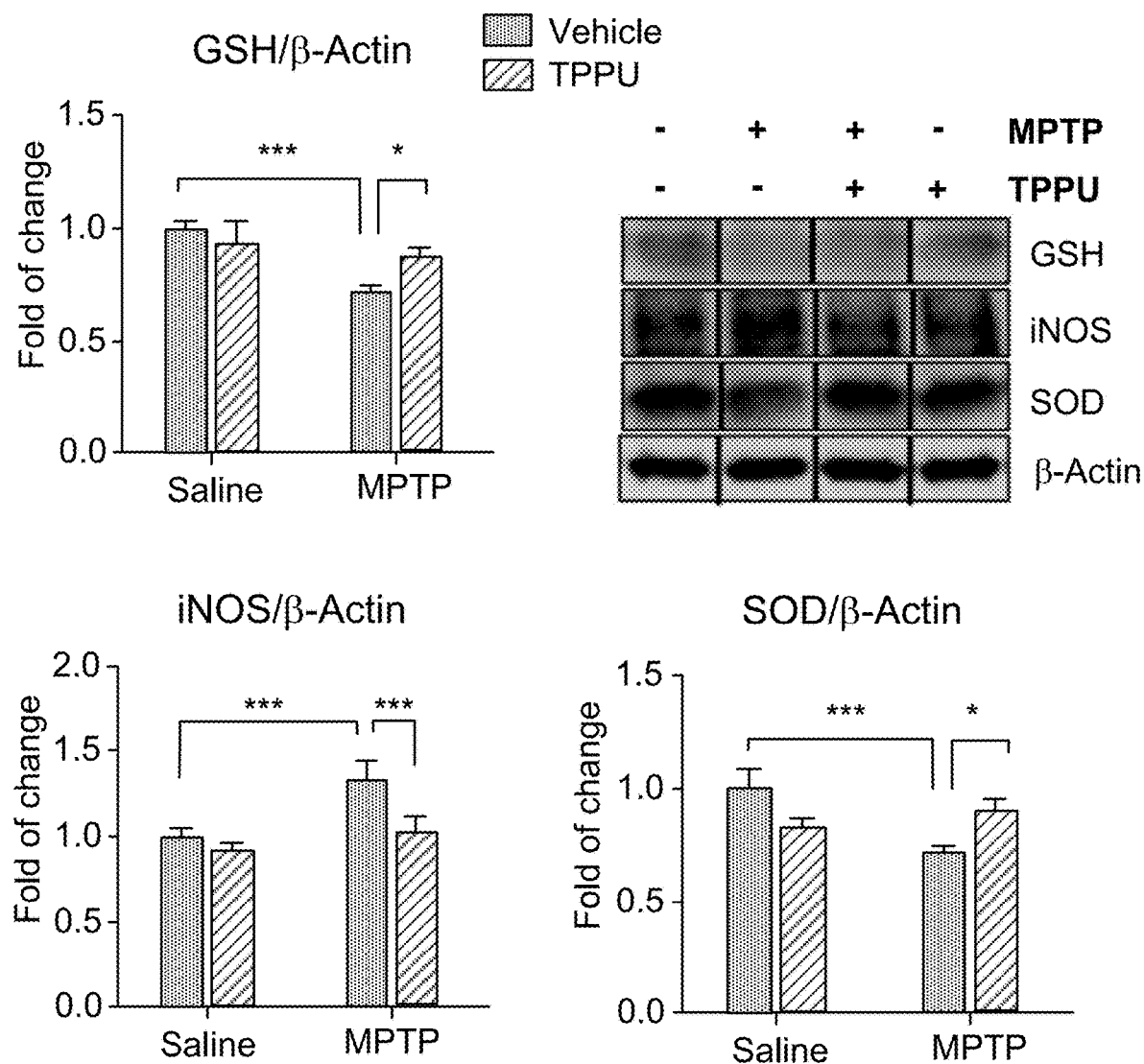
Figure 4D:
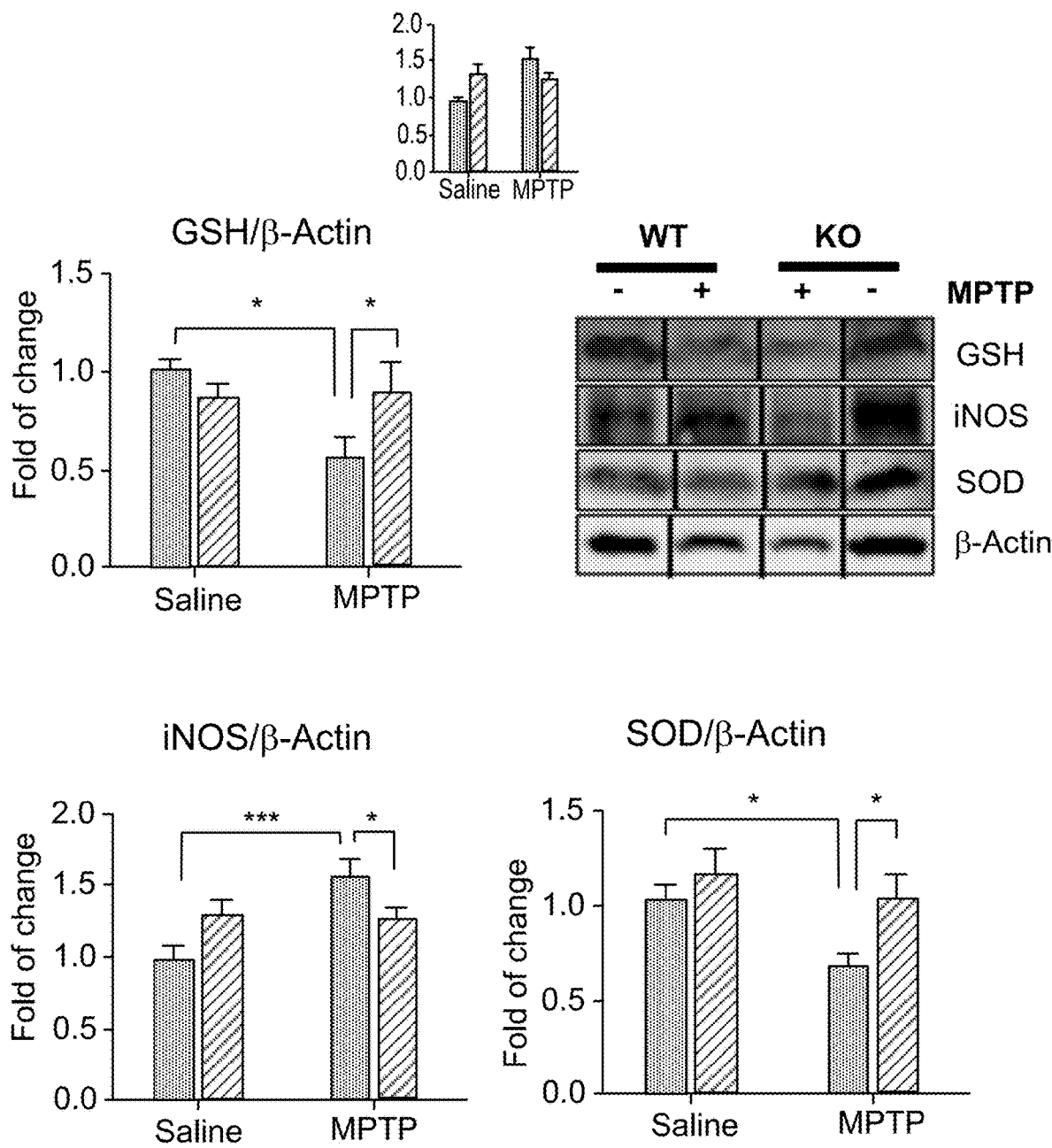

It is also known that oxidative stress plays a role in the pathogenesis of PD and in MPTP-induced neurotoxicity (13,14,40,41). MPTP (10 mg/kg×3 at 2 h intervals, 9:00, 11:00, and 13:00, 7 days after injection) caused alterations in the expression of glutathione (GSH), inducible nitric oxide (iNOS), and superoxide dismutase (SOD) in the striatum. Pharmacological inhibition by TPPU or sEH deficiency protected against MPTP-induced oxidative stress in the mouse striatum (FIGS. 4C and 4D). These results suggest that the inhibition of sEH protected against MPTP-induced ER stress and oxidative stress in the mouse brain.

Figure 5A:
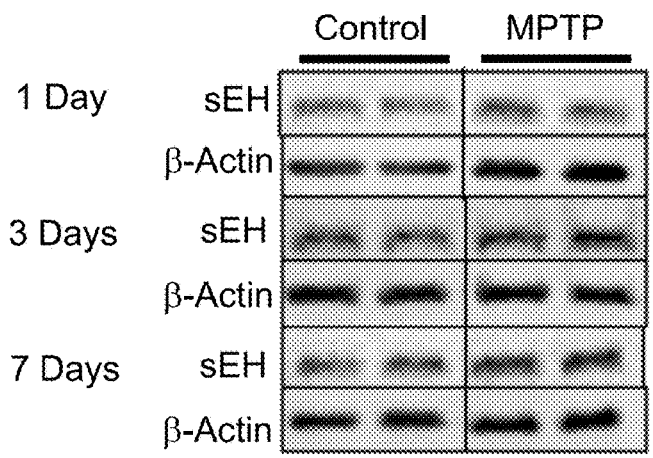
FIGS. 5A-G illustrate protein levels of sEH and oxylipin analysis in the striatum from MPTP-treated mice, and protein levels of sEH, DAT, TH in the postmortem brain samples. (A): Protein expression of sEH, α-synuclein, and phosphorylated α-synuclein (p-α-synuclein) in the striatum from MPTP (10 mg/kg×3, 2 h-interval, 9:00, 11:00, and 13:00. 1, 3 or 7 days after injection)-treated mice were measured by Western blotting. (B): Levels of sEH and p-α-synuclein/α-synuclein ratio in the striatum from MPTP-treated were significantly higher than those of control mice. The values are the mean±S.E.M. (n=6 or 7). *P<0.05, P<0.01 compared to control group (Student t-test). (C): There was a positive correlation (3 days: r=0.6310, P=0.0208, 7 days: r=6.225, P=0.0306) between sEH levels and p-α-synuclein/α-synuclein ratio in the mouse striatum. (D): MPTP (10 mg/kg×3, 2 h-interval, 9:00, 11:00, and 13:00) or vehicle was injected i.p. into mice. The mice were sacrificed 7 days after injection, and oxylipin analysis was performed. Tissue levels of 8(9)-EpETrE in the striatum from MPTP-treated mice were significantly lower than those on control mice. The values represent the mean±S.E.M. (n=8). *P<0.001 compared to control group (Student t-test). (E): Protein expression of sEH, DAT, TH, α-synuclein, and phosphorylated α-synuclein in the striatum from DLB patients (n=10) and controls (n=10) were measured by Western blotting. Representative immunoblots were shown from 2 subjects of the two groups. (F): Tissue levels of sEH in the striatum from DLB patients were significantly (Student t-test, P=0.0055) higher than those of controls. Ratio of phosphorylated α-synuclein/α-synuclein in the striatum from DLB patients was significantly (Student t-test, P=0.0008) higher than those of controls. Tissue levels of DAT and TH in the striatum from DLB patients was significantly (Student t-test, P=0.00198 for DAT, P<0.0001 for TH) lower than those of controls. The values represent the mean f S.E.M. (n=10). The values represent the mean±S.E.M. (n=10). (G): There was a positive correlation (r=0.4699, P=0.036) between sEH levels and the ratio of phosphorylated α-synuclein/α-synuclein in the subject (n=20). Furthermore, there was a negative correlation (r=−0.5429, P=0.00134) between sEH levels and TH levels in the subjects.
Figure 5B:
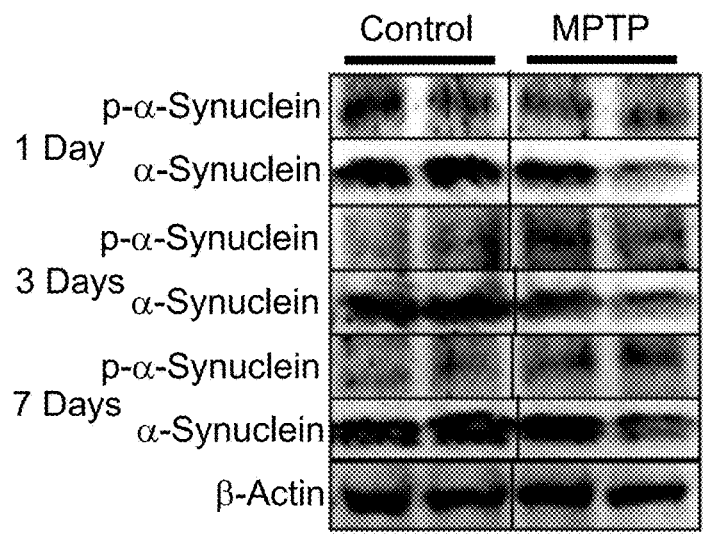
Figure 5B:
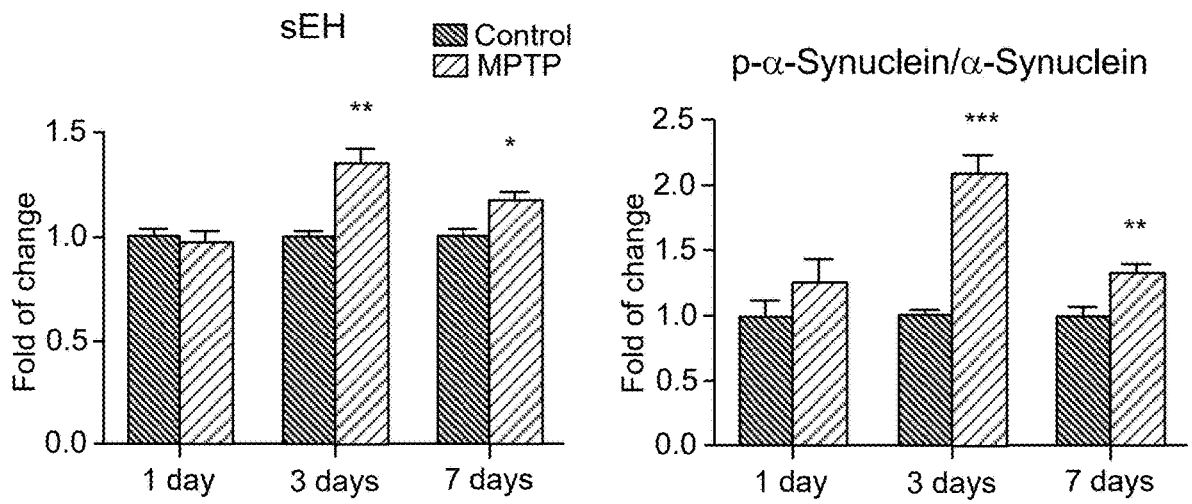
Figure 5C:
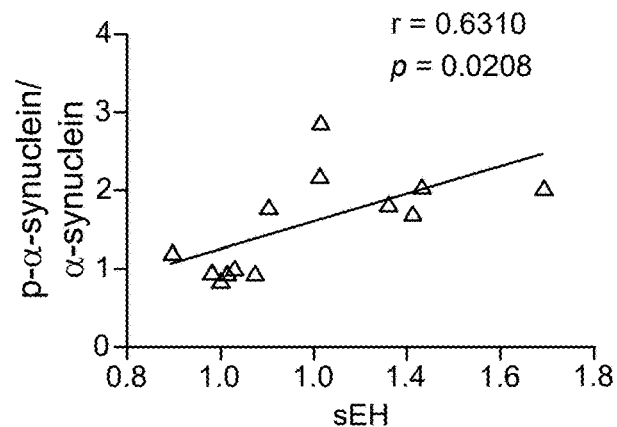

Protein expression and oxylipin profile in the striatum from MPTP-treated mice and DLB patients. Three or 7 days after the injections of MPTP (10 mg/kg×3 at 2 h intervals, 9:00, 11:00, and 13:00), we found a significant increase in the sEH protein in the striatum of MPTP-treated mice compared with control mice (FIGS. 5A and 5B). Furthermore, we found a significant increase in the phosphorylated α-synuclein/α-synuclein ratio in the striatum of MPTP-treated mice compared with control mice (FIGS. 5A and 5B). Interestingly, there was a positive correlation (3 days: r=0.6310, P=0.0208, 7 days: r=6.225, P=0.0306) between sEH levels and the phosphorylated α-synuclein/α-synuclein ratio in the mouse striatum (FIG. 5C). These results suggest that increased sEH plays a role in the phosphorylation of α-synuclein in the striatum of MPTP-treated mice.

Figure 5D:
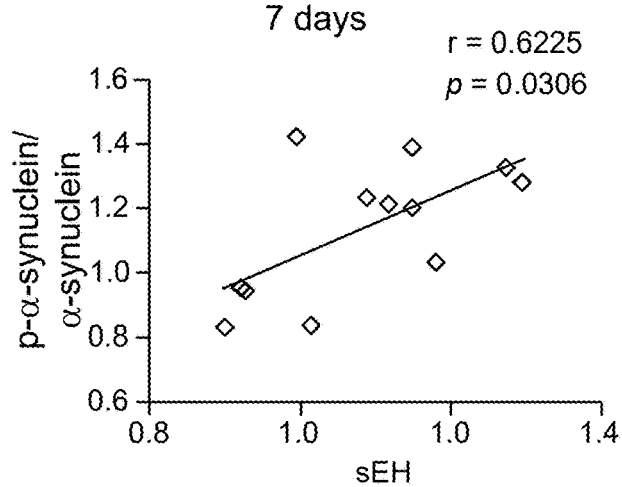
Figure 5D:
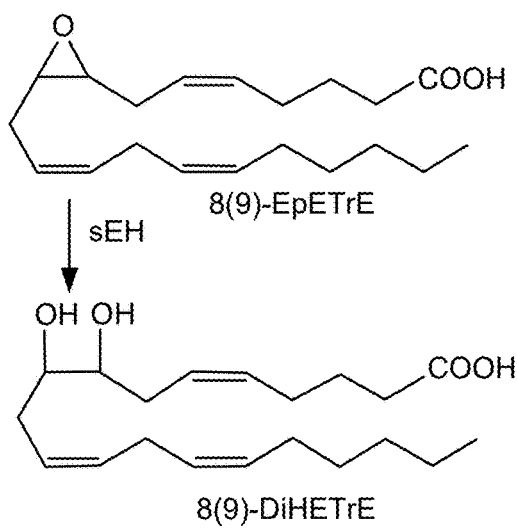
Figure 5D:
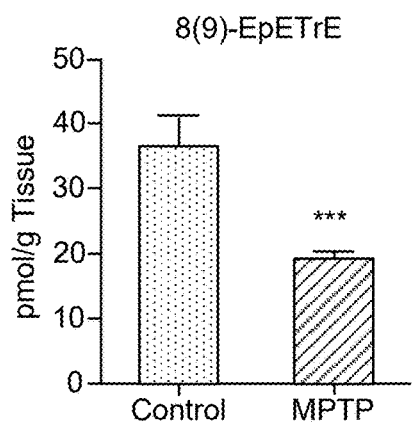
Figure 6:
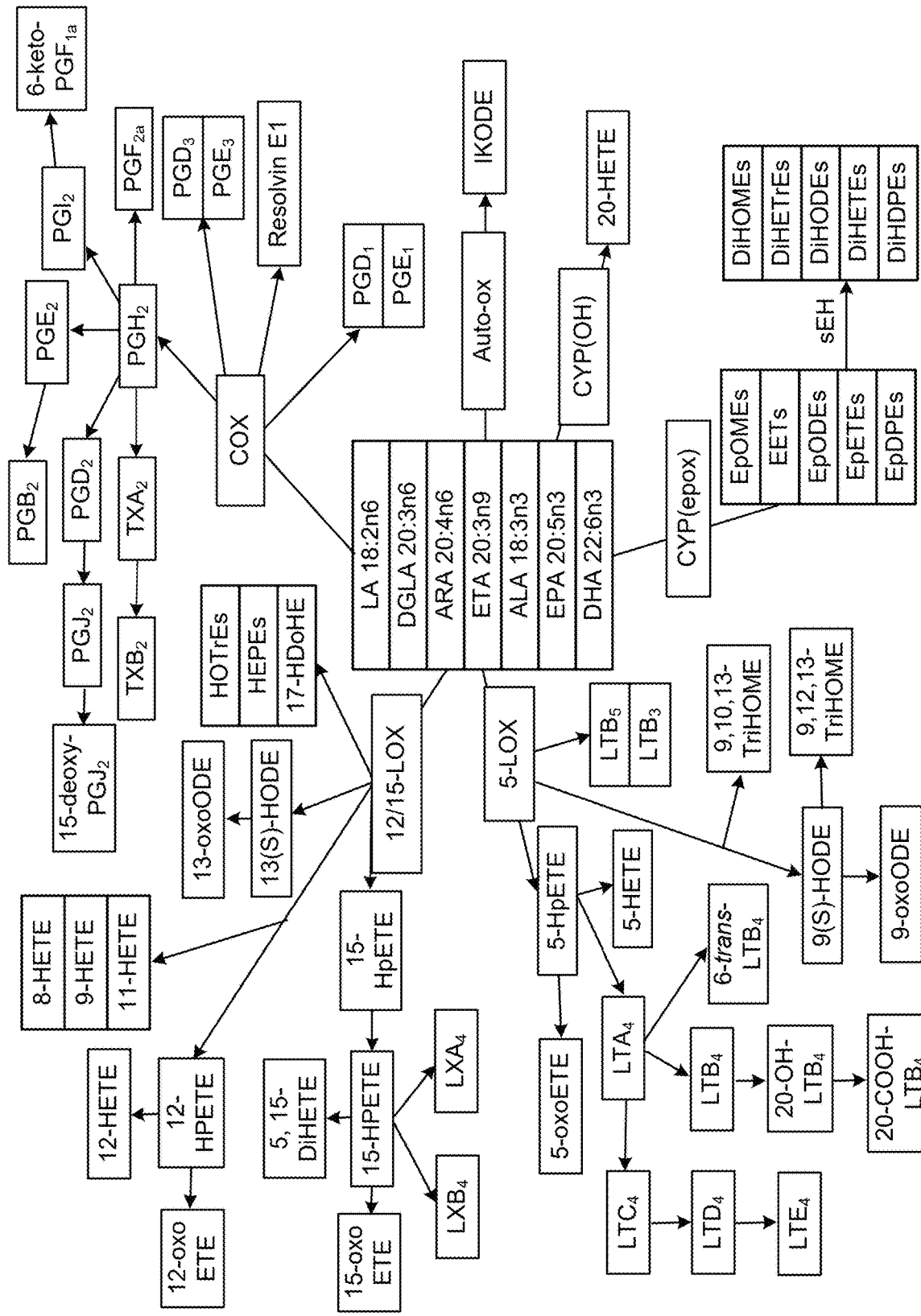
FIG. 6 illustrates eicosanoids measured in the striatum from control and MPTP-treated mice.

Next, we measured tissue levels of eicosanoids metabolites (FIG. 6 and Table 7) in the striatum of MPTP-treated mice and control mice. Tissue levels of 8(9)-EpETrE [8,9-epoxy-5Z,11 Z,14Z-eicosatrienoic acid], a metabolite of arachidonic acid, in the MPTP (10 mg/kg×3 at 2 h intervals, 9:00, 11:00, and 13:00, 7 days after injection)-treated mice were significantly lower than those of control mice, supporting the increased activity of sEH in the striatum from MPTP-treated mice (FIG. 5D and Table 7). Tissue levels of PGF2a (prostaglandin F2α) and 9(10)-DiHOME [(12Z)-9,10-dihydroxyoctadec-12-enoic acid] in MPTP-treated mice were also lower than those of control mice. In contrast, tissue levels of 10(11)-EpDPE [10(11)-epoxy-4Z,7Z,13Z,16Z,19Z-docosapentaenoic acid] in MPTP-treated mice were significantly higher than those of control mice (Table 7).

TABLE 7

Levels of eicosanoids metabolites in the striatum.

| | Control | MPTP | P value |
|---|---|---|---|
| 6-keto-PGF1a | 19.967 ± 1.629 | 20.015 ± 1.352 | 0.653 |
| TXB2 | 103.088 ± 8.432 | 98.406 ± 4.740 | 0.866 |
| 9,12,13-TriHOME | 69.431 ± 18.606 | 59.487 ± 4.168 | 0.582 |
| 9,10,13-TriHOME | 40.382 ± 10.250 | 33.635 ± 2.452 | 0.495 |
| PGF2a | 207.788 ± 9.015 | 160.704 ± 7.212 | 0.021 |
| PGE2 | 15.900 ± 0.477 | 13.830 ± 1.069 | 0.190 |
| PGD2 | 149.644 ± 8.398 | 127.452 ± 4.968 | 0.071 |
| 15,16-DiHODE | 4.004 ± 0.542 | 3.667 ± 0.609 | 0.498 |
| 12,13-DIHOME | 7.095 ± 0.390 | 8.348 ± 1.710 | 0.714 |
| 9,10-DiHOME | 3.226 ± 0.601 | 1.346 ± 0.158 | 0.004 |
| 19,20-DiHDPE | 4.092 ± 0.792 | 5.310 ± 0.523 | 0.392 |
| EKODE | 19.927 ± 6.196 | 23.007 ± 4.170 | 0.700 |
| 13-HODE | 47.613 ± 11.285 | 58.399 ± 5.240 | 0.326 |
| 9-HODE | 40.195 ± 6.041 | 41.360 ± 3.045 | 0.710 |
| 15-HETE | 124.063 ± 11.440 | 129.113 ± 6.703 | 0.484 |
| 11-HETE | 123.175 ± 9.516 | 114.056 ± 5.188 | 0.587 |
| 9-oxo-ODE | 33.256 ± 5.598 | 46.977 ± 5.160 | 0.072 |
| 12-HETE | 102.788 ± 8.210 | 136.621 ± 26.845 | 0.171 |
| 12(13)-EpOME | 7.595 ± 1.590 | 7.073 ± 0.689 | 0.745 |
| 14(15)-EpETrE | 89.347 ± 7.351 | 77.976 ± 11.479 | 0.512 |
| 9(10)-EpOME | 6.158 ± 0.899 | 6.641 ± 0.431 | 0.607 |
| 10(11)-EpDPE | 5.301 ± 1.525 | 9.530 ± 0.829 | 0.015 |
| 11(12)-EpETrE | 71.998 ± 6.178 | 61.583 ± 4.605 | 0.235 |
| 8(9)-EpETrE | 36.708 ± 4.502 | 19.048 ± 1.310 | 0.001 |
| 5(6)-EpETrE | 516.259 ± 30.771 | 544.908 ± 19.111 | 0.447 |

The values are the mean +/− SEM (n = 6).
Student t-test was used.
The bold was statistical significant.

Figure 5E:
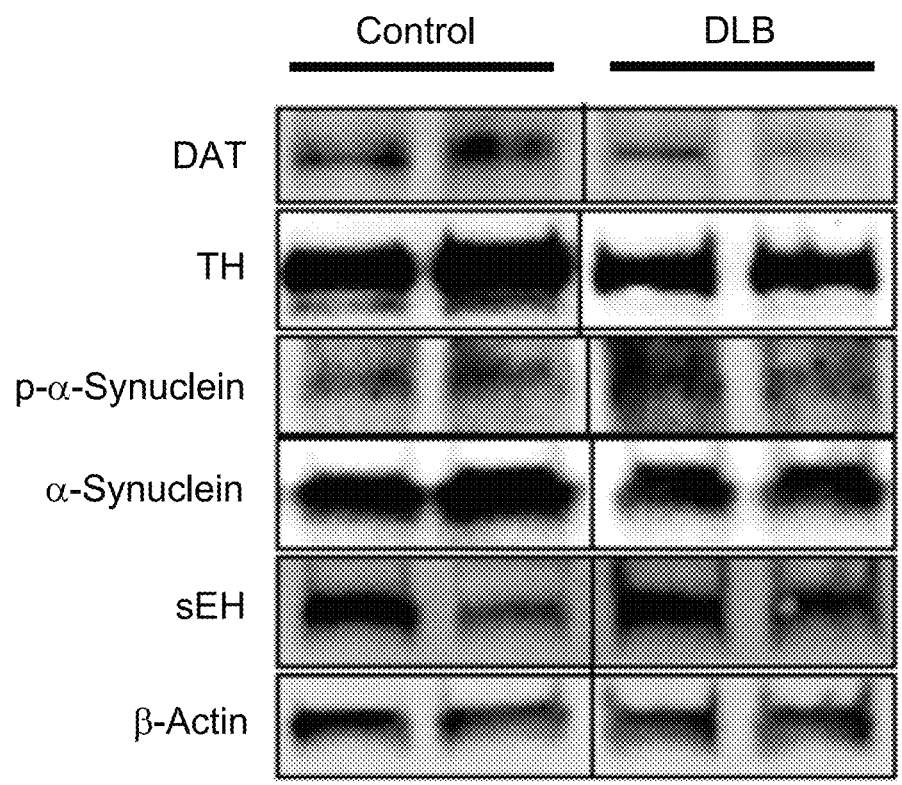
Figure 5F:
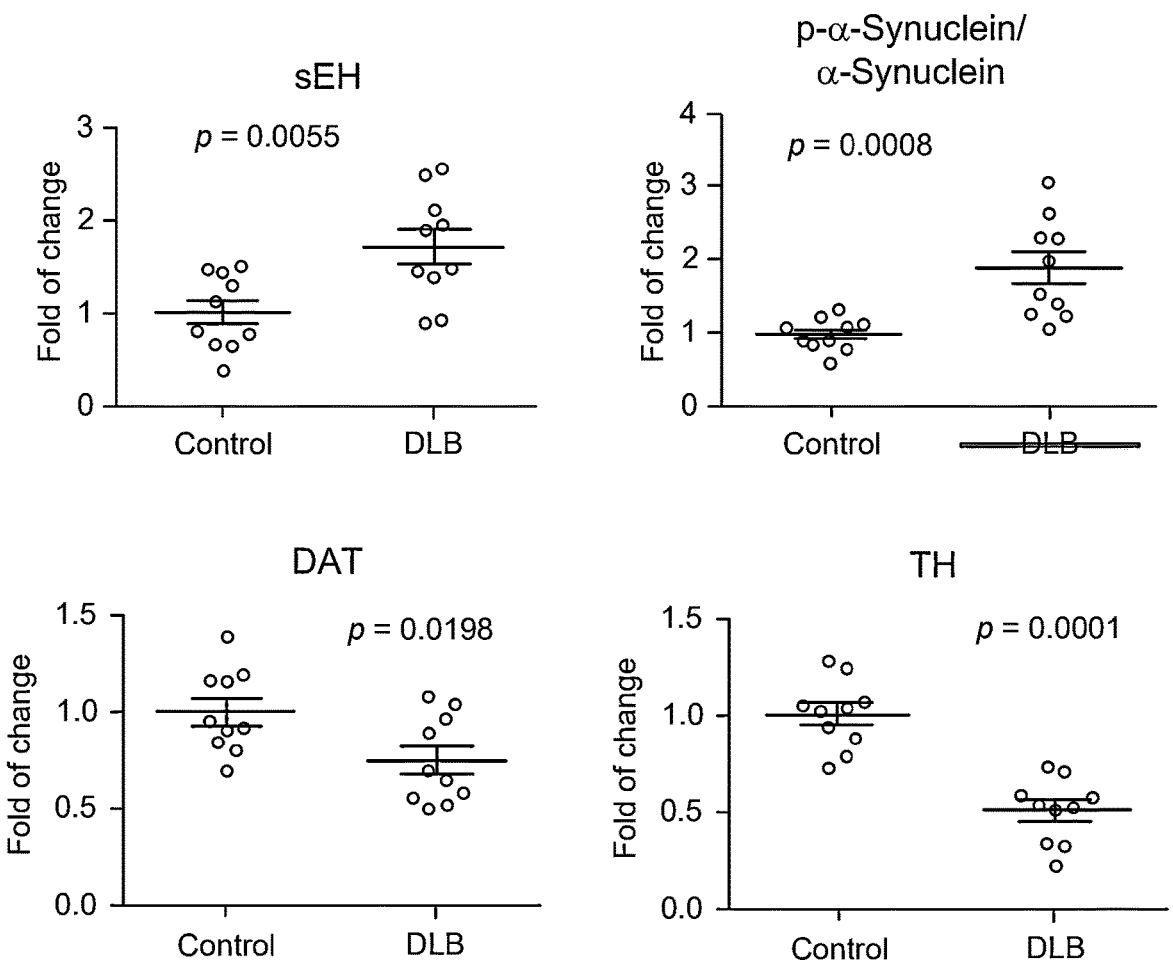
Figure 5G:
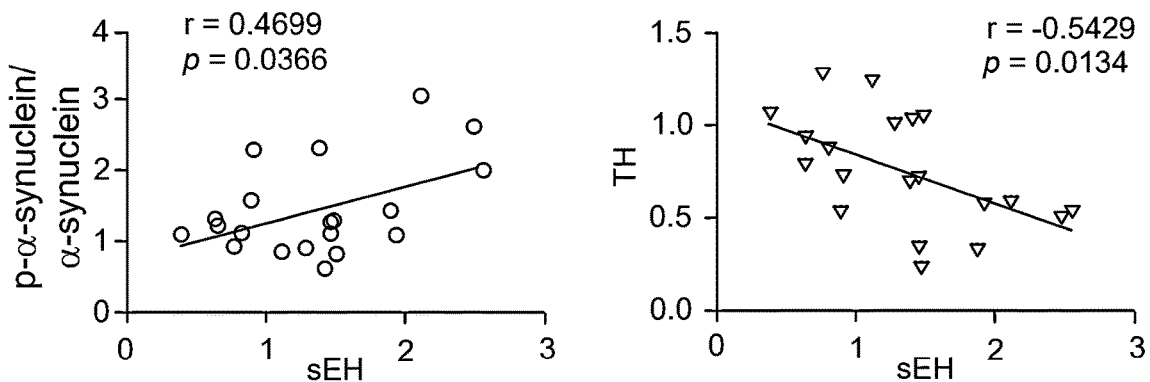

Increased expression of sEH in the striatum from DLB patients. Since deposition of α-synuclein has been shown in multiple brain regions of PD patients (3-6), postmortem brain samples from patients with DLB were used. We measured the protein expression of sEH, DAT, and TH in the striatum from these patients (n=10) and age-matched control subjects (n=10). Protein levels of sEH in the striatum from DLB patients were significantly higher than those of the controls, whereas protein levels of DAT and TH in the striatum from DLB patients were significantly lower than those of controls (FIG. 5E, 5F). Furthermore, the ratio of phosphorylated α-synuclein to α-synuclein in the striatum from DLB patients was significantly higher than that of controls (FIG. 5E, 5F). Interestingly, there was a positive correlation (r=0.470, P=0.036) between sEH levels and the ratio of phosphorylated α-synuclein to α-synuclein in all subjects (n=20) (FIG. 5G). Furthermore, there was a negative correlation (r=−0.543, P=0.0013) between sEH levels and TH levels in all subjects (n=20) (FIG. 5G). Collectively, it is likely that increased sEH plays a role in the pathogenesis of PD, as well as MPTP-induced neurotoxicity.

Figure 7A:
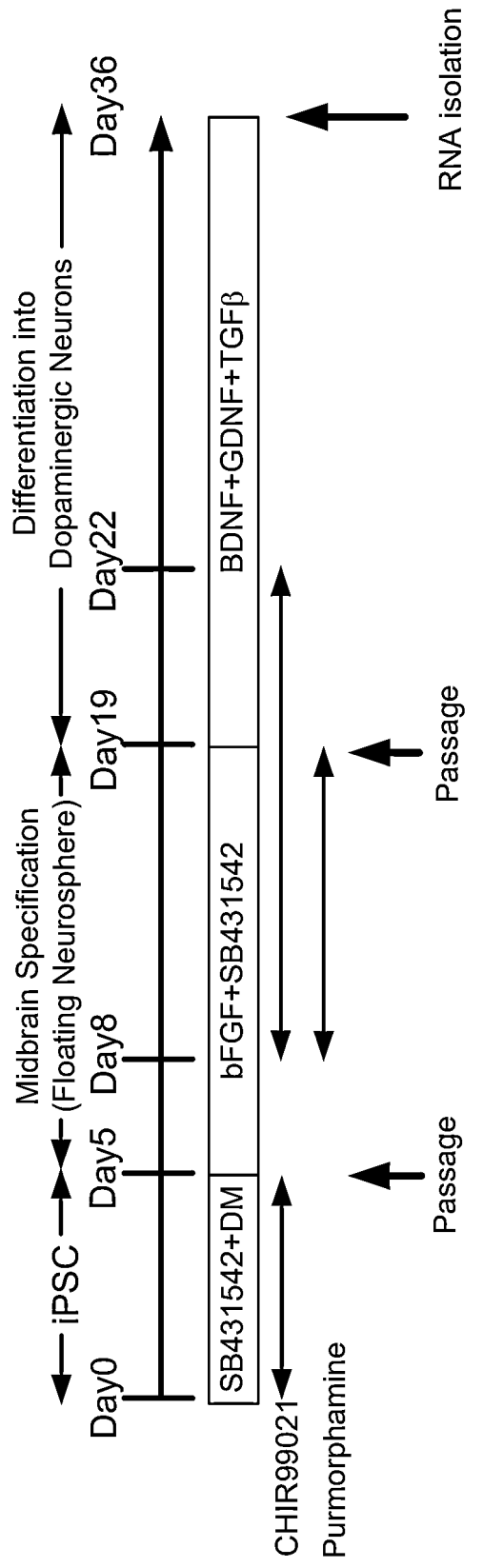
FIGS. 7A-F illustrate the role of sEH in the apoptosis of PARK2 iPSC-derived neurons. (A): Schedule of the culture protocol used for the induction of midbrain dopaminergic (mDA) neurons from hiPSCs. (B): qPCR analysis of sEH gene expression in control and PARK2 iPSC-induced mDA neurons (n=2 or 3, mean±S.E.M.). **P<0.01 compared to control group (Student t-test). (C): Schedule of the culture protocol used for the induction of mDA neurons from hiPSCs and TPPU treatment. (D): Representative images of TPPU-treated PARK2 and control DA-neurons visualized by IN Cell Analyzer 2200. Immunostaining was performed using cleaved caspase-3 and TH antibodies. Scale bar: 50 μM. (E): The numbers of TH-positive mDA neurons in the differentiated cells were calculated. The numbers of TH positive cells were not affected by TPPU treatment in both control and PARK2 iPSC-derived neurons. Two-way ANOVA revealed no statistical significant results (PARK2: $F_{1,12}$=0.3090, P=0.5885, TPPU: $F_{1,12}$=1.866, P=0.197; interaction: $F_{1,12}$ 0.0032, P=0.956). Data are shown as mean±S.E.M. (n=4). (F): Apoptosis in mDA neurons was quantified and evaluated by cleaved caspase-3 staining and IN Cell Analyzer 2200. Apoptotic cells were significantly increased in PARK2 iPSC-derived neurons compared to control cells. Treatment with TPPU significantly decreased apoptotic cells in PARK2 iPSC-derived neurons. Two-way ANOVA revealed the results (PARK2: $F_{1,12}$=9.999, P=0.0082, TPPU: $F_{1,12}$=5.356, P=0.0392; interaction: $F_{1,12}$=2.467, P=0.142). Data are shown as mean±S.E.M. (n=4). *P<0.05, **P<0.01 compared to DMSO treated PARK2 group.
Figure 7C:
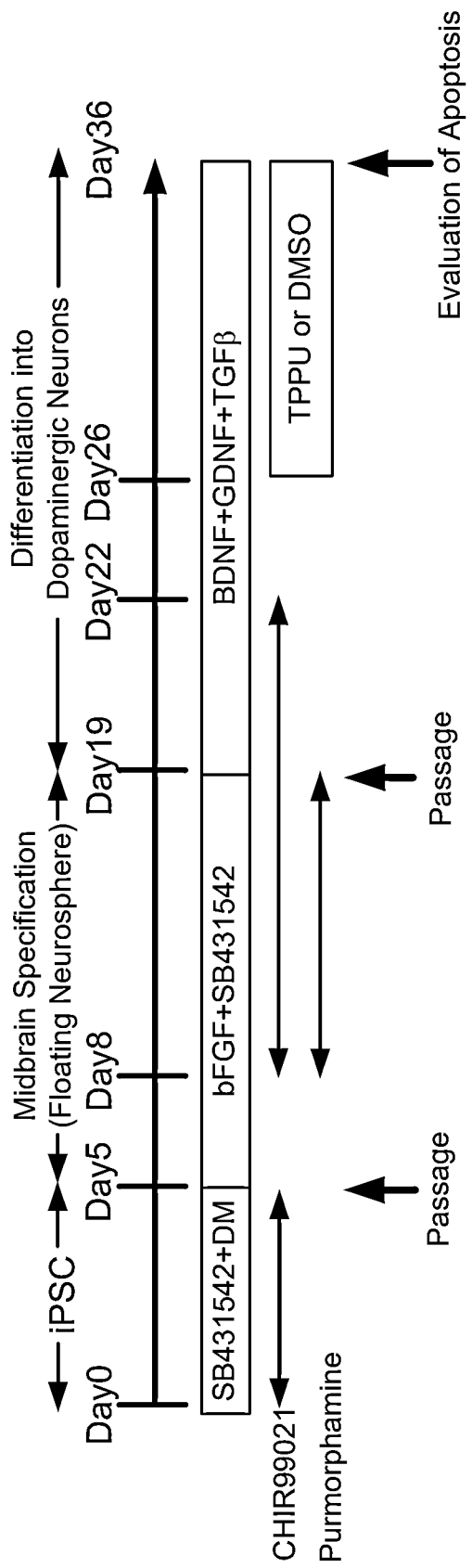
Figure 7B:
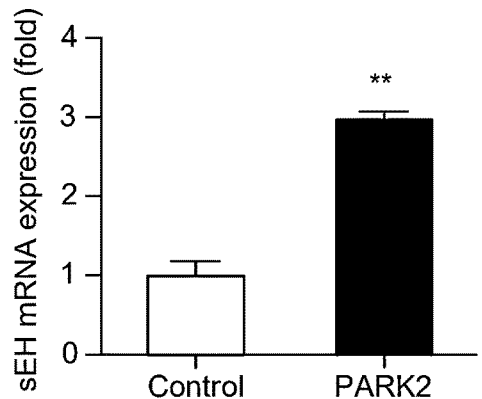

TPPU prevents apoptosis in PARK2-iPS-derived dopaminergic neurons. To assess the role of sEH in the pathogenesis of PD, we attempted to suppress sEH in dopaminergic neurons using TPPU. The iPSCs derived from PARK2, one of the familial form of PDs caused by a mutation in the PARKIN gene, were differentiated into midbrain dopaminergic neurons (FIG. 7A). We confirmed that the expression of sEH mRNA in the PARK2 iPSC-derived neurons was significantly higher than that from control iPSCs (FIG. 7B).

Figure 7E:
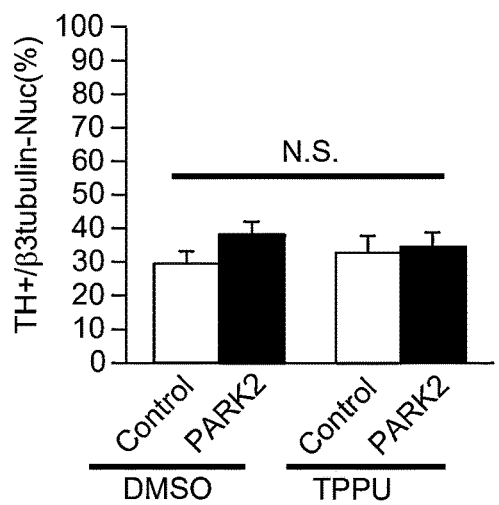
Figure 7F:
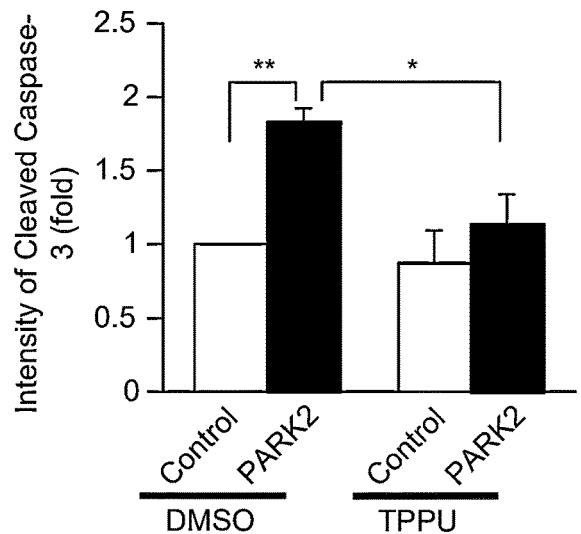
Figure 7D:
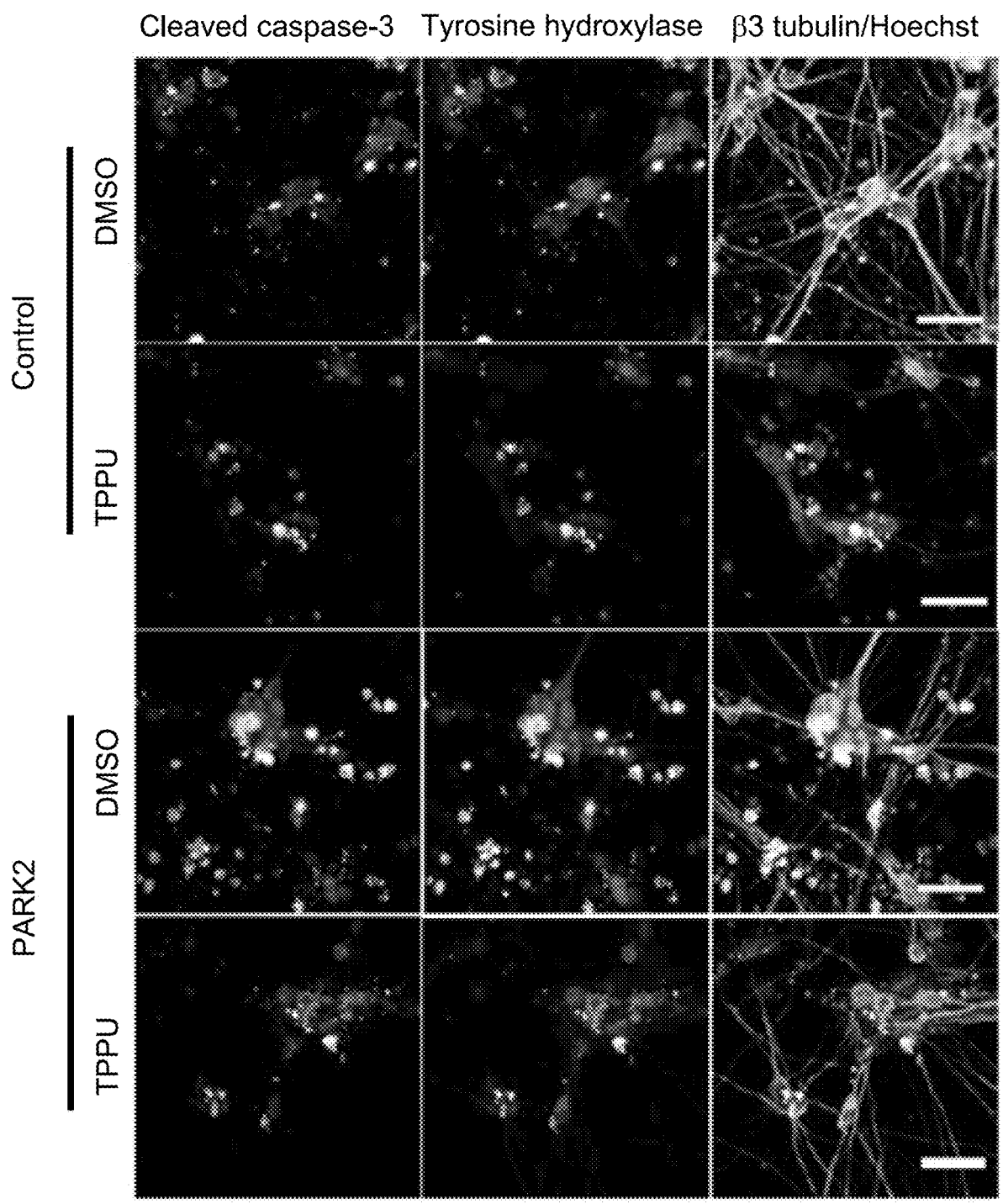

Next, we examined whether TPPU treatment could prevent progressive apoptosis in PARK2 iPSC-derived neurons. Dopaminergic neurons were differentiated, and evaluated by cleaved caspase-3 expression (FIG. 7C). At first, we confirmed that the numbers of TH-positive DA neurons in the differentiated cells were not changed by the presence of the PARK2 mutation or TPPU-treatment (FIG. 7D, 7E). The amounts of cleaved caspase-3 were then evaluated in TH-positive dopaminergic neurons using immunocytochemistry and an IN-Cell analyzer 2200 (FIG. 7D, 7F). While PARK2 iPSC-derived TH-positive neurons expressed significantly increased amounts of cleaved caspase-3, TPPU-treatment decreased cleaved caspase-3 expression in PARK2 neurons to similar levels as control neurons (FIG. 7F). These results suggest that the suppression of sEH by TPPU protected against apoptosis in PARK2 neurons, and that increased sEH is involved in the degeneration of DA neurons in PD patients.

DISCUSSION

The present results demonstrate a role of sEH in the pathogenesis of PD. The major findings of the present study are: First, MPTP-induced dopaminergic neurotoxicity in the striatum and SN was significantly attenuated by subsequent repeated administration of the potent sEH inhibitor, TPPU. Furthermore, MPTP-induced dopaminergic neurotoxicity in the striatum and SN was not detected in sEH KO mice. Second, MPTP-induced ER stress and oxidative stress in the striatum were significantly attenuated by subsequent repeated administration of TPPU or deletion of the sEH gene. Third, protein levels of sEH in the striatum from MPTP-treated mice or postmortem brain (striatum) from DLB patients were higher than those of controls. Interestingly, there was a positive correlation between sEH expression and the ratio of phosphorylated α-synuclein to α-synuclein in the striatum, suggesting a relationship between increased sEH expression and phosphorylation of α-synuclein in the striatum. Levels of 8(9)-EpETrE in the striatum from MPTP-treated mice were significantly lower than those of control mice, supporting the increased activity of sEH in the striatum from MPTP-treated mice. Finally, we found an increase level of sEH mRNA in PARK2 iPSC-derived dopaminergic neurons. Interestingly, treatment with TPPU significantly attenuated apoptosis in PARK2 iPSC-derived dopaminergic neurons. Collectively, these novel findings suggest that sEH plays a role in the pathogenesis of PD, and that sEH inhibitors find use as prophylactic or therapeutic drugs for PD.

In this study, we found that MPTP-induced neurotoxicity (e.g., loss of DAT, TH-positive cells, ER stress, and oxidative stress) in the mouse striatum and SN was attenuated after subsequent repeated oral administration of TPPU. In contrast, it has been reported that MPTP-induced loss of TH-positive cells in the mouse SN is attenuated by pretreatment with another sEH inhibitor, AUDA, although posttreatment with AUDA did not attenuate MPTP-induced neurotoxicity (42). Furthermore, sEH KO mice were resistant to MPTP-induced neurotoxicity in the striatum, consistent with previous reports (42,43). Thus, the results using the genetic deletion of sEH or the pharmacological inhibition of sEH suggest a crucial role of sEH in MPTP-induced neurotoxicity in the mouse striatum and SN.

Tissue levels of the sEH protein in the striatum of MPTP-treated mice were higher than those of control mice, which is consistent with a previous report (42). We also found that the phosphorylated α-synuclein/α-synuclein ratio in the striatum from MPTP-treated mice was higher than that of control mice. Interestingly, we found a positive correlation between the sEH protein and the phosphorylated α-synuclein/α-synuclein ratio in the striatum. Furthermore, we found that levels of sEH in the striatum from DLB patients were higher than those of controls. A positive correlation between sEH levels and the ratio of phosphorylated α-synuclein/α-synucleinin the striatum with DLB patients is noteworthy since α-synuclein is strongly linked to the pathogenesis of both familial and sporadic PD (3,4). There was a negative correlation between sEH levels and TH levels in all subjects, suggesting a crucial role of sEH in the dopaminergic neurotoxicity of PD. Collectively, it is likely that increased sEH in the striatum plays a role in the increased phosphorylation of α-synuclein in the striatum from MPTP-treated mice and DLB patients. Given the role of the increased phosphorylation of α-synuclein in the pathogenesis of PD and other α-synuclein-related neurodegenerative disorders, the data are consistent with the conclusion that pharmacological inhibition of sEH attenuates the phosphorylation of α-synuclein, as well as dopaminergic neurotoxicity in the brain, resulting in a delay in the disease progression of α-synuclein-related neurodegenerative disorders including PD and DLB.

Among many epoxyeicosatrienoic acids (EETs), tissue levels of 8(9)-EpETrE were significantly lower in MPTP-treated mice than those of control mice, supporting an increased activity of sEH in the striatum from MPTP-treated mice. 8(9)-EpETrE is metabolized to its corresponding diol, dihydroxyeicosatrienoic acid (DiHETrE), by sEH. It is known that EETs such as EpETrE are important components of many intracellular signaling pathways in both cardiac and extracardiac tissues (44), and that EETs possess potent anti-inflammatory properties (45,46). Interestingly, Collino et al. (47) reported increased serum concentrations of 8(9)-EpETrE in centenarians compared with elderly and young subjects, suggesting increased activity of CYP enzymes or decreased activity of sEH in the centenarians. These findings support the promotion of cellular detoxification mechanisms through specific modulation of the arachidonic acid metabolic cascade in centenarians (47). Although the precise mechanisms underlying the relationship between 8(9)-EpETrE and sEH in the striatum from MPTP-treated mice are currently unclear, the data are consistent with the conclusion that decreased levels of 8(9)-EpETrE by increased levels of sEH in the striatum are involved in MPTP-induced neurotoxicity.

Using patient-specific iPSCs, we found an increased expression of sEH in PARK2 iPSC-derived neurons compared to controls, and TPPU protected against apoptosis in PARK2 iPSC-derived neurons, suggesting that increased activity of sEH plays a role in the pathogenesis of the PD patient with PARK2 mutations. From the present study, we do not fully account for the molecular mechanisms of other familial or sporadic PD since PARKIN is a causative gene of autosomal recessive juvenile PD (48,49). Therefore, further studies using human iPSCs from other familial or sporadic PD patients are needed.

It is well known that PD patients have depressive symptoms (28-30). Previously, we reported the prophylactic and therapeutic effects of TPPU in the inflammation and chronic social defeat stress models of depression (26), demonstrating that sEH inhibitors prevent the onset of the depression-like phenotype by inflammation or repeated stress. Given the comorbidity of depressive symptoms in PD patients, sEH inhibitors serve as prophylactic drugs to prevent the progression of PD in patients.

In conclusion, this study shows that genetic deletion or pharmacological inhibition of sEH protects against MPTP-induced neurotoxicity in the mouse brain. Furthermore, the data using postmortem brain are consistent with the conclusion that sEH plays a role in the aggregation of α-synuclein and phosphorylated α-synuclein in the striatum, supporting a crucial role of sEH in the pathogenesis of PD and DLB. Moreover, the sEH inhibitor used in this study protected against apoptosis in PARK2 iPSC-derived neurons. Therefore, sEH inhibitors appear to be new prophylactic or therapeutic drugs for α-synuclein-related neurodegenerative disorders such as PD and DLB.

REFERENCES

1. Kalia L V, Lang A E (2015) Parkinson's disease. Lancet 386:896-912.
2. Ascherio P A, Schwarzschild M A (2016) The epidemiology of Parkinson's disease: risk factors and prevention. Lancet Neurol 15:1257-1272.
3. Spillantini M G, Schmidt M L, Lee V MY, Trojanowsky J Q, Jakes R, Goedert M (1997) α-synuclein in Lewy bodies. Nature 388:839-840.
4. Spillantini M G, Crowther R A, Jakes R, Hasegawa M, Goedert M (1998) α-Synuclein in filamentous inclusions of Lewy bodies from Parkinson's disease and dementia with Lewy bodies. Proc Natl Acad Sci USA 95:6469-6473.
5. Olanow C W, Kordower J H (2017) Targeting α-synuclein as a therapy for Parkinson's disease: the battle begins. Mov Disord 32:203-207.
6. Dickson D W (2018) Neuropathology of Parkinson disease. Parkinsonism Relat Disord 46 (Suppl. 1):S30-S33.
7. Dehay B, et al (2015) Targeting α-synuclein for treatment of Parkinson's disease: mechanistic and therapeutic considerations. Lancet Neurol 14:855-866.
8. Kieburtz K, Katz R, Olanow C W (2017) New drugs for Parkinson's disease: The regulatory and clinical development pathways in the United States. Mov Disord 2017 Dec. 4. doi: 10.1002/mds.27220.
9. McGeer P L, McGeer E G (2004) Inflammation and neurodegeneration in Parkinson's disease. Parkinsonism Relat Disord 10 (Suppl. 1):S3-S7.
10. Hirsch E C, Hunot S (2009) Neuroinflammation in Parkinson's disease: a target for neuroprotection?Lancet Neurol 8:382-397.
11. Hirsch E C, Vyas S, Hunot S (2012) Neuroinflammation in Parkinson's disease. Parkinsonism Relat Disord 18 (Suppl. 1): S210-S212.
12. Joshi N, Singh S (2017) Updates on immunity and inflammation in Parkinson disease pathology. J Neurosci Res 2017 Oct. 26. doi: 10.1002/jnr.24185.
13. Beal M F (2003) Mitochondria, oxidative stress, and inflammation in Parkinson's disease. Ann N Y Acad Sci 991:120-131.
14. Jenner P (2003) Oxidative stress in Parkinson's disease. Ann Neurol 53: (Suppl. S3):S26-S38.
15. Abou-Sleiman P M, Muqit M M K, Wood N W (2006) Expanding insights of mitochondrial dysfunction in Parkinson's disease. Nat Rev Neurosci 7:207-1219.
16. Schapira A H V (2008) Mitochondrial in the aetiology and pathogenesis of Parkinson's disease. Lancet Neurol 7:97-109.
17. Toulorge D, Schapira A H V, Haji R (2016) Molecular changes in the postmortem parkinsonian brain. J Neurochem 139 (Suppl. 1):27-58.

18. Bousquet M, Calon F, Cicchetti F (2011) Impact of omega-3 fatty acids in Parkinson's disease. Aging Res Rev 10:453-463.
19. Lei E, Vacy K, Boon W C (2016) Fatty acids and their therapeutic potential in neurological disorders. Neurochem Int 95:75-84.
20. Morisseau C, Hammock B D (2005) Epoxide hydrolases: mechanisms, inhibitor designs, and biological roles. Annu Rev Pharmacol Toxicol 45:311-333.
21. Imig J D, Hammock B D (2009) Soluble epoxide hydrolase as a therapeutic target for cardiovascular diseases. Nat Rev Drug Discov 8:794-805.
22. Morisseau C, Hammock B D (2013) Impact of soluble epoxide hydrolase and epoxyeicosanoids on human health. Annu Rev Pharmacol Toxicol 53:37-58.
23. Harris T R, Hammock B D (2013) Soluble epoxides hydrolase: gene structure, expression and deletion. Gene 526(2):61-74.
24. Wagner K, Vito S, Inceoglu B, Hammock B D (2014) The role of long chain fatty acids and their epoxide metabolites in nociceptive signaling. Prostaglandins Other Lipid Mediat 113-115:2-12.
25. López-Vicario C, et al (2015) Inhibition of soluble epoxide hydrolase modulates inflammation and autophagy in obese adipose tissue and liver: role for omega-3 epoxides. Proc Natl Acad Sci USA 112:536-541.
26. Ren Q, et al (2016) Gene deficiency and pharmacological inhibition of soluble epoxide hydrolase confers resilience to repeated social defeat stress. Proc Natl Acad Sci USA 113:E1944-E1952.
27. Hashimoto K (2016) Soluble epoxide hydrolase: a new therapeutic target for depression. Expert Opin Ther Targets 20:1149-1151.
28. Cummings J L (1992) Depression and Parkinson's disease: a review. Am J Psychiatry 149:443-454.
29. Goodarzi Z, et al (2016) Detecting depression in Parkinson disease: A systematic review and meta-analysis. Neurology 87:426-437.
30. Schapira A H V, Chaudhuri K R, Jenner P (2017) Non-motor features of Parkinson disease. Nat Rev Neurosci 18:435-450.
31. Lakkappa N, Krishnamurthy P T, Hammock B D, Velmurugan D, Bharath M M S (2016) Possible role of epoxyeicosatrienoic acid in prevention of oxidative stress mediated neuroinflammation in Parkinson disorders. Med Hypothesis 93:161-165.
32. Rose et al (2010) 1-Aryl-3-(1-acylpiperidin-4-yl)urea inhibitors of human and murine soluble epoxide hydrolase: structure-activity relationships, pharmacokinetics, and reduction of inflammatory pain. J Med Chem 53(19): 7067-7075.
33. Ostermann Al, et al (2015) Oral treatment of rodents with soluble epoxide hydrolase inhibitor 1-trifluoromethoxyphenyl-3-(1-propionylpiperidin-4-yl)urea (TPPU): bioavailability, resulting drug levels and modulation of oxylipin pattern. Prostaglandins Other Lipid Mediat 121(Pt A):131-137.
34. Imaizumi Y, et al (2012) Mitochondrial dysfunction associated with increased oxidative stress and α-synuclein accumulation in PARK2 iPSC-derived neurons and postmortem brain tissue. Mol Brain 5:35.
35. Mercado G, Castillo V, Soto P, Sidhu A (2016) E R stress and Parkinson's disease: Pathological inputs that converge into the secretory pathway. Brain Res 1648(Pt B):626-632.
36. Bettaieb A, et al (2013) Soluble epoxide hydrolase deficiency or inhibition attenuates diet-induced endoplasmic reticulum stress in liver and adipose tissue. J Biol Chem 288:14189-14199.
37. Inceoglu B, et al (2015) Endoplasmic reticulum stress in the peripheral nervous system is a significant driver of neuropathic pain. Proc Natl Acad Sci USA 112:9082-9087.
38. Harris T R, et al (2015) Inhibition of soluble epoxide hydrolase attenuates hepatic fibrosis and endoplasmic reticulum stress induced by carbon tetrachloride in mice. Toxicol Appl Pharmacol 286:102-111.
39. Inceoglu B, Bettaieb A, Haj F G, Gomes A V, Hammock B D (2017) Modulation of mitochondrial dysfunction and endoplasmic reticulum stress are key mechanisms for the wide-ranging actions of epoxy fatty acids and soluble epoxide hydrolase inhibitors. Prostaglandins Other Lipid Mediat 133:68-78.
40. Dias V, Junn E, Mouradian M M (2013) The role of oxidative stress in Parkinson's disease. J Parkinsons Dis 3:461-469.
41. Paul R, Choudhury A, Kumar S, Giri A, Sandhir R, Borah A (2017) Cholesterol contributes to dopamine-neuronal loss in MPTP mouse model of Parkinson's disease: Involvement of mitochondrial dysfunctions and oxidative stress. PLoS One 12:e0171285.
42. Qin X, et al (2015) Soluble epoxide hydrolase deficiency or inhibition attenuates MPTP-induced parkinsonism. Mol Neurobiol 52:187-195.
43. Huang H J, Wang Y T, Lin H C, Lee Y H, Lin A M Y (in press) Soluble epoxide hydrolase inhibition attenuates MPTP-induced in the nigrostriatal dopaminergic system: involvement of α-synuclein aggregation and E R stress. Mol Neurobiol doi: 10.1007/s12035-017-0726-9.
44. Seubert J M, Zeldin D C, Nithipatikom K, Gross G J (2007) Role of epoxyeicosatrienoic acids in protecting the myocardium following ischemia/reperfusion injury. Prostaglandins Other Lipid Mediat 82:50-59.
45. Campbell W B (2000) New role for epoxyeicosatrienoic acids as anti-inflammatory mediators. Trends Pharmacol Sci 21:125-127.
46. Wagner K M, McReynolds C B, Schmidt W K, Hammock B D (2017) Soluble epoxide hydrolase as a therapeutic target for pain, inflammatory and neurodegenerative diseases. Pharmacol Ther 180:62-76.
47. Collino S, et al (2013) Metabolic signatures of extreme longevity in northern Italian centenarians reveal a complex remodeling of lipids, amino acids, and gut microbiota metabolism. PLoS One 8:e56564.
48. Kitada T, et al (1998) Mutations in the parkin gene cause autosomal recessive juvenile parkinsonism. Nature 392: 605-608.
49. Shimura H, et al (2000) Familial Parkinson disease gene product, parkin, is a ubiquitin-protein ligase. Nat Genet 25:302-305.
50. Sinai C J, et al (2000) Targeted disruption of soluble epoxide hydrolase reveals a role in blood pressure regulation. J Biol Chem 275:40504-40510.
51. Koike K, et al (2005) The immunophilin ligand FK506 protects against methamphetamine-induced dopaminergic neurotoxicity in mouse striatum. Neuropharmacology 48:391-397.
52. Zhang L, et al (2006) Protective effects of minocycline on behavioral changes and neurotoxicity in mice after administration of methamphetamine. Prog Neuropsychopharmacol Biol Psychiatry 30:1381-1393.

53. Ren Q, Zhang J C, Ma M, Fujita Y, Wu J, Hashimoto K (2014) 7,8-Dihydroxyflavone, a TrkB agonist, attenuates behavioral abnormalities and neurotoxicity in mice after administration of methamphetamine. Psychopharmacology (Berl) 231:159-166.
54. Paxinos G, Franklin K (2002) Paxinos and Franklin's the Mouse Brain in Stereotaxic Coordinates, 4th Edition. Academic Press.
55. Kobayashi K, et al (2016) Survival of corticostriatal neurons by Rho/Rho-kinase signaling pathway. Neurosci Lett 630:45-52.
56. Ren Q, et al (2015) BDNF-TrkB signaling in the nucleus accumbens shell of mice has key role in methamphetamine withdrawal symptoms. Transl Psychiatry 5:e666.
57. Saito Y, et al (2003) Accumulation of phosphorylated alpha-synuclein in aging human brain. J Neuropathol Exp Neurol 62:644-654.
58. Morimoto S, et al (2017) Homovanillic acid and 5-hydroxyindole acetic acid as biomarkers for dementia with Lewy bodies and coincident Alzheimer's disease: An autopsy-confirmed study. PLOS One 12:e0171524.
59. Yang J, Schmelzer K, Georgi K, Hammock B D (2009) Quantitative profiling method for oxylipin metabolome by liquid chromatography electrospray ionization tandem mass spectrometry. Anal Chem 81:8085-8093.
60. Takahashi K, et al (2007) Induction of pluripotent stem cells from adult human fibroblasts by defined factors. Cell 131:861-872.
61. Imaizumi K, et al (2015) Controlling the regional identity of hPSC-derived neurons to uncover neuronal subtype specificity of neurological disease phenotypes. Stem Cell Reports 5:1010-1022
62. Matsumoto T, (2016) Functional neurons generated from T cell-derived induced pluripotent stem cells for neurological disease modeling. Stem Cell Reports 6:422-435.
63. Fujimori K, Matsumoto T, Kisa F, Hattori N, Okano H, and Akamatsu W (2017) Escape from pluripotency via inhibition of TGF-β/BMP and activation of Wnt signaling accelerates differentiation and aging in hPSC progeny cells. Stem Cell Reports 9:1675-1691

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of mitigating Parkinson's disease in a subject, said method comprising:
 administering, to the subject an inhibitor of soluble epoxide hydrolase (sEHI) in an amount sufficient to mitigate Parkinson's disease, wherein the sEHI is a compound of Formula (II)

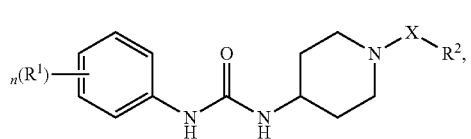

or a pharmaceutically acceptable salt thereof,
wherein X is C(O)
each $R^1$ is H, halogen, $C_{1-6}$ alkyl, $C_{1-6}$ alkoxy, $C_{1-6}$ haloalkyl, or $C_{1-6}$ haloalkoxy, wherein
at least 1 $R^1$ is other than H;
$R^2$ is $C_{1-6}$ alkyl or $C_{1-6}$ haloalkyl; and
subscript n is 1, 2, 3, 4, or 5.

2. A method of reducing the risk, lessening the severity, or delaying the progression or onset of Parkinson's disease in a subject, said method comprising: administering, or to the subject an inhibitor of soluble epoxide hydrolase (sEHI)in an amount sufficient to reduce the risk, lessen the severity, or delay the progression or onset of Parkinson's disease,, wherein the sEHI is a compound of Formula (II)

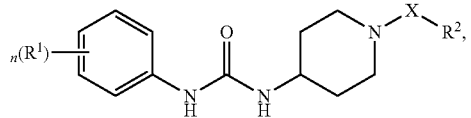

or a pharmaceutically acceptable salt thereof,
wherein X is C(O)
each $R^1$ is H, halogen, $C_{1-6}$ alkyl, $C_{1-6}$ alkoxy, $C_{1-6}$ haloalkyl, or $C_{1-6}$ haloalkoxy, wherein
at least 1 $R^1$ is other than H;
$R^2$ is $C_{1-6}$ alkyl or $C_{1-6}$ haloalkyl; and
subscript n is 1, 2, 3, 4, or 5.

3. The method of claim 1, wherein the mitigation comprises:
 (a) a reduction in the rate of alpha-synuclein aggregate or deposit formation in the brain of the subject;
 (b) a reduction in alpha-synuclein aggregate or deposit load in the brain of the subject;
 (c) an improvement in the cognitive and/or motor abilities of the subject;
 (d) a perceived improvement in quality of life by the human.

4. The method of claim 1, wherein the sEHI is a compound having the formula

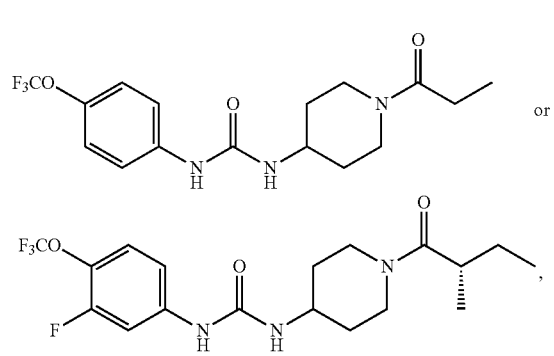

or a pharmaceutically acceptable salt thereof.

5. The method of claim 1, wherein the sEHI is a compound having the formula

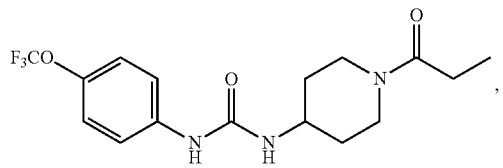 [SMILES: CCC(=O)N1CCC(NC(=O)Nc2ccc(OC(F)(F)F)cc2)CC1]

or a pharmaceutically acceptable salt thereof.

6. The method of claim 1, wherein the sEHI is a compound having the formula

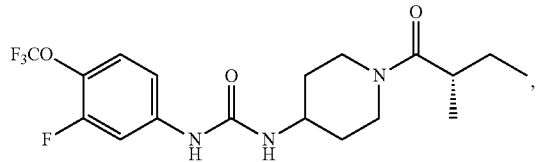 [SMILES: CC[C@H](C)C(=O)N1CCC(NC(=O)Nc2ccc(OC(F)(F)F)c(F)c2)CC1]

or a pharmaceutically acceptable salt thereof.

7. The method of claim 2, wherein the sEHI is a compound having the formula
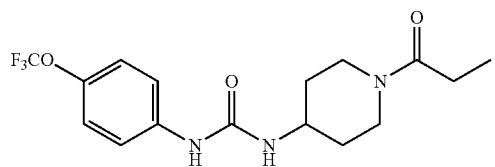
or
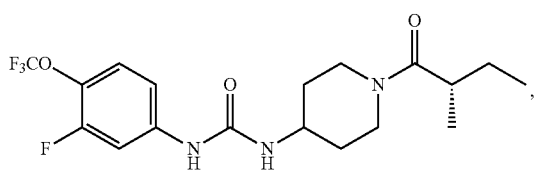
or a pharmaceutically acceptable salt thereof.
8. The method of claim 2, wherein the sEHI is a compound having the formula
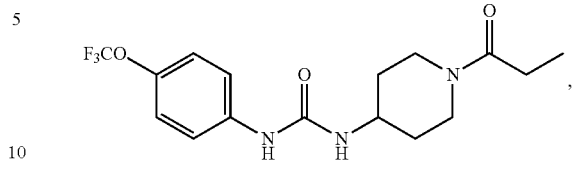
or a pharmaceutically acceptable salt thereof.
9. The method of claim 2, wherein the sEHI is a compound having the formula
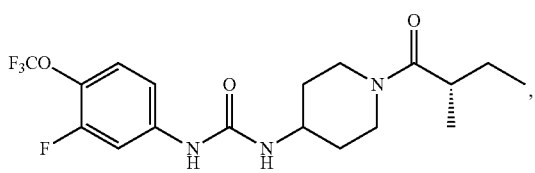 [SMILES: CC[C@H](C)C(=O)N1CCC(NC(=O)Nc2ccc(OC(F)(F)F)c(F)c2)CC1]
or a pharmaceutically acceptable salt thereof.
* * * * *

UNITED STATES PATENT AND TRADEMARK OFFICE
CERTIFICATE OF CORRECTION

PATENT NO. : 12,251,379 B2
APPLICATION NO. : 16/967115
DATED : March 18, 2025
INVENTOR(S) : Hammock et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1114 days.

Signed and Sealed this
Second Day of September, 2025

Coke Morgan Stewart
*Acting Director of the United States Patent and Trademark Office*